US012673970B2

(12) United States Patent
Salituro et al.

(10) Patent No.: US 12,673,970 B2
(45) Date of Patent: Jul. 7, 2026

(54) NEUROACTIVE STEROIDS AND THEIR METHODS OF USE

(71) Applicant: Sage Therapeutics, LLC, Rockville, MD (US)

(72) Inventors: Francesco G. Salituro, Marlborough, MA (US); Marshall Lee Morningstar, Framingham, MA (US); Maria Jesus Blanco-Pillado, Arlington, MA (US)

(73) Assignee: Sage Therapeutics, LLC, Rockville, MD (US)

( * ) Notice: Subject to any disclaimer, the term of this patent is extended or adjusted under 35 U.S.C. 154(b) by 812 days.

(21) Appl. No.: 17/912,301

(22) PCT Filed: Mar. 18, 2021

(86) PCT No.: PCT/US2021/022933

§ 371 (c)(1),
(2) Date: Sep. 16, 2022

(87) PCT Pub. No.: WO2021/188778

PCT Pub. Date: Sep. 23, 2021

(65) Prior Publication Data

US 2023/0183288 A1 Jun. 15, 2023
US 2024/0239835 A9 Jul. 18, 2024

Related U.S. Application Data

(60) Provisional application No. 62/991,234, filed on Mar. 18, 2020.

(51) Int. Cl.
*C07J 43/00* (2006.01)
*A61P 25/24* (2006.01)
*C07J 41/00* (2006.01)

(52) U.S. Cl.
CPC ............ *C07J 43/003* (2013.01); *A61P 25/24* (2018.01); *C07J 41/0094* (2013.01)

(58) Field of Classification Search
CPC ...................................................... C07J 43/003
See application file for complete search history.

(56) References Cited

U.S. PATENT DOCUMENTS

| | | | |
|---|---|---|---|
| 5,376,645 | A | 12/1994 | Stella et al. |
| 5,925,630 | A | 7/1999 | Upasani et al. |
| 6,277,838 | B1 | 8/2001 | Upasani et al. |
| 9,365,611 | B2 | 6/2016 | Martinez Botella et al. |
| 9,512,165 | B2 | 12/2016 | Martinez Botella et al. |
| 9,725,481 | B2 | 8/2017 | Martinez Botella et al. |
| 10,023,606 | B2 | 7/2018 | Martinez Botella et al. |
| 10,172,871 | B2 | 1/2019 | Martinez Botella et al. |
| 10,342,810 | B2 | 7/2019 | Martinez Botella et al. |
| 10,377,790 | B2 | 8/2019 | Martinez Botella et al. |

(Continued)

FOREIGN PATENT DOCUMENTS

| | | | |
|---|---|---|---|
| CN | 109 503 694 | A | 3/2019 |
| FR | 2969 | M | 7/1904 |
| JP | 58074633 | A * | 5/1983 |
| WO | 1994/27608 | A1 | 12/1994 |
| WO | 1996/016076 | A1 | 5/1996 |
| WO | 1998/005337 | A1 | 2/1998 |
| WO | 2009142594 | A1 | 11/2009 |
| WO | 2013036835 | A1 | 3/2013 |
| WO | 2013/056181 | A1 | 4/2013 |
| WO | 2016/061537 | A1 | 4/2016 |
| WO | 2016083819 | A1 | 6/2016 |
| WO | 2017049044 | A1 | 3/2017 |
| WO | 2018/013613 | A1 | 1/2018 |
| WO | 2020118060 | A1 | 6/2020 |
| WO | 2020135454 | A1 | 7/2020 |
| WO | 2020243488 | A1 | 12/2020 |
| WO | 2021142477 | A1 | 7/2021 |

OTHER PUBLICATIONS

Golander et al. (Archiv der Pharmazie, 1979, 312(4), 319-324). (Year: 1979).*

Bellini et al. (Farmaco, Edizione Scientifica (1984), 39(4), 305-315) (Year: 1984).*

Hilgers et al. (Tetrahedron Letters, (1984), 25(17), 1765-1768). (Year: 1984).*

Mara V. Dansey et al. "Synthesis and GABA receptor activity of A—homo analogues of neuroactive steroids", European Journal of Medicinal Chemistry, vol. 45, No. 7, Mar. 26, 2010, pp. 3063-3069.

Cristina Sunol et al. "Activity of B-nor Analogues of Neurosteroids on the Gaba A Receptor in Primary Neuronal Cultures", Journal of Medicinal Chemistry, vol. 49, No. 11, Jun. 1, 2006, pp. 3225-3234.

(Continued)

*Primary Examiner* — Susanna Moore
(74) *Attorney, Agent, or Firm* — Honigman LLP; Andrew N. Weber; Jonathan P. O'Brien

(57) ABSTRACT

Provided herein is a compound of Formula (I), or a pharmaceutically acceptable salt thereof, wherein $R^{2a}$, $R^{2b}$, $R^3$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, $R^{20b}$, X, A, Z, q, u, r, s, t, m, and n are defined herein. Also provided herein are pharmaceutical compositions comprising a compound of Formula (I) and methods of using the compounds, e.g., in the treatment of CNS-related disorders.

(I)

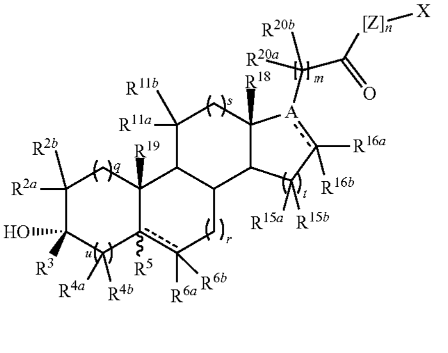

58 Claims, No Drawings

(56) References Cited

U.S. PATENT DOCUMENTS

| | | | |
|---|---|---|---|
| 10,435,431 | B2 | 10/2019 | Upasani et al. |
| 10,774,108 | B2 | 9/2020 | Martinez Botella et al. |
| 10,822,370 | B2 | 11/2020 | Botella et al. |
| 10,870,677 | B2 | 12/2020 | Martinez Botella et al. |
| 11,236,121 | B2 | 2/2022 | Watson et al. |
| 11,266,663 | B2 | 3/2022 | Pinna et al. |
| 11,369,525 | B1 | 6/2022 | Hermansson et al. |
| 11,643,434 | B2 | 5/2023 | Salituro et al. |
| 2009/0118248 | A1 | 5/2009 | Chang et al. |
| 2014/0148412 | A1 | 5/2014 | Hogenkamp |
| 2015/0158903 | A1 * | 6/2015 | Upasani .................. A61P 25/28 552/611 |
| 2016/0229887 | A1 | 8/2016 | Martinez Botella et al. |
| 2017/0342102 | A1 | 11/2017 | Martinez Botella et al. |
| 2019/0177358 | A1 | 6/2019 | Martinez Botella et al. |
| 2019/0233465 | A1 | 8/2019 | Robichaud et al. |
| 2020/0281943 | A1 | 9/2020 | Hoffmann et al. |
| 2021/0139530 | A1 | 5/2021 | Su et al. |
| 2021/0363175 | A1 | 11/2021 | Salituro et al. |
| 2023/0113666 | A1 | 4/2023 | Martinez Botella et al. |
| 2023/0257415 | A1 | 8/2023 | Blanco-Pillado et al. |

OTHER PUBLICATIONS

Phillipps G.H. et al., “Water-Soluble Steroidal Anasthetics”, Journal of Steroid Biochemisty, vol. 11, No. 1, Jul. 1, 1979, pp. 79-86.

Gabriel Martinez Botella et al. “Neuroactive Steroids. 1. Positive Allosteric Modulators of the ([gamma]-Aminobutyric Acid) A Receptor: Structure-Activity Relationships of Heterocyclic Substitution at C-21”, Journal of Medicinal Chemistry, vol. 58, No. 8 Apr. 23, 2015, pp. 3500-3511.

Jayakumar, R et al. “Role of Chirality in Drugs” Organic & Medicinal Chem JI, vol. 5, Issue 3, 2018 pp. 001-006.

Search Report and Written Opinion for PCT/US2019/057195 , mail date Jan. 22, 2020.

H.J. Shu et al. “Photodynamic Effects of Steroid-Conjugated Fluorophores on GABAA Receptors”, Molecular Pharmacology, vol. 76, No. 4, Oct. 1, 2009, pp. 754-765.

Search Report and Written Opinion for PCT/US2019/064692 mail date Feb. 27, 2020.

G. Akk et al. “Neurosteroid Access to the GABAA Receptor”, The Journal of Neuroscience, vol. 25, No. 50, Dec. 14, 2005, pp. 11605-11613.

Mariangela Chisari et al. “The Influence of Neuroactive Steroid Lipophilicity on Gaba A Receptor Modulation: Evidence for a Low-Affinity Interaction”, Journal of Neurophysiology, vol. 102, No. 2, Jun. 24, 2009, pp. 1254-1264.

Chen C.Y., et al. “The mechanism investigation in substitution of 21-bromo-3?-hydroxyl-3?-methoxymethyl-5?-pregnan-20-one with nucleophiles”, Steroids, Elsevier Science Publishers, New York, NY, US, vol. 71, No. 11-12, Nov. 1, 2006, pp. 942-948.

Search Report and Written Opinion for PCT/US2021/022933 mail date Sep. 16, 2021.

Dauncey, E.M., et al. Photoinduced Remote Functionalisations by Iminyl Radical Promoted C—C and C—H Bond Cleavage Cascades. Angewandte Chemie International Edition, 2018, v.57, pp. 744-748.

Losub, A.V., et al. Nickel-Catalyzed Selective Reduction of Caroxylic Acids to Aldehydes. Organic Letters, 2019, v.21, pp. 7804-7808.

Magiera, K., et al. Lithocholic Acid Hydroxyamide Destabilizes Cyclin D1 and Induces G0/G1 Arrest by Inhibiting Deubiquitinase USP2a. Cell Chemical Biology, 2017, v.24, pp. 458-470.

Xie, L., et al. Iridum-Catalyzed Reductive Ugi-Type Reactions of Tertiary Amides. Nature Communications, 2018, v.9, pp. 2841(1-8).

Zecchini, G.P., et al. In Situ Selective Protections of Aldehydes via Aldimines: Simple Conversions of Ketoaldehydes to Methylene Aldehydes and to Methylhydroxy Aldehydes. Tetrahedron, 1983, v.39, pp. 2709-2713.

Paradisi, M., et al. Selective Reduction of 3-Keto Group in Steroidal Ketoaldehydes, Tetrahedron, 1982, v.38(12), pp. 1827-1829.

Hilgers, G., et al. Cholic Acid - An Attractive Source for the Preparation of 5B-Pregnane-3, 20-Dione, 3a-Hydroxy-5b-Pregna-20-One and Progesterone, Tetrahedron Letters, 1984, v.25(17), pp. 1765-1768.

* cited by examiner

NEUROACTIVE STEROIDS AND THEIR METHODS OF USE

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (a change of potential occurs from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by γ-aminobutyric acid (GABA), a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids. See, e.g., Lan, N. C. et al., *Neurochem. Res.* (1991) 16:347-356.

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232: 1004-1007 (1986); Harrison, N. L. et al., *J Pharmacol. Exp. Ther.* 241:346-353 (1987)).

New and improved compounds are needed that act as modulating agents for brain excitability, as well as agents for the prevention and treatment of CNS-related diseases. The compounds, compositions, and methods described herein are directed toward this end.

SUMMARY OF THE INVENTION

Provided herein are compounds designed to act as GABA receptor modulators. In some embodiments, such compounds are envisioned to be useful as therapeutic agents for treating a CNS-related disorder.

In an aspect, provided herein is a compound of Formula I:

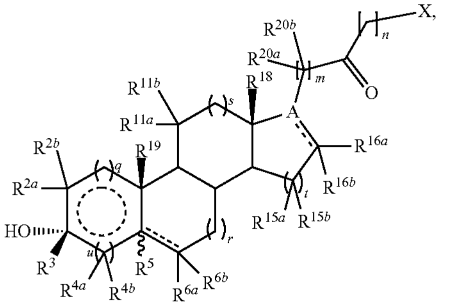

(I)

or a pharmaceutically acceptable salt thereof;

wherein:

- m is 0, 1, 2, or 3;
- $m_1$ is 0, 1, or 2;
- n is 1, 2, 3 or 4;
- $n_1$ is 0, 1, 2, 3, 4 or 5;
- q is independently 0, 1, 2, or 3;
- r is independently 0, 1 or 2;
- s is independently 0, 1 or 2;
- t is independently 0, 1, 2 or 3;
- u is independently 1 or 2;
- X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $—OR^{A1}$, $—SR^{A1}$, $—N(R^{A1})_2$, $—OC(═O)R^{A1}$, $—OC(═O)OR^{A1}$, $—OC(═O)SR^{A1}$, $—OC(═O)N(R^{A1})_2$, $—SC(═O)R^{A2}$, $—SC(═O)OR^{A1}$, $—SC(═O)SR^{A1}$, $—SC(═O)N(R^{A1})_2$, $—NHC(═O)R^{A1}$, $—NHC(═O)OR^{A1}$, $—NHC(═O)SR^{A1}$, $—NHC(═O)N(R^{A1})_2$, $—OS(═O)_2R^{A2}$, $—OS(═O)_2OR^{A1}$, $—S—S(═O)_2R^{A2}$, $—S—S(═O)_2OR^{A1}$, $—S(═O)R^{A2}$, $—SO_2R^{A2}$, or $—S(═O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
- A is $CR^{17}$ or N, wherein $R^{17}$ is selected from the group consisting of a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from the group consisting of a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group;

A is C when ------ is a double bond;

$R^5$ and one of $R^{6a}$ or $R^{6b}$ is absent when ------ is a double bond;

$R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ are each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, $—(CH_2)_{n1}R^{23}$, $—(CH_2)_{n1}OR^{23}$, $—(CH_2)_{n1}SR^{23}$, $—(CH_2)_{n1}C(O)R^{23}$, $—(CH_2)_{n1}C(O)OR^{23}$, $(CH_2)_{n1}S(O)_{m1}R^{23}$, $—(CH_2)_{n1}NR^{23}R^{24}$, $—(CH_2)_{n1}C(O)NR^{23}R^{24}$, $—(CH_2)_{n1}NR^{23}C(O)R^{24}$ or $—(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $—(CH_2)_{n1}R^{25}$, $—(CH_2)_{n1}OR^{25}$, $—(CH_2)_{n1}SR^{25}$, $—(CH_2)_{n1}C(O)R^{25}$, $—(CH_2)_{n1}C(O)OR^{25}$, $—(CH_2)_{n1}S(O)_{m1}R^{25}$, $—(CH_2)_{n1}NR^{25}R^{26}$, $—(CH_2)_{n1}C(O)NR^{25}R^{26}$, $—(CH_2)_{n1}C(O)NHR^{25}$, $—(CH_2)_{n1}NR^{25}C(O)R^{26}$, and $—(CH_2)_{n1}NR^{25}S(O)_{m1}R^{26}$;

or any two adjacent or non-adjacent groups of $R^3$, $R^2$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ may form a cycloalkyl group, a heteroalkyl group, an aryl group, and a heteroaryl group, wherein the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $—(CH_2)_{n1}R^{25}$, $—(CH_2)_{n1}OR^{25}$, $—(CH_2)_{n1}SR^{25}$, $—(CH_2)_{n1}C(O)R^{25}$, $—(CH_2)_{n1}C(O)OR^{25}$, $—(CH_2)_{n1}S(O)_{m1}R^{25}$, $—(CH_2)_{n1}NR^{25}R^{26}$, $—(CH_2)_{n1}C(O)NR^{25}R^{26}$, $—(CH_2)_{n1}C(O)NHR^{25}$, $—(CH_2)_{n1}NR^{25}C(O)R^{26}$, and $—(CH_2)_{n1}NR^{25}S(O)_{m1}R^{26}$;

or $R^{15a}$ and $R^{15b}$, or $R^{16a}$ and $R^{16b}$ are joined to form an oxo (=O) group;

or one of $R^{15a}$ or $R^{15b}$, and one of $R^{16a}$ or $R^{16b}$ are absent so as to form a double bond;

$R^{22}$, $R^{23}$, $R^{24}$, $R^{25}$, and $R^{26}$ are each independently selected from a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group; and provided that:

when m is 0, either $R^{15a}$ or $R^{15b}$ is not —H.

In some embodiments, the compound is a compound of Formula II:

(II)

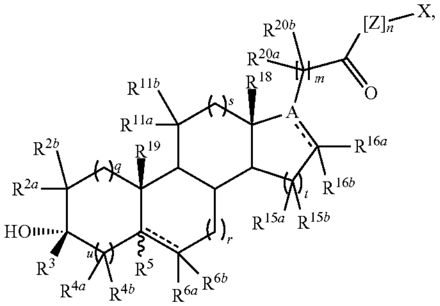

or a pharmaceutically acceptable salt thereof;

wherein:

m is 0, 1, 2, or 3;

$m_1$ is 0, 1, or 2;

n is 1 or 2;

$n_1$ is 0, 1, 2, 3, 4 or 5;

q is independently 0, 1, 2, or 3;

r is independently 0, 1 or 2;

s is independently 0, 1 or 2;

t is independently 0, 1, 2 or 3;

u is independently 1 or 2;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $—OR^{A1}$, $—SR^{A1}$, $—N(R^{A1})_2$, $—OC(=O)R^{A1}$, $—OC(=O)OR^{A1}$, $—OC(=O)SR^{A1}$, $—OC(=O)N(R^{A1})_2$, $—SC(=O)R^{A2}$, $—SC(=O)OR^{A1}$, $—SC(=O)SR^{A1}$, $—SC(=O)N(R^{A1})_2$, $—NHC(=O)R^{A1}$, $—NHC(=O)OR^{A1}$, $—NHC(=O)SR^{A1}$, $—NHC(=O)N(R^{A1})_2$, $—OS(=O)_2R^{A2}$, $—OS(=O)_2OR^{A1}$, $—S—S(=O)_2R^{A2}$, $—S—S(=O)_2OR^{A1}$, $—S(=O)R^{A2}$, $—SO_2R^{A2}$, or $—S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

Z is each independently selected from $—CR^{23}R^{24}—$, $—NR^{23}—$ or —O—;

A is $CR^{17}$ or N, wherein $R^{17}$ is selected from the group consisting of a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from the group consisting of a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group;

A is C when ══════ is a double bond;

$R^5$ and one of $R^{6a}$ or $R^{6b}$ is absent when ══════ is a double bond;

$R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ are each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, $—(CH_2)_{n1}R^{23}$, $—(CH_2)_{n1}OR^{23}$, $—(CH_2)_{n1}SR^{23}$, $—(CH_2)_{n1}C(O)R^{23}$, $—(CH_2)_{n1}C(O)OR^{23}$, $(CH_2)_{n1}S(O)_{m1}R^{23}$, $—(CH_2)_{n1}NR^{23}R^{24}$, $—(CH_2)_{n1}C(O)NR^{23}R^{24}$, $—(CH_2)_{n1}NR^{23}C(O)R^{24}$ or $—(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $—(CH_2)_{n1}R^{25}$, $—(CH_2)_{n1}OR^{25}$, $—(CH_2)_{n1}SR^{25}$, $—(CH_2)_{n1}C(O)R^{25}$, $—(CH_2)_{n1}C(O)OR^{25}$, $—(CH_2)_{n1}S(O)_{m1}R^{25}$, $—(CH_2)_{n1}NR^{25}R^{26}$, $—(CH_2)_{n1}C(O)NR^{25}R^{26}$, $—(CH_2)_{n1}C(O)NHR^{25}$, $—(CH_2)_{n1}NR^{25}C(O)R^{26}$, and $—(CH_2)_{n1}NR^{25}S(O)_{m1}R^{26}$;

or any two adjacent or non-adjacent groups of $R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ may form a cycloalkyl group, a heteroalkyl group, an aryl group, and a heteroaryl group, wherein the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $—(CH_2)_{n1}R^{25}$, $—(CH_2)_{n1}OR^{25}$, $—(CH_2)_{n1}SR^{25}$, $—(CH_2)_{n1}C(O)R^{25}$, $—(CH_2)_{n1}C(O)OR^{25}$, $—(CH_2)_{n1}S(O)_{m1}R^{25}$, $—(CH_2)_{n1}NR^{25}R^{26}$, $—(CH_2)_{n1}C(O)NR^{25}R^{26}$, $—(CH_2)_{n1}C(O)NHR^{25}$, $—(CH_2)_{n1}NR^{25}C(O)R^{26}$, and $—(CH_2)_{n1}NR^{25}S(O)_{m1}R^{26}$;

or $R^{15a}$ and $R^{15b}$, or $R^{16a}$ and $R^{16b}$ are joined to form an oxo (=O) group;

or one of $R^{15a}$ or $R^{15b}$, and one of $R^{16a}$ or $R^{16b}$ are absent so as to form a double bond; and $R^{22}$, $R^{23}$, $R^{24}$, $R^{25}$, and $R^{26}$ are each independently selected from a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group, provided that:

when m is 0 and Z is $—CH_2—$, either $R^{15a}$ or $R^{15b}$ is not —H.

In an aspect, provided herein is a compound of Formula III:

(III)

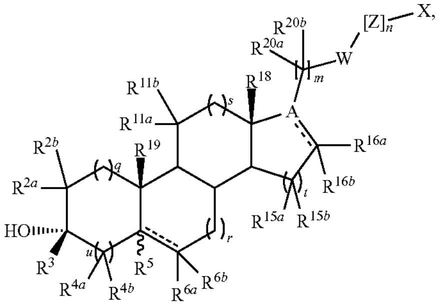

or a pharmaceutically acceptable salt thereof; wherein:

m is 0, 1, 2, or 3;

$m_1$ is 0, 1, or 2;

n is 1 or 2;

$n_1$ is 0, 1, 2, 3, 4 or 5;

q is independently 0, 1, 2, or 3;

r is independently 0, 1 or 2;

s is independently 0, 1 or 2;

t is independently 0, 1, 2 or 3;

u is independently 1 or 2;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $—OR^{A1}$, $—SR^{A1}$, $—N(R^{A1})_2$, $—OC(=O)R^{A1}$, $—OC(=O)OR^{A1}$, $—OC(=O)SR^{A1}$, $—OC(=O)N(R^{A1})_2$, $—SC(=O)R^{A2}$, $—SC(=O)OR^{A1}$, $—SC(=O)SR^{A1}$, $—SC(=O)N(R^{A1})_2$, $—NHC(=O)R^{A1}$, $—NHC(=O)OR^{A1}$, $—NHC(=O)SR^{A1}$, $—NHC(=O)N(R^{A1})_2$, $—OS(=O)_2R^{A2}$, $—OS(=O)_2OR^{A1}$, $—S—S(=O)_2R^{A2}$, $—S—S(=O)_2OR^{A1}$, $—S(=O)R^{A2}$, $—SO_2R^{A2}$, or $—S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

Z is each independently selected from $—CR^{23}R^{24}—$, $—NR^{23}—$ or —O—;

W is each independently selected from $—S(CH_2)_{n1}—$,

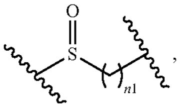, 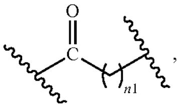,

-continued

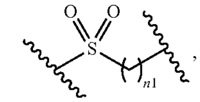, 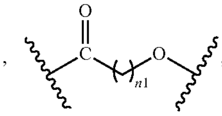,

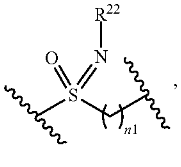, 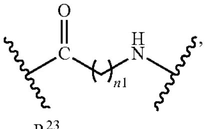, and

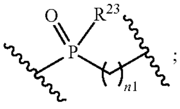;

A is $CR^{17}$ or N, wherein $R^{17}$ is selected from the group consisting of a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from the group consisting of a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group;

A is C when ------ is a double bond;

$R^5$ and one of $R^{6a}$ or $R^{6b}$ is absent when ------ is a double bond;

$R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ are each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, $—(CH_2)_{n1}R^{23}$, $—(CH_2)_{n1}OR^{23}$, $—(CH_2)_{n1}SR^{23}$, $—(CH_2)_{n1}C(O)R^{23}$, $—(CH_2)_{n1}C(O)OR^{23}$, $—(CH_2)_{n1}S(O)_{m1}R^{23}$, $—(CH_2)_{n1}NR^{23}R^{24}$, $—(CH_2)_{n1}C(O)NR^{23}R^{24}$, $—(CH_2)_{n1}NR^{23}C(O)R^{24}$ or $—(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $—(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$;

or any two adjacent or non-adjacent groups of $R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ may form a cycloalkyl group, a heteroalkyl group, an aryl group, and a heteroaryl group, wherein the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$; and $R^{22}$, $R^{23}$, $R^{24}$, $R^{25}$, and $R^{26}$ are each independently selected from a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group;

provided that:

when m is 0;

Z is $-CH_2-$;

W is

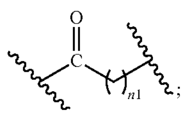

$n_1$ is 0; and either $R^{15a}$ or $R^{15b}$ is not —H.

In some embodiments, the compound is a compound of Formula IV-A or IV-B:

(IV-A)

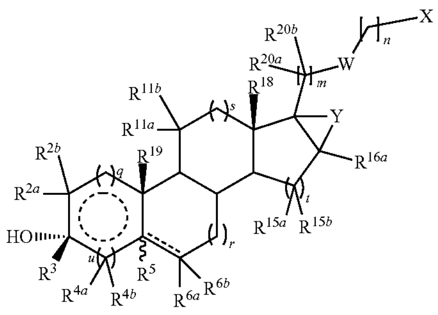

or (IV-B)

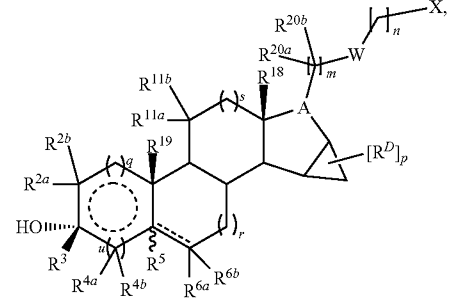

or a pharmaceutically acceptable salt thereof;

wherein:

m is 0, 1, 2, or 3;

$m_1$ is 0, 1, or 2;

n is 1 or 2;

$n_1$ is 0, 1, 2, 3, 4 or 5;

p is 0, 1, 2, 3 or 4;

q is independently 0, 1, 2, or 3;

r is independently 0, 1 or 2;

s is independently 0, 1 or 2;

t is independently 0, 1, 2 or 3;

u is independently 1 or 2;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-SR^{A1}$, $-N(R^{A1})_2$, $-OC(=O)R^{A1}$, $-OC(=O)OR^{A1}$, $-OC(=O)SR^{A1}$, $-OC(=O)N(R^{A1})_2$, $-SC(=O)R^{A2}$, $-SC(=O)OR^{A1}$, $-SC(=O)SR^{A1}$, $-SC(=O)N(R^{A1})_2$, $-NHC(=O)R^{A1}$, $-NHC(=O)OR^{A1}$, $-NHC(=O)SR^{A1}$, $-NHC(=O)N(R^{A1})_2$, $-OS(=O)_2R^{A2}$, $-OS(=O)_2OR^{A1}$, $-S-S(=O)_2R^{A2}$, $-S-S(=O)_2OR^{A1}$, $-S(=O)R^{A2}$, $-SO_2R^{A2}$, or $-S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

Z is each independently selected from $—CR^{23}R^{24}—$, $—NR^{23}—$ or —O—;

W is each independently selected from $—S(CH_2)_{n1}—$,

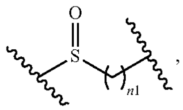
,
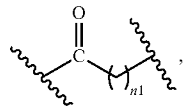
,
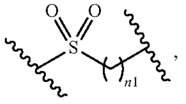
,
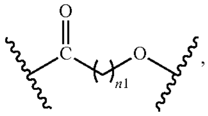
,
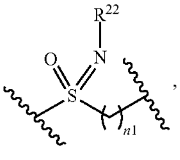
,
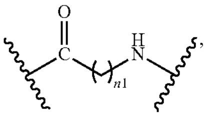
, and
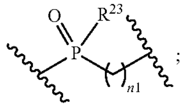
;

Y is $—C(R^{23})_2—$ or oxygen atom;

$R^D$ is each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, $—(CH_2)_{n1}R^{23}$, $—(CH_2)_{n1}OR^{23}$, $—(CH_2)_{n1}SR^{23}$, $—(CH_2)_{n1}C(O)R^{23}$, $—(CH_2)_{n1}C(O)OR^{23}$, $—(CH_2)_{n1}S(O)_{m1}R^{23}$, $—(CH_2)_{n1}S(O)(NR^{23})R^{24}$, $—(CH_2)_{n1}NR^{23}R^{24}$, $—(CH_2)_{n1}C(O)NR^{23}R^{24}$, $—(CH_2)_{n1}NR^{23}C(O)R^{24}$ or $—(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a cycloalkyl group, a heterocyclic group, an aryl group, a heteroaryl group, $—(CH_2)_{n1}R^{25}$, $—(CH_2)_{n1}OR^{25}$, $—(CH_2)_{n1}SR^{25}$, $—(CH_2)_{n1}C(O)R^{25}$, $—(CH_2)_{n1}C(O)OR^{25}$, $—(CH_2)_{n1}S(O)_{m1}R^{25}$, $—(CH_2)_{n1}NR^{25}R^{26}$, $—(CH_2)_{n1}C(O)NR^{25}R^{26}$, $—(CH_2)_{n1}C(O)NHR^{25}$, $—(CH_2)_{n1}NR^{25}C(O)R^{26}$, and $—(CH_2)_{n1}NR^{25}S(O)_{m1}R^{26}$;

$R^5$ and one of $R^{6a}$ or $R^{6b}$ is absent when ------ is a double bond;

$R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ are each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, $—(CH_2)_{n1}R^{23}$, $—(CH_2)_{n1}OR^{23}$, $—(CH_2)_{n1}SR^{23}$, $—(CH_2)_{n1}C(O)R^{23}$, $—(CH_2)_{n1}C(O)OR^{23}$, $—(CH_2)_{n1}S(O)_{m1}R^{23}$, $—(CH_2)_{n1}NR^{23}R^{24}$, $—(CH_2)_{n1}C(O)NR^{23}R^{24}$, $—(CH_2)_{n1}NR^{23}C(O)R^{24}$ or $—(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $—(CH_2)_{n1}R^{25}$, $—(CH_2)_{n1}OR^{25}$, $—(CH_2)_{n1}SR^{25}$, $—(CH_2)_{n1}C(O)R^{25}$, $—(CH_2)_{n1}C(O)OR^{25}$, $—(CH_2)_{n1}S(O)_{m1}R^{25}$, $—(CH_2)_{n1}NR^{25}R^{26}$, $—(CH_2)_{n1}C(O)NR^{25}R^{26}$, $—(CH_2)_{n1}C(O)NHR^{25}$, $—(CH_2)_{n1}NR^{25}C(O)R^{26}$, and $—(CH_2)_{n1}NR^{25}S(O)_{m1}R^{26}$;

or any two adjacent or non-adjacent groups of $R^3$, $R^{2a}$, $R^{2b}$, $R^{4a}$, $R^{4b}$, $R^5$, $R^{6a}$, $R^{6b}$, $R^{11a}$, $R^{11}$, $R^{15a}$, $R^{15b}$, $R^{16a}$, $R^{16b}$, $R^{18}$, $R^{19}$, $R^{20a}$, or $R^{20b}$ may form a cycloalkyl group, a heteroalkyl group, an aryl group, and a heteroaryl group, wherein the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $—(CH_2)_{n1}R^{25}$, $—(CH_2)_{n1}OR^{25}$, $—(CH_2)_{n1}SR^{25}$, $—(CH_2)_{n1}C(O)R^{25}$, $—(CH_2)_{n1}C(O)OR^{25}$, $—(CH_2)_{n1}S(O)_{m1}R^{25}$, $—(CH_2)_{n1}NR^{25}R^{26}$, $—(CH_2)_{n1}C(O)NR^{25}R^{26}$, $—(CH_2)_{n1}C(O)NHR^{25}$, $—(CH_2)_{n1}NR^{25}C(O)R^{26}$, and $—(CH_2)_{n1}NR^{25}S(O)_{m1}R^{26}$;

or $R^{15a}$ and $R^{15b}$, or $R^{16a}$ and $R^{16b}$ are joined to form an oxo (=O) group;

or one of $R^{15a}$ or $R^{15b}$, and one of $R^{16a}$ or $R^{16b}$ are absent so as to form a double bond; and $R^{22}$, $R^{23}$, $R^{24}$, $R^{25}$, and $R^{26}$ are each independently selected from a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group.

In some embodiments, provided herein is a compound of Formula V:

(V)

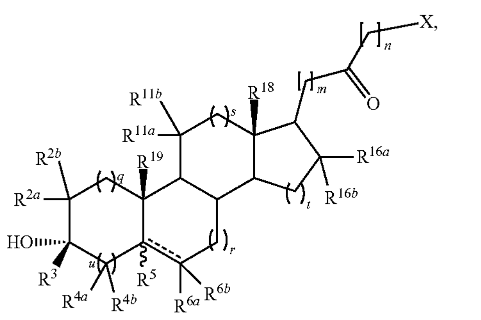

or a pharmaceutically acceptable salt thereof;

wherein:

m is 0, 1, 2, or 3;

n is 1 or 2;

q is independently 0, 1, 2, or 3;

r is independently 0, 1 or 2;

s is independently 0, 1 or 2;

t is independently 0, 1, 2 or 3;

u is independently 1 or 2;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-SR^{A1}$, $-N(R^{A1})_2$, $-OC(=O)R^{A1}$, $-OC(=O)OR^{A1}$, $-OC(=O)SR^{A1}$, $-OC(=O)N(R^{A1})_2$, $-SC(=O)R^{A2}$, $-SC(=O)OR^{A1}$, $-SC(=O)SR^{A1}$, $-SC(=O)N(R^{A1})_2$, $-NHC(=O)R^{A1}$, $-NHC(=O)OR^{A1}$, $-NHC(=O)SR^{A1}$, $-NHC(=O)N(R^{A1})_2$, $-OS(=O)_2R^{A2}$, $-OS(=O)_2OR^{A1}$, $-S-S(=O)_2R^{A2}$, $-S-S(=O)_2OR^{A1}$, $-S(=O)R^{A2}$, $-SO_2R^{A2}$, or $-S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^5$ is hydrogen or methyl, or when ------ is a double bond, $R^5$ and one of $R^{6a}$ or $R^{6b}$ is absent;

$R^{19}$ is hydrogen or substituted or unsubstituted alkyl;

$R^{18}$ is substituted or unsubstituted alkyl, substituted or unsubstituted alkenyl, or substituted or unsubstituted alkynyl;

$R^3$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each of $R^{6a}$ and $R^{6b}$ is independently hydrogen, halogen, cyano, hydroxyl, substituted or unsubstituted alkyl, substituted or unsubstituted alkenyl, or substituted or unsubstituted alkynyl; or $R^{6a}$ and $R^{6b}$ are joined to form an oxo (=O) group; and each of $R^{2a}$, $R^{2b}$, $R^{4a}$, $R^4$, $R^{11a}$, $R^{11b}$, $R^{16a}$, or $R^{11b}$ is independently hydrogen, halogen, cyano, hydroxyl, substituted or unsubstituted alkyl, substituted or unsubstituted alkenyl, substituted or unsubstituted heterocyclyl, substituted or unsubstituted alkynyl, $-OR^{D1}$, $-OC(=O)R^{D1}$, $-NH_2$, $-N(R^{D1})_2$, or $-NR^{D1}C(=O)R^{D1}$, wherein each instance of $R^{D1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a nitrogen protecting group when attached to a nitrogen atom, or two $R^{D1}$ groups are joined to form an substituted or unsubstituted heterocyclic ring; or any one of $R^{2a}$ and $R^{2b}$, or $R^{4a}$ and $R^{4b}$, or $R^{11a}$ and $R^{11b}$ or $R^{16a}$ and $R^{16b}$ are joined to form an oxo (=O) group;

provided that:

q, s, r, u, and t are not simultaneously 1.

In some embodiments, provided herein is a compound of Formula VI:

(VI)

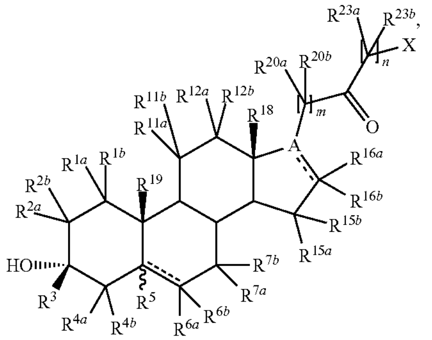

or a pharmaceutically acceptable salt thereof;

wherein:

m is 0, 1, 2, 3, or 4;

n is 0, 1, 2, 3, or 4;

provided that when m is 0, n is not 0 or 1;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each of $R^{1a}$, $R^{1b}$, $R^{2a}$, $R^{2b}$, $R^{4a}$, $R^{4b}$, $R^{7a}$, $R^{7b}$, $R^{11a}$, $R^{11b}$, $R^{12a}$, $R^{12b}$, $R^{15a}$, $R^{15b}$, $R^{16a}$, and $R^{16b}$ is independently hydrogen, halogen, cyano, $—NO_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $—OR^{A1}$, $—N(R^{A1})_2$, $—SR^{A1}$, $—C(=O)R^{A1}$, $—C(=O)OR^{A1}$, $—C(=O)SR^{A1}$, $—C(=O)N(R^{A1})_2$, $—OC(=O)R^{A1}$, $—OC(=O)OR^{A1}$, $—OC(=O)N(R^{A1})_2$, $—OC(=O)SR^{A1}$, $—OS(=O)_2R^{A1}$, $—OS(=O)_2OR^{A1}$, $—OS(=O)_2N(R^{A1})_2$, $—N(R^{A1})C(=O)R^{A1}$, $—N(R^{A1})C(=NR^{A1})R^{A1}$, $—N(R^{A1})C(=O)OR^{A1}$, $—N(R^{A1})C(=O)N(R^{A1})_2$, $—N(R^{A1})C(=NR^{A1})N(R^{A1})_2$, $—N(R^{A1})S(=O)_2R^{A1}$, $—N(R^{A1})S(=O)_2OR^{A1}$, $—N(R^{A1})S(=O)_2N(R^{A1})_2$, $—SC(=O)R^{A1}$, $—SC(=O)OR^{A1}$, $—SC(=O)SR^{A1}$, $—SC(=O)N(R^{A1})_2$, $—S(=O)_2R^{A1}$, $—S(=O)_2OR^{A1}$, or $—S(=O)_2N(R^{A1})_2$, wherein each instance of $R^{A1}$ is independently selected from hydrogen, substituted or unsubstituted alkyl, substituted or unsubstituted alkenyl, substituted or unsubstituted alkynyl, substituted or unsubstituted carbocyclyl, or substituted or unsubstituted heterocyclyl, substituted or unsubstituted aryl, substituted or unsubstituted heteroaryl, an oxygen protecting group when attached to oxygen, a nitrogen protecting group when attached to nitrogen, or a sulfur protecting group when attached to sulfur; or $R^{11a}$ and $R^{11b}$ are joined to form an oxo (=O) group; or $R^{12a}$ and $R^{12b}$ are joined to form an oxo (=O) group; or $R^{15a}$ and $R^{15b}$ are joined to form an oxo (=O) group; or $R^{16a}$ and $R^{16b}$ are joined to form an oxo (=O) group; or $R^{4a}$ and $R^{4b}$ are joined to form an oxo (=O) group; or $R^{7a}$ and $R^{7b}$ are joined to form an oxo (=O) group; or $R^{2a}$ and $R^{2b}$ are joined to form an oxo (=O) group; or $R^{1a}$ and $R^{1b}$ are joined to form an oxo (=O) group;

$R^3$ is hydrogen, substituted or unsubstituted alkyl;

$R^5$ is hydrogen or methyl;

each of $R^{6a}$ and $R^{6b}$ is independently hydrogen, halogen, cyano, $—NO_2$, —OH, substituted or unsubstituted alkyl, substituted or unsubstituted alkenyl, or substituted or unsubstituted alkynyl; or $R^{6a}$ and $R^{6b}$ are joined to form an oxo (=O) group;

$R^{18}$ is substituted or unsubstituted alkyl, substituted or unsubstituted alkenyl, or substituted or unsubstituted alkynyl;

$R^{19}$ is hydrogen or substituted or unsubstituted alkyl;

and $R^{20a}$, $R^{20b}$, $R^{23a}$, or $R^{23b}$ are each independently selected from the group consisting of a hydrogen atom, an alkyl group, a halogenated alkyl group, an alkoxy group, a halogenated alkoxy group.

DETAILED DESCRIPTION

As generally described herein, the present invention provides compounds designed, for example, to act as GABA receptor modulators. In certain embodiments, such compounds are envisioned to be useful as therapeutic agents for treating a CNS-related disorder (e.g., a disorder as described herein, for example depression, such as post-partum depression or major depressive disorder).

I. DEFINITIONS

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, *March's Advanced Organic Chemistry,* 5$^{th}$ Edition, John Wiley & Sons, Inc., New York, 2001; Larock, Comprehensive Organic Transformations, VCH Publishers, Inc., New York, 1989; and Carruthers, *Some Modern Methods of Organic Synthesis,* 3$^{rd}$ Edition, Cambridge University Press, Cambridge, 1987.

Isomers, e.g., stereoisomers, can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein, the term "diastereomeric purity" refers to the amount of a compound having the depicted absolute stereochemistry, expressed as a percentage of the total amount of the depicted compound and its diastereomers. The term "diastereomierically pure" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the diastereomer. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC).

In the compositions provided herein, an enantiomerically pure compound can be present with other active or inactive ingredients. For example, a pharmaceutical composition comprising enantiomerically pure R-position/center/carbon compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., $—CH_3$). In certain embodiments, the alkyl group is substituted $C_{1-10}$ alkyl. Common alkyl abbreviations include Me ($—CH_3$), Et ($—CH_2CH_3$), iPr ($—CH(CH_3)_2$), nPr ($—CH_2CH_2CH_3$), n-Bu ($—CH_2CH_2CH_2CH_3$), or i-Bu ($—CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene ($—CH_2—$), ethylene ($—CH_2CH_2—$), propylene ($—CH_2CH_2CH_2—$), butylene ($—CH_2CH_2CH_2CH_2—$), pentylene ($—CH_2CH_2CH_2CH_2CH_2—$), hexylene ($—CH_2CH_2CH_2CH_2CH_2CH_2—$), and the like. Exemplary substituted alkylene groups, e.g., substituted with one or more alkyl (methyl) groups, include but are not limited to, substituted methylene ($—CH(CH_3)—$, ($—C(CH_3)—$), substituted ethylene ($—CH(CH_3)CH_2—$, $—CH_2CH(CH_3)—$, $—C(CH_3)_2CH_2—$, $—CH_2C(CH_3)_2—$), substituted propylene ($—CH(CH_3)CH_2CH_2—$, $—CH_2CH(CH_3)CH_2—$, $—CH_2CH_2CH(CH_3)—$, $—C(CH_3)_2CH_2CH_2—$, $—CH_2C(CH_3)_2CH_2—$, $—CH_2CH_2C(CH_3)_2—$), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and 1 or 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group is substituted with one or more of groups selected from halogen, $C_{1-8}$ alkyl, $C_{1-8}$ haloalkyl, cyano, hydroxy, $C_{1-8}$ alkoxy, and amino.

Examples of representative substituted aryls include the following

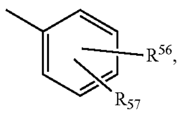,
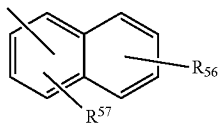 and

-continued

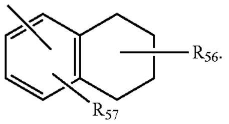

wherein one of $R^{56}$ and $R^{57}$ may be hydrogen and at least one of $R^{56}$ and $R^{57}$ is each independently selected from $C_{1-8}$ alkyl, $C_{1-8}$ haloalkyl, 4-10 membered heterocyclyl, alkanoyl, $C_{1-8}$ alkoxy, heteroaryloxy, alkylamino, arylamino, heteroarylamino, $—NR^{58}COR^{59}$, $—NR^{58}SOR^{59}$, $—NR^{8}SO_2R^{59}$, —COOalkyl, —COOaryl, $—CONR^{58}R^{59}$, $—CONR^{58}OR^{59}$, $—NR^{58}R^{59}$, $—SO_2NR^{58}R^{59}$, —S-alkyl, —S—O-alkyl, $—SO_2$-alkyl, —S-aryl, —S—O-aryl, $—SO_2$-aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_{1-8}$ alkyl, $C_{1-4}$ haloalkyl, $C_{3-10}$ cycloalkyl, 4-10 membered heterocyclyl, $C_{6-10}$ aryl, substituted $C_{6-10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

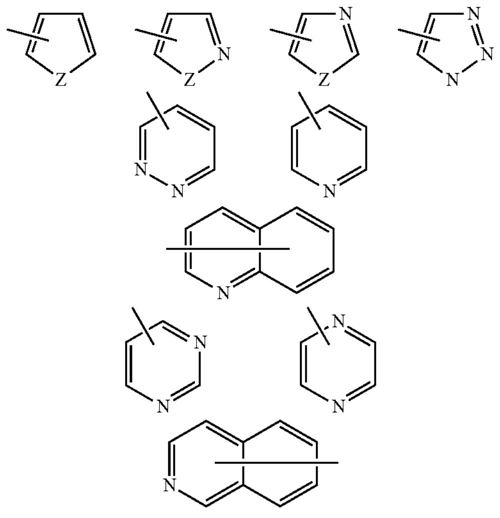

-continued

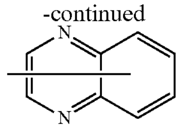

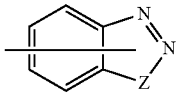

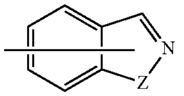

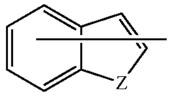

wherein each Z is selected from carbonyl, N, $NR^{65}$, O, and S; and $R^{65}$ is independently hydrogen, $C_{1-8}$ alkyl, $C_{3-10}$ cycloalkyl, 4-10 membered heterocyclyl, $C_{6-10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(═O)$CH_3$), cyclohexylcarbonyl, cyclohexylmethylcarbonyl, benzoyl (—C(═O)Ph), benzylcarbonyl (—C(═O)$CH_2$Ph), —C(O)—$C_{1-8}$ alkyl, —C(O)—$(CH_2)_t$($C_{6-10}$ aryl), —C(O)—$(CH_2)_t$(5-10 membered heteroaryl), —C(O)—$(CH_2)_t$($C_{3-10}$ cycloalkyl), and —C(O)—$(CH_2)_t$(4-10 membered heterocyclyl), wherein t is an integer from 0 to 4. In certain embodiments, $R^{21}$ is $C_{1-8}$ alkyl, substituted with halogen or hydroxy; or $C_{3-10}$ cycloalkyl, 4-10 membered heterocyclyl, $C_{6-10}$ aryl, arylalkyl, 5-10 membered heteroaryl or heteroarylalkyl, each of which is substituted with unsubstituted $C_{1-4}$ alkyl, halogen, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy.

"Alkoxy" refers to the group —$OR^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_{6-10}$ aryl, aryloxy, carboxyl, cyano, $C_{3-10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S$(O)_2$— and aryl-S$(O)_2$—. Exemplary 'substituted alkoxy' groups include, but are not limited to, —O—$(CH_2)_t$($C_{6-10}$ aryl), —O—$(CH_2)_t$(5-10 membered heteroaryl), —O—$(CH_2)_t$($C_{3-10}$ cycloalkyl), and —O—$(CH_2)_t$(4-10 membered heterocyclyl), wherein t is an integer from 0 to 4 and any aryl, heteroaryl, cycloalkyl or heterocyclyl groups present, may themselves be substituted by unsubstituted $C_{1-4}$ alkyl, halogen, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy. Particular exemplary 'substituted alkoxy' groups are —$OCF_3$, —$OCH_2CF_3$, —$OCH_2$Ph, —$OCH_2$-cyclopropyl, —$OCH_2CH_2OH$, and —$OCH_2CH_2NMe_2$.

"Amino" refers to the radical —$NH_2$.

"Oxo group" refers to —C(═O)—.

"Substituted amino" refers to an amino group of the formula —N$(R^{38})_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_{1-8}$ alkyl, $C_{3-8}$ alkenyl, $C_{3-8}$ alkynyl, $C_{6-10}$ aryl, 5-10 membered heteroaryl, 4-10 membered heterocyclyl, or $C_{3-10}$ cycloalkyl; or $C_{3-8}$ alkyl, substituted with halogen or hydroxy; $C_{3-8}$ alkenyl, substituted with halogen or hydroxy; $C_{3-8}$ alkynyl, substituted with halogen or hydroxy, or —$(CH_2)_t$($C_6$-$C_{10}$ aryl), —$(CH_2)_t$(5-10 membered heteroaryl), —$(CH_2)_t$($C_3$-$C_{10}$ cycloalkyl), or —$(CH_2)_t$(4-10 membered heterocyclyl), wherein t is an integer between 0 and 8, each of which is substituted by unsubstituted $C_{1-4}$ alkyl, halogen, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t$($C_6$-$C_{10}$ aryl), —$NR^{39}$—$(CH_2)_t$(5-10 membered heteroaryl), —$NR^{39}$—$(CH_2)_t$($C_{3-10}$ cycloalkyl), and —$NR^{39}$—$(CH_2)_t$(4-10 membered heterocyclyl), wherein t is an integer from 0 to 4, for instance 1 or 2, each $R^{39}$ independently represents H or $C_{1-8}$ alkyl; and any alkyl groups present, may themselves be substituted by halogen, substituted or unsubstituted amino, or hydroxy; and any aryl, heteroaryl, cycloalkyl, or heterocyclyl groups present, may themselves be substituted by unsubstituted $C_{1-4}$ alkyl, halogen, unsubstituted $C_{1-4}$ alkoxy, unsubstituted $C_{1-4}$ haloalkyl, unsubstituted $C_{1-4}$ hydroxyalkyl, or unsubstituted $C_{1-4}$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halogen group is either fluoro or chloro.

"Haloalkyl" refers to an alkyl radical in which the alkyl group is substituted with one or more halogens. Typical haloalkyl groups include, but are not limited to, trifluoromethyl, difluoromethyl, fluoromethyl, chloromethyl, dichloromethyl, dibromoethyl, tribromomethyl, tetrafluoroethyl, and the like.

"Hydroxy" refers to the radical —OH.

"Nitro" refers to the radical —$NO_2$.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —SR—, —$SSR^{cc}$, —C(=O)$R^{aa}$, —$CO_2H$, —CHO, —$C(OR^{cc})_2$, —$CO_2R^{aa}$, —OC(=O)$R^{aa}$, —$OCO_2R^{aa}$, —C(=O)$N(R^{bb})_2$, —OC(=O)$N(R^{bb})_2$, —$NR^{bb}$C(=O)$R^{aa}$, —$NR^{bb}CO_2R^{aa}$, —$NR^{bb}$C(=O)$N(R^{bb})_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)$N(R^{bb})_2$, —OC(=$NR^{bb}$)$N(R^{bb})_2$, —$NR^{bb}$C(=$NR^{bb}$)$N(R^{bb})_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —$Si(R^{aa})_3$, —$OSi(R^{aa})_3$—C(=S)$N(R^{bb})_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)$OR^{aa}$, —SC(=O)$R^{aa}$, —P(=O)$_2R^{aa}$, —OP(=O)$_2R^{aa}$, —P(=O)$(R')_2$, —OP(=O)$(R^{aa})_2$, —OP(=O)$(OR^{cc})_2$, —P(=O)$_2N(R^{bb})_2$, —OP(=O)$_2N(R^{bb})_2$, —P(=O)$(NR^{bb})_2$, —OP(=O)$(NR^{bb})_2$, —$NR^{bb}$P(=O)$(OR^{cc})_2$—$NR^{bb}$P(=O)$(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, =$NN(R^{bb})_2$, =$NNR^{bb}$C(=O)$R^{aa}$, =$NNR^{bb}$C(=O)$OR^{aa}$, —$NNR^{bb}$S(=O)$_2R^{aa}$, —$NR^{bb}$, or =$NOR^{cc}$;

each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})$, —CN, —C(=O)$R^{aa}$, —C(=O)$N(R^{cc})_2$, —$CO_2R^{aa}$, —$SO_2R^{aa}$, —C(=$NR^{cc}$)$OR^{aa}$, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, —P(=O)$_2R^{aa}$, —P(=O)$(R^{aa})_2$, —P(=O)$_2N(R^{cc})_2$, —P(=O)$(NR^{cc})_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{f})_3^+X^-$, —$N(OR^{ee})R^{ff}$, —SH, —$SR^{ee}$, —$SSR^{ee}$, —C(=O)$R^{ee}$, —$CO_2H$, —$CO_2R^{ee}$, —OC(=O)$R^{ee}$, —$OCO_2R^{ee}$, —C(=O)$N(R^{ff})_2$, —OC(=O)$N(R^{ff})_2$, —$NR^{ee}$C(=O)$R^{ee}$, —$NR^{ff}CO_2R^{ee}$, —$NR^{ff}$C(=O)$N(R^{ff})_2$, —C(=$NR^{ff}$)$OR^{ee}$, —OC(=$NR^{ff}$)$R^{ee}$, —OC(=$NR^{ff}$)$OR^{ee}$, —C(=$NR^{ff}$)$N(R^{ff})_2$, —OC(=$NR^{ff}$)$N(R^{ff})_2$, —$NR^{ff}$C(=$NR^{ff}$)$N(Re)_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(=O)$R^{ee}$, —$Si(R^{ee})_3$, —$OSi(R^{ee})_3$, —C(=S)$N(R^{ff})_2$, —C(=O)$SR^{ee}$, —C(=S)$SR^{ee}$, —SC(=S)$SR^{ee}$, —P(=O)$_2R^{ee}$, —P(=O)$(R^{ee})_2$, —OP(=O)$(R^{ee})_2$, —OP(=O)$(OR^{ee})_2$, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3{}^+X^-$, —NH($C_{1-6}$ alkyl)$_2{}^+X^-$, —$NH_2$($C_{1-6}$ alkyl)$^+X^-$, —$NH_3{}^+X^-$, —N($OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$, —C(=S)N($C_{1-6}$ alkyl)$_2$, —C(=S)NH($C_{1-6}$ alkyl), —C(=S)$NH_2$, —C(=O)S($C_{1-6}$ alkyl), —C(=S)$SC_{1-6}$ alkyl, —SC(=S)$SC_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)($OC_{1-6}$ alkyl)$_2$, —$C_{1-6}$ alkyl, —$C_{1-6}$ haloalkyl, —$C_{2-6}$ alkenyl, —$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In some embodiments, carbon atom substituents include halogen, —CN, —OH, —$OR^{aa}$, —N($R^{bb}$)$_2$, —$CO_2H$, —$CO_2R^{aa}$, —OC(=O)$R^{aa}$, —C(=O)N($R^{bb}$)$_2$, —$SO_2R^{aa}$, $C_{1-6}$ alkyl, —$C_{1-6}$ haloalkyl, $C_{3-10}$ carbocyclyl, 5-6 membered heterocyclyl, phenyl, and 5-6 membered heteroaryl, wherein each instance of $R^{aa}$ is, independently, selected from hydrogen, $C_{1-6}$ alkyl, $C_{1-6}$ haloalkyl, $C_{2-10}$ alkenyl, $C_{2-10}$ alkynyl, $C_{3-10}$ carbocyclyl, 5-6 membered heterocyclyl, phenyl, and 5-6 membered heteroaryl; and each instance of $R^{bb}$ is, independently, selected from hydrogen, $C_{1-6}$ alkyl, $C_{1-6}$ haloalkyl, $C_{2-10}$ alkenyl, $C_{2-10}$ alkynyl, $C_{3-10}$ carbocyclyl, 5-6 membered heterocyclyl, phenyl, and 5-6 membered heteroaryl.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3$, $ClO_4{}^-$, $OH^-$, $H_2PO_4{}^-$, $HSO_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

These and other exemplary substituents are described in more detail in the Detailed Description, and Claims. The invention is not intended to be limited in any manner by the above exemplary listing of substituents.

As used herein, the term "modulation" refers to the inhibition or potentiation of $GABA_A$ receptor function. A "modulator" (e.g., a modulator compound) may be, for example, an agonist, partial agonist, antagonist, or partial antagonist of the $GABA_A$ receptor.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

The term "prodrug" is intended to encompass therapeutically inactive compounds that, under physiological conditions, are converted into the therapeutically active agents of the present invention. One method for making a prodrug is to design selected moieties that are hydrolyzed or cleaved at a targeted in vivo site of action under physiological conditions to reveal the desired molecule which then produces its therapeutic effect. In certain embodiments, the prodrug is converted by an enzymatic activity of the subject.

In an alternate embodiment, the present invention provides prodrugs of compound of Formula (I), wherein the prodrug includes a cleavable moiety on the C3 hydroxy as depicted in Formula (I).

"Tautomers" refer to compounds that are interchangeable forms of a particular compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

In certain embodiments, the substituent present on an oxygen atom is an oxygen protecting group (also referred to as a hydroxyl protecting group). Oxygen protecting groups include, but are not limited to —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R^{aa}$, —$Si(R^{aa})_3$, —P(R')$_2$, —$P(R^{cc})_3$, —P(=O)$_2R^{aa}$, —P(=O)$(R^{aa})_2$—P(=O)$(OR^{cc})_2$, —P(=O)$_2N(R^{bb})_2$, and —P(=O)$(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), 2-methoxyethoxymethyl (MEM), benzyl (Bn), triisopropylsilyl (TIPS), t-butyldimethylsilyl (TBDMS), t-butylmethoxyphenylsilyl (TBMPS), methanesulfonate (mesylate), and tosylate (Ts).

In certain embodiments, the substituent present on an sulfur atom is an sulfur protecting group (also referred to as a thiol protecting group). Sulfur protecting groups include, but are not limited to —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R^{aa}$, —$Si(R^{aa})_3$, —$P(R^{cc})_2$, —$P(R^{cc})_3$, —P(=O)$_2R^{aa}$, —P(=O)$(R^{aa})$, —P(=O)$(OR^{cc})_2$, —P(=O)$_2N(R^{bb})_2$, and —P(=O)$(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

In certain embodiments, the substituent present on a nitrogen atom is an amino protecting group (also referred to herein as a nitrogen protecting group). Amino protecting groups include, but are not limited to —OH, —$OR^{aa}$, —$N(R^{cc})_2$, —C(=O)$R^{aa}$, —C(=O)$OR^{aa}$, —C(=O)$N(R^{cc})_2$, —S(=O)$_2R^{aa}$, —C(=$NR^{cc}$)$R^{aa}$, —C(=$NR^{cc}$)$OR^{aa}$, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, $C_{1-10}$ alkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl groups, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary amino protecting groups include, but are not limited to amide groups (e.g., —C(=O)$R^{aa}$), which include, but are not limited to, formamide and acetamide; carbamate groups (e.g., —C(=O)$OR^{aa}$), which include, but are not limited to, 9-fluorenylmethyl carbamate (Fmoc), t-butyl carbamate (BOC), and benzyl carbamate (Cbz); sulfonamide groups (e.g., —S(=O)$_2R^{aa}$) which include, but are not limited to, p-toluenesulfonamide (Ts), methanesulfonamide (Ms), and N-[2-(trimethylsilyl)ethoxy]methylamine (SEM).

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition. In an alternate embodiment, the present invention contemplates administration of the compounds of the present invention as a prophylactic before a subject begins to suffer from the specified disease, disorder or condition.

In general, the "effective amount" of a compound refers to an amount sufficient to elicit the desired biological response, e.g., to treat a CNS-related disorder, is sufficient to induce anesthesia or sedation. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

In an alternative embodiment, compounds described herein may also comprise one or more isotopic substitutions. For example, hydrogen may be $^{2}H$ (D or deuterium) or $^{3}H$ (T or tritium); carbon may be, for example, $^{13}C$ or $^{14}C$; oxygen may be, for example, $^{18}O$; nitrogen may be, for example, $^{15}N$, and the like. In other embodiments, a particular isotope (e.g., $^{3}H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

As used herein, an "episodic dosing regimen" is a dosing regimen wherein a compound of Formula (I) or a composition comprising a compound of Formula (I) is administered to a subject for a finite period of time in response to the diagnosis of a disorder or symptom thereof, e.g., a diagnosis or symptom of depression. an episode of major depressive disorder, bipolar depression, anxiety, or postpartum depression. In some embodiments, the major depressive disorder is moderate major depressive disorder. In some embodiments, the major depressive disorder is severe major depressive disorder In some embodiments, the compound is formulated as individual dosage units, each unit comprising a compound of Formula (I) and one or more suitable pharmaceutical excipients. In some embodiments, the episodic dosing regimen has a duration of a plurality of weeks, e.g. about 8 weeks. In contrast with chronic administration as defined herein, episodic dosing of a compound occurs over a finite period of time, e.g., from about 2 weeks to about 8 weeks, in response to a diagnosis of a disorder, e.g., depression, or a symptom thereof. In some embodiments, episodic dosing occurs once per day across a plurality of weeks, e.g., from about 2 weeks to about 6 weeks. In one embodiment, the episodic dosing has a duration of two weeks. In some embodiments, more than one episodic dosing regimen is administered to the subject, e.g., two or more episodic regimens throughout the subject's life.

II. COMPOUNDS

It should be appreciated that formulas described herein may reference particular carbon atoms, such as C17, C3, C19, and the like. These references are based on the position of carbon atoms according to steroid nomenclature known and used in the industry, as shown below:

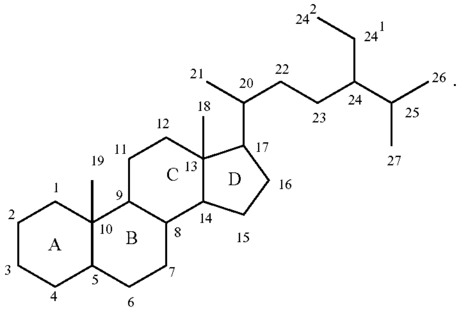

For example, C17 refers to the carbon at position 17 and C3 refers to the carbon at position 3.

In some embodiments, the compound is a compound of Formula I:

(I)

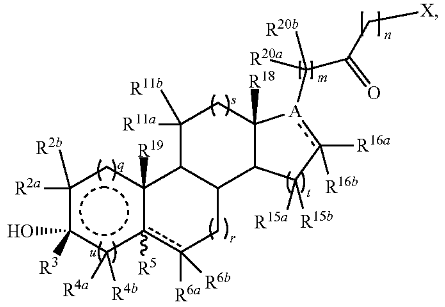

or a pharmaceutically acceptable salt thereof;

wherein:

m is 0, 1, 2, or 3;

$m_1$ is 0, 1, or 2;

n is 1, 2, 3 or 4;

$n_1$ is 0, 1, 2, 3, 4 or 5;

q is independently 0, 1, 2, or 3;

r is independently 0, 1 or 2;

s is independently 0, 1 or 2;

t is independently 0, 1, 2 or 3;

u is independently 1 or 2;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-SR^{A1}$, $-N(R^{A1})_2$, $-OC(=O)R^{A1}$, $-OC(=O)OR^{A1}$, $-OC(=O)SR^{A1}$, $-OC(=O)N(R^{A1})_2$, $-SC(=O)R^{A2}$, $-SC(=O)OR^{A1}$, $-SC(=O)SR^{A1}$, $-SC(=O)N(R^{A1})_2$, $-NHC(=O)R^{A1}$, $-NHC(=O)OR^{A1}$, $-NHC(=O)SR^{A1}$, $-NHC(=O)N(R^{A1})_2$, $-OS(=O)_2R^{A2}$, $-OS(=O)_2OR^{A1}$, $-S-S(=O)_2R^{A2}$, $-S-S(=O)_2OR^{A1}$, $-S(=O)R^{A2}$, $-SO_2R^{A2}$, or $-S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

A is $CR^{17}$ or N, wherein $R^{17}$ is selected from the group consisting of a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from the group consisting of a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroarylgroup;

A is C when ====== is a double bond;

$R^5$ and one of $R^{6a}$ or $R^{6b}$ is absent when ====== is a double bond;

$R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ are each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, $-(CH_2)_{n1}R^{23}$, $-(CH_2)_{n1}OR^{23}$, $-(CH_2)_{n1}SR^{23}$, $-(CH_2)_{n1}C(O)R^{23}$, $-(CH_2)_{n1}C(O)OR^{23}$, $-(CH_2)_{n1}S(O)_{m1}R^{23}$, $-(CH_2)_{n1}NR^{23}R^{24}$, $-(CH_2)_{n1}C(O)NR^{23}R^{24}$, $-(CH_2)_{n1}NR^{23}C(O)R^{24}$, or $-(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$;

or any two adjacent or non-adjacent groups of $R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ may form a cycloalkyl group, a heteroalkyl group, an aryl group, and a heteroaryl group, wherein the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$;

or $R^{15a}$ and $R^{15b}$, or $R^{16a}$ and $R^{16b}$ are joined to form an oxo (=O) group;

or one of $R^{15a}$ or $R^{15b}$, and one of $R^{16a}$ or $R^{16b}$ are absent so as to form a double bond;

$R^{22}$, $R^{23}$, $R^{24}$, $R^{25}$, and $R^{26}$ are each independently selected from a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group; and provided that:

when m is 0, either $R^{15a}$ or $R^{15b}$ is not H.

In some embodiments, the compound is a compound of Formula II:

(II)

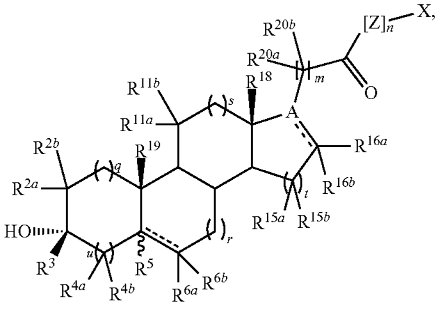

or a pharmaceutically acceptable salt thereof;

wherein:

m is 0, 1, 2, or 3;

$m_1$ is 0, 1, or 2;

n is 1 or 2;

$n_1$ is 0, 1, 2, 3, 4 or 5;
q is independently 0, 1, 2, or 3;
r is independently 0, 1 or 2;
s is independently 0, 1 or 2;
t is independently 0, 1, 2 or 3;
u is independently 1 or 2;
X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-SR^{A1}$, $-N(R^{A1})_2$, $-OC(=O)R^{A1}$, $-OC(=O)OR^{A1}$, $-OC(=O)SR^{A1}$, $-OC(=O)N(R^{A1})_2$, $-SC(=O)R^{A2}$, $-SC(=O)OR^{A1}$, $-SC(=O)SR^{A1}$, $-SC(=O)N(R^{A1})_2$, $-NHC(=O)R^{A1}$, $-NHC(=O)OR^{A1}$, $-NHC(=O)SR^{A1}$, $-NHC(=O)N(R^{A1})_2$, $-OS(=O)_2R^{A2}$, $-OS(=O)_2OR^{A1}$, $-S-S(=O)_2R^{A2}$, $-S-S(=O)_2OR^{A1}$, $-S(=O)R^{A2}$, $-SO_2R^{A2}$, or $-S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
Z is each independently selected from $-CR^{23}R^{24}-$, $-NR^{23}-$, or $-O-$;
A is $CR^{17}$ or N, wherein $R^{17}$ is selected from the group consisting of a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from the group consisting of a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group;
A is C when ------ is a double bond;
$R^5$ and one of $R^{6a}$ or $R^{6b}$ is absent when ------ is a double bond;
$R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ are each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, $-(CH_2)_{n1}R^{23}$, $-(CH_2)_{n1}OR^{23}$, $-(CH_2)_{n1}SR^{23}$, $-(CH_2)_{n1}C(O)R^{23}$, $-(CH_2)_{n1}C(O)OR^{23}$, $-(CH_2)_{n1}S(O)_{m1}R^{23}$, $-(CH_2)_{n1}NR^{23}R^{24}$, $-(CH_2)_{n1}C(O)NR^{23}R^{24}$, $-(CH_2)_{n1}NR^{23}C(O)R^{24}$, or $-(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$;
or any two adjacent or non-adjacent groups of $R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ may form a cycloalkyl group, a heteroalkyl group, an aryl group, and a heteroaryl group, wherein the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$;
or $R^{15a}$ and $R^{15b}$, or $R^{16a}$ and $R^{16b}$ are joined to form an oxo (=O) group;
or one of $R^{15a}$ or $R^{15b}$, and one of $R^{16a}$ or $R^{16b}$ are absent so as to form a double bond; and
$R^{22}$, $R^{23}$, $R^{24}$, $R^{25}$, and $R^{26}$ are each independently selected from a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group, provided that:

when m is 0 and Z is —$CH_2$—, either $R^{15a}$ or $R^{15b}$ is not —H.

In some embodiments, the compound is a compound of Formula III:

(III)

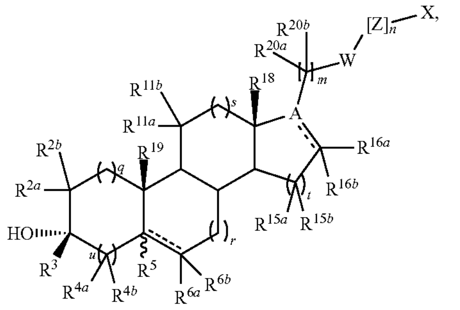

or a pharmaceutically acceptable salt thereof;

wherein:

m is 0, 1, 2, or 3;

$m_1$ is 0, 1, or 2;

n is 1 or 2;

$n_1$ is 0, 1, 2, 3, 4 or 5;

q is independently 0, 1, 2, or 3;

r is independently 0, 1 or 2;

s is independently 0, 1 or 2;

t is independently 0, 1, 2 or 3;

u is independently 1 or 2;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$SR^{A1}$, —$N(R^{A1})_2$, —$OC(=O)R^{A1}$, —$OC(=O)OR^{A1}$, —$OC(=O)SR^{A1}$, —$OC(=O)N(R^{A1})_2$, —$SC(=O)R^{A2}$, —$SC(=O)OR^{A1}$, —$SC(=O)SR^{A1}$, —$SC(=O)N(R^{A1})_2$, —$NHC(=O)R^{A1}$, —$NHC(=O)OR^{A1}$, —$NHC(=O)SR^{A1}$, —$NHC(=O)N(R^{A1})_2$, —$OS(=O)_2R^{A2}$, —$OS(=O)_2OR^{A1}$, —S—$S(=O)_2R^{A2}$, —S—$S(=O)_2OR^{A1}$, —$S(=O)R^{A2}$, —$SO_2R^{A2}$, or —$S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

Z is each independently selected from —$CR^{23}R^{24}$—, —$NR^{23}$—, or —O—;

W is each independently selected from —$S(CH_2)_{n1}$—,

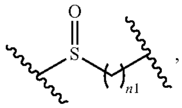, 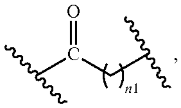,

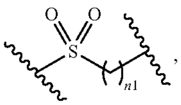, 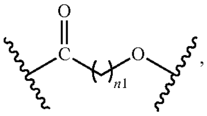,

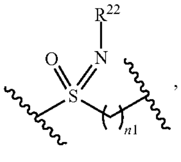, 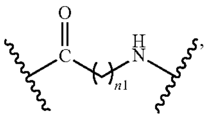, and

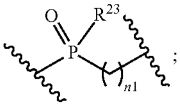;

A is $CR^{17}$ or N, wherein $R^{17}$ is selected from the group consisting of a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from the group consisting of a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group;

A is C when ------ is a double bond;

$R^5$ and one of $R^{6a}$ or $R^{6b}$ is absent when ------ is a double bond;

$R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ are each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, —$(CH_2)_{n1}R^{23}$, —$(CH_2)_{n1}OR^{23}$, —$(CH_2)_{n1}SR^{23}$, —$(CH_2)_{n1}C(O)R^{23}$, —$(CH_2)_{n1}C(O)OR^{23}$, —$(CH_2)_{n1}S(O)_{m1}R^{23}$, —$(CH_2)_{n1}NR^{23}R^{24}$, —$(CH_2)_{n1}C(O)NR^{23}R^{24}$, —$(CH_2)_{n1}NR^{23}C(O)R^{24}$, or —$(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$;

or any two adjacent or non-adjacent groups of $R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ may form a cycloalkyl group, a heteroalkyl group, an aryl group, and a heteroaryl group, wherein the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$; and $R^{22}$, $R^{23}$, $R^{24}$, $R^{25}$, and $R^{26}$ are each independently selected from a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group;

provided that:

when m is 0;

Z is $-CH_2-$;

W is

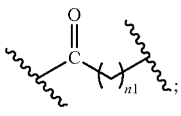;

$n_1$ is 0; and either $R^{15a}$ or $R^{15b}$ is not —H.

In some embodiments, the compound is a compound of Formula IV-A or IV-B:

(IV-A)

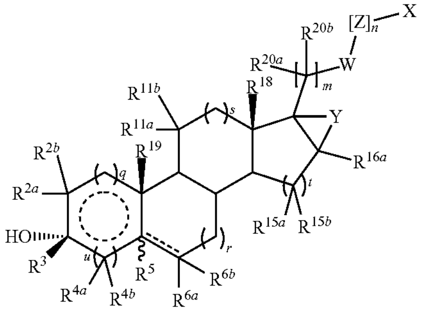

or (IV-B)

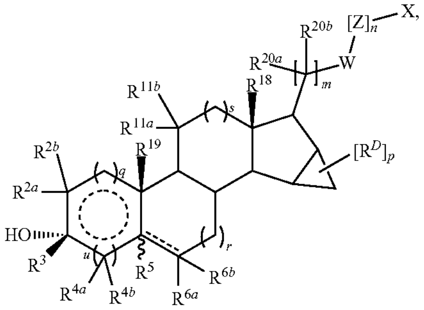

or a pharmaceutically acceptable salt thereof;

wherein:

m is 0, 1, 2, or 3;

$m_1$ is 0, 1, or 2;

n is 1 or 2;

$n_1$ is 0, 1, 2, 3, 4 or 5;

p is 0, 1, 2, 3 or 4;

q is independently 0, 1, 2, or 3;

r is independently 0, 1 or 2;

s is independently 0, 1 or 2;

t is independently 0, 1, 2 or 3;

u is independently 1 or 2;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-SR^{A1}$, $-N(R^{A1})_2$, $-OC(=O)R^{A1}$, $-OC(=O)OR^{A1}$, $-OC(=O)SR^{A1}$, $-OC(=O)N(R^{A1})_2$, $-SC(=O)R^{A2}$, $-SC(=O)OR^{A1}$, $-SC(=O)SR^{A1}$, $-SC(=O)N(R^{A1})_2$, $-NHC(=O)R^{A1}$, $-NHC(=O)OR^{A1}$, $-NHC(=O)SR^{A1}$, $-NHC(=O)N(R^{A1})_2$, $-OS(=O)_2R^{A2}$, $-OS(=O)_2OR^{A1}$, $-S-S(=O)_2R^{A2}$, $-S-S(=O)_2OR^{A1}$, $-S(=O)R^{A2}$, $-SO_2R^{A2}$, or $-S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

Z is each independently selected from $-CR^{23}R^{24}-$, $-NR^{23}-$, or $-O-$;

W is each independently selected from $-S(CH_2)_{n1}-$,

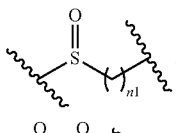
,
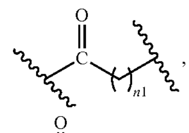
,
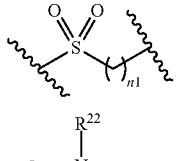
,
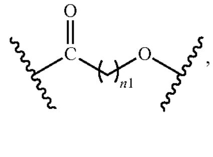
,
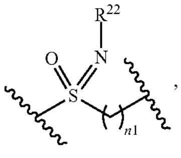
,
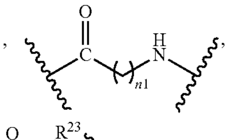
, and
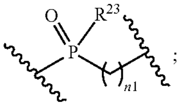
;

Y is $-C(R^{23})_2-$ or $-O-$;

$R^D$ is each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, $-(CH_2)_{n1}R^{23}$, $-(CH_2)_{n1}OR^{23}$, $-(CH_2)_{n1}SR^{23}$, $-(CH_2)_{n1}C(O)R^{23}$, $-(CH_2)_{n1}C(O)OR^{23}$, $-(CH_2)_{n1}S(O)_{m1}R^{23}$, $-(CH_2)_{n1}S(O)(NR^{23})R^{24}$, $-(CH_2)_{n1}NR^{23}R^{24}$, $-(CH_2)_{n1}C(O)NR^{23}R^{24}$, $-(CH_2)_{n1}NR^{23}C(O)R^{24}$ or $-(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a cycloalkyl group, a heterocyclic group, an aryl group, a heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$;

$R^5$ and one of $R^{6a}$ or $R^{6b}$ is absent when ------ is a double bond;

$R^3$, $R^{2a}$, $R^{2b}$, $R^{4a}$, $R^{4b}$, $R^5$, $R^{6a}$, $R^{6b}$, $R^{11a}$, $R^{11b}$, $R^{15a}$, $R^{15b}$, $R^{16a}$, $R^{16b}$, $R^{18}$, $R^{19}$, $R^{20a}$, or $R^{20b}$ are each independently selected from the group consisting of a hydrogen atom, a deuterium atom, an alkyl group, a deuterated alkyl group, an alkoxy group, a halogenated alkoxy group, a halogen, an amino group, a mercapto group, a nitro group, a hydroxyl group, a cyano group, an alkenyl group, an alkynyl group, a cycloalkyl group, a heterocyclyl group, an aryl group, a heteroaryl group, $-(CH_2)_{n1}R^{23}$, $-(CH_2)_{n1}OR^{23}$, $-(CH_2)_{n1}SR^{23}$, $-(CH_2)_{n1}C(O)R^{23}$, $-(CH_2)_{n1}C(O)OR^{23}$, $-(CH_2)_{n1}S(O)_{m1}R^{23}$, $-(CH_2)_{n1}NR^{23}R^{24}$, $-(CH_2)_{n1}C(O)NR^{23}R^{24}$, $-(CH_2)_{n1}NR^{23}C(O)R^{24}$, or $-(CH_2)_{n1}NR^{23}S(O)_{m1}R^{24}$, wherein the alkyl group, the haloalkyl group, the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$;

or any two adjacent or non-adjacent groups of $R^3$, $R^{2a}$, $R^{2b}$, $R^{4a}$, $R^{4b}$, $R^5$, $R^{6a}$, $R^{6b}$, $R^{11a}$, $R^{11}$, $R^{15a}$, $R^{15b}$, $R^{16a}$, $R^{16b}$, $R^{18}$, $R^{19}$, $R^{20a}$, or $R^{20b}$ may form a cycloalkyl group, a heteroalkyl group, an aryl group, and a heteroaryl group, wherein the cycloalkyl group, the heterocyclic group, the aryl group and the heteroaryl group are optionally further substituted by one or more of the substituent groups selected from the group consisting of a deuterium atom, an alkyl group, a halogen, an amino group, a mercapto group, an oxo group, a nitro group, a cyano group, a hydroxyl group, an alkenyl group, an alkynyl group, an alkoxy group, a halogenated alkoxy group, a hydroxyalkyl group, a substituted or unsubstituted cycloalkyl group, a substituted or unsubstituted heterocyclic group, a substituted or unsubstituted aryl group, a substituted or unsubstituted heteroaryl group, $-(CH_2)_{n1}R^{25}$, $-(CH_2)_{n1}OR^{25}$, $-(CH_2)_{n1}SR^{25}$, $-(CH_2)_{n1}C(O)R^{25}$, $-(CH_2)_{n1}C(O)OR^{25}$, $-(CH_2)_{n1}S(O)_{m1}R^{25}$, $-(CH_2)_{n1}NR^{25}R^{26}$, $-(CH_2)_{n1}C(O)NR^{25}R^{26}$, $-(CH_2)_{n1}C(O)NHR^{25}$, $-(CH_2)_{n1}NR^{25}C(O)R^{26}$, and $-(CH_2)_{n1}NR^{25}S(O)_{m1}R^{26}$;

or $R^{15a}$ and $R^{15b}$, or $R^{16a}$ and $R^{16b}$ are joined to form an oxo (=O) group;

or one of $R^{15a}$ or $R^{15b}$, and one of $R^{16a}$ or $R^{16b}$ are absent so as to form a double bond; and $R^{22}$, $R^{23}$, $R^{24}$, $R^{25}$, and $R^{26}$ are each independently selected from a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group.

In some embodiments, the compound is a compound of Formula IV-C or Formula IV-D:

(IV-C)

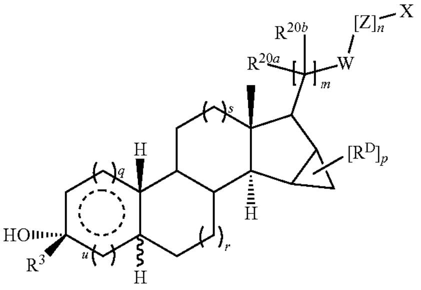

or (IV-D)

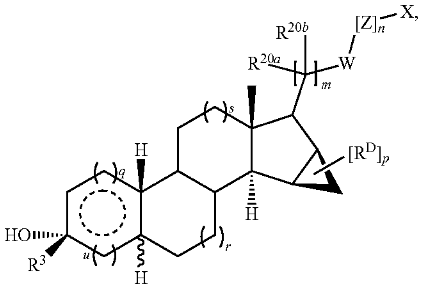

or a pharmaceutically acceptable salt thereof.

In some embodiments, the compound is a compound of Formula IV-E:

(IV-E)

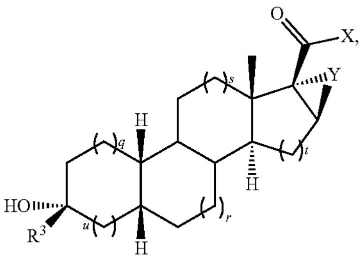

or a pharmaceutically acceptable salt thereof.

In some embodiments, the compound is a compound of Formula I-A:

(I-A)

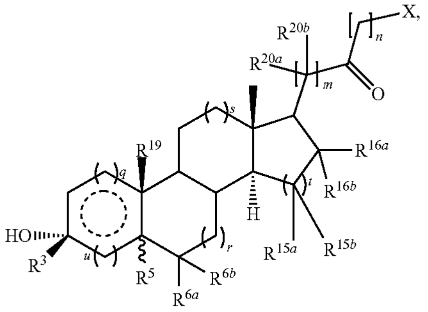

or a pharmaceutically acceptable salt thereof.

In some embodiments, the compound is a compound of Formula I-B:

(I-B)

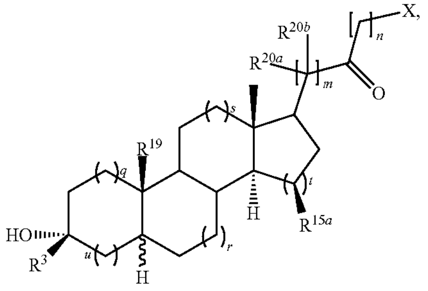

or a pharmaceutically acceptable salt thereof.

In some embodiments, the compound is a compound of Formula I-C:

(I-C)

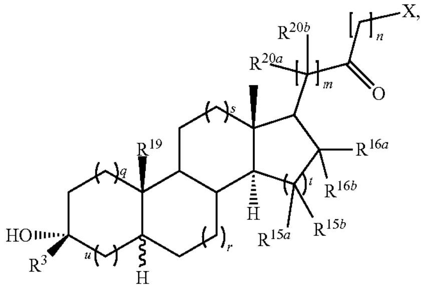

or a pharmaceutically acceptable salt thereof.

In some embodiments, the compound is a compound of Formula I-D:

(I-D)

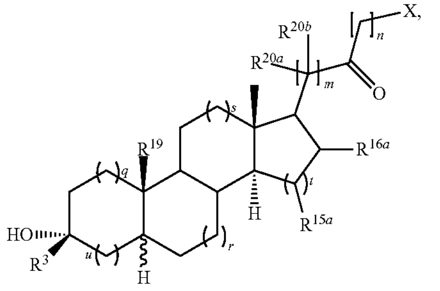

or a pharmaceutically acceptable salt thereof.

In some embodiments, the compound is a compound of Formula I-E:

(I-E)

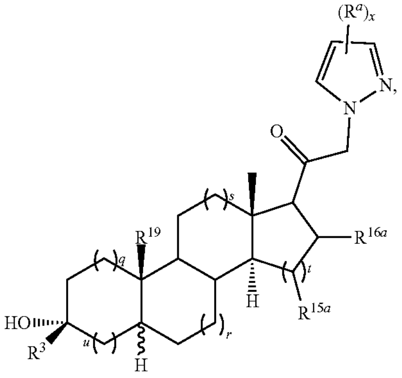

or a pharmaceutically acceptable salt thereof.

In some embodiments, the compound is a compound of Formula I-F:

(I-F)

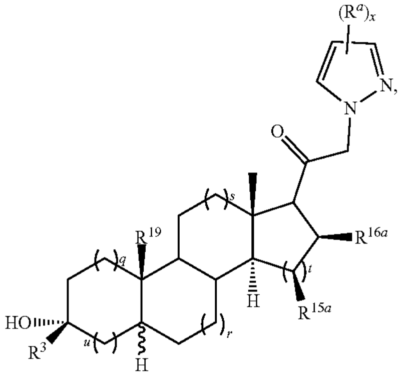

or a pharmaceutically acceptable salt thereof.

In some embodiments, the compound is a compound of Formula I-G:

(I-G)

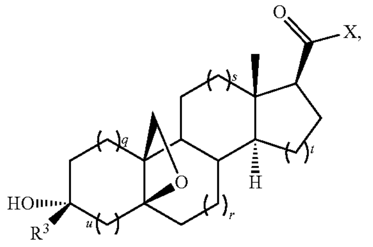

or a pharmaceutically acceptable salt thereof.

In some embodiments, the compound is a compound of Formula I-H:

(I-H)

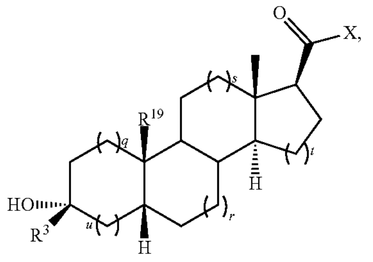

or a pharmaceutically acceptable salt thereof.

In some embodiments, the compound is a compound of Formula V:

(V)

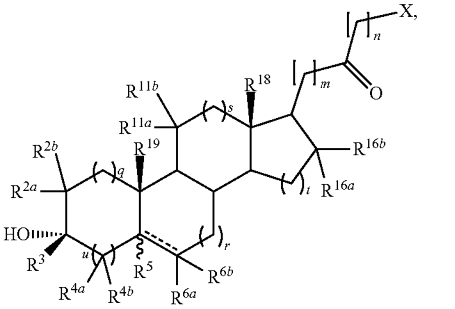

or a pharmaceutically acceptable salt thereof;

wherein:

m is 0, 1, 2, or 3;

n is 1 or 2;

q is independently 0, 1, 2, or 3;

r is independently 0, 1 or 2;

s is independently 0, 1 or 2;

t is independently 0, 1, 2 or 3;

u is independently 1 or 2;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $—OR^{A1}$, $—SR^{A1}$, $—N(R^{A1})_2$, $—OC(═O)R^{A1}$, $—OC(═O)OR^{A1}$, $—OC(═O)SR^{A1}$, $—OC(═O)N(R^{A1})_2$, $—SC(═O)R^{A2}$, $—SC(═O)OR^{A1}$, $—SC(═O)SR^{A1}$, $—SC(═O)N(R^{A1})_2$, $—NHC(═O)R^{A1}$, $—NHC(═O)OR^{A1}$, $—NHC(═O)SR^{A1}$, —NHC(═O)N($R^{A1}$)$_2$, —OS(═O)$_2$R$^{A2}$, —OS(═O)$_2$OR$^{A1}$, —S—S(═O)$_2$R$^{A2}$, —S—S(═O)$_2$OR$^{A1}$, —S(═O)R$^{A2}$, —SO$_2$R$^{A2}$, or —S(═O)$_2$OR$^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, or a nitrogen protecting group when attached to a nitrogen atom; and each instance of $R^{A2}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^5$ is hydrogen or methyl, or when ------ is a double bond, $R^5$ and one of $R^{6a}$ or $R^{6b}$ is absent;

$R^{19}$ is hydrogen or substituted or unsubstituted alkyl;

$R^{18}$ is substituted or unsubstituted alkyl, substituted or unsubstituted alkenyl, or substituted or unsubstituted alkynyl;

$R^3$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each of $R^{6a}$ and $R^{6b}$ is independently hydrogen, halogen, cyano, hydroxyl, substituted or unsubstituted alkyl, substituted or unsubstituted alkenyl, or substituted or unsubstituted alkynyl; or $R^{6a}$ and $R^b$ are joined to form an oxo (═O) group; and each of $R^{2a}$, $R^{2b}$, $R^{4a}$, $R^4$, $R^{11a}$, $R^{11b}$, $R^{16a}$, or $R^{16b}$ is independently hydrogen, halogen, cyano, hydroxyl, substituted or unsubstituted alkyl, substituted or unsubstituted alkenyl, substituted or unsubstituted heterocyclyl, substituted or unsubstituted alkynyl, —OR$^{D1}$, —OC(═O)R$^{D1}$, —NH$_2$, —N(R$^{D1}$)$_2$, or —NR$^{D1}$C(═O)R$^{D1}$, wherein each instance of $R^{D1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a nitrogen protecting group when attached to a nitrogen atom, or two $R^{D1}$ groups are joined to form an substituted or unsubstituted heterocyclic ring; or any one of $R^{2a}$ and $R^{2b}$, or $R^{4a}$ and $R^{4b}$, or $R^{11a}$ and $R^{11b}$ or $R^{16a}$ and $R^{16b}$ are joined to form an oxo (═O) group;

provided that:

q, s, r, u, and t are not simultaneously 1.

In some embodiments, the compound is a compound of Formula VI:

(VI)

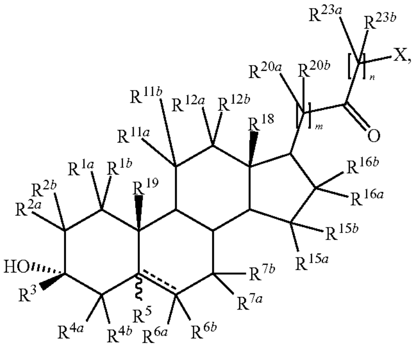

or a pharmaceutically acceptable salt thereof;

wherein:

m is 0, 1, 2, 3, or 4;

n is 0, 1, 2, 3, or 4;

provided that when m is 0, n is not 0 or 1;

X is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each of $R^{1a}$, $R^{1b}$, $R^{2a}$, $R^{2b}$, $R^{4a}$, $R^{4b}$, $R^{7a}$, $R^{7b}$, $R^{11a}$, $R^{11b}$, $R^{12a}$, $R^{12b}$, $R^{15a}$, $R^{15b}$, $R^{16a}$, and $R^{16b}$ is independently hydrogen, halogen, cyano, —NO$_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —C(═O)R$^{A1}$, —C(═O)OR$^{A1}$, —C(═O)SR$^{A1}$, —C(═O)N(R$^{A1}$)$_2$, —OC(═O)R$^{A1}$, —OC(═O)OR$^{A1}$, —OC(═O)N(R$^{A1}$)$_2$, —OC(═O)SR$^{A1}$, —OS(═O)$_2$R$^{A1}$, —OS(═O)$_2$OR$^{A1}$, —OS(═O)$_2$N(R$^{A1}$)$_2$, —N(R$^{A1}$)C(═O)R$^{A1}$, —N(R$^{A1}$)C(═NR$^{A1}$)R$^{A1}$, —N(R$^{A1}$)C(═O)OR$^{A1}$, —N(R$^{A1}$)C(═O)N(R$^{A1}$)$_2$, —N(R$^{A1}$)C(═NR$^{A1}$) N(R$^{A1}$)$_2$, —N(R$^{A1}$)S(═O)$_2$R$^{A1}$, —N(R$^{A1}$)S(═O)$_2$OR$^{A1}$, —N(R$^{A1}$)S(═O)$_2$N(R$^{A1}$)$_2$, —SC(═O)R$^{A1}$, —SC(═O)OR$^{A1}$, —SC(═O)SR$^{A1}$, —SC(═O)N(R$^{A1}$)$_2$, —S(═O)$_2$R$^{A1}$, —S(═O)$_2$OR$^{A1}$, or —S(═O)$_2$N(R$^{A1}$)$_2$, wherein each instance of $R^{A1}$ is independently selected from hydrogen, substituted or unsubstituted alkyl, substituted or unsubstituted alkenyl, substituted or unsubstituted alkynyl, substituted or unsubstituted carbocyclyl, or substituted or unsubstituted heterocyclyl, substituted or unsubstituted aryl, substituted or unsubstituted heteroaryl, an oxygen protecting group when attached to oxygen, a nitrogen protecting group when attached to nitrogen, or a sulfur protecting group when attached to sulfur; or $R^{11a}$ and $R^{11b}$ are joined to form an oxo (═O) group; or $R^{12a}$ and $R^{12b}$ are joined to form an oxo (═O) group; or $R^{15a}$ and $R^{15b}$ are joined to form an oxo (═O) group; or $R^{16a}$ and $R^{16b}$ are joined to form an oxo (═O) group; or $R^{4a}$ and $R^{4b}$ are joined to form an oxo (═O) group; or $R^{7a}$ and $R^{7b}$ are joined to form an oxo (═O) group; or $R^{2a}$ and $R^{2b}$ are joined to form an oxo (═O) group; or $R^{1a}$ and $R^{1b}$ are joined to form an oxo (═O) group;

$R^3$ is hydrogen, substituted or unsubstituted alkyl;

$R^5$ is hydrogen or methyl;

each of $R^{6a}$ and $R^{6b}$ is independently hydrogen, halogen, cyano, —$NO_2$, —OH, substituted or unsubstituted alkyl, substituted or unsubstituted alkenyl, or substituted or unsubstituted alkynyl; or $R^{6a}$ and $R^{6b}$ are joined to form an oxo (=O) group;

$R^{18}$ is substituted or unsubstituted alkyl, substituted or unsubstituted alkenyl, or substituted or unsubstituted alkynyl;

$R^{19}$ is hydrogen or substituted or unsubstituted alkyl;

and $R^{20a}$, $R^{20b}$, $R^{23a}$, or $R^{23b}$ are each independently selected from the group consisting of a hydrogen atom, an alkyl group, a halogenated alkyl group, an alkoxy group, a halogenated alkoxy group.

In some embodiments, ------ is a single bond. In another embodiment, ------ is a double bond.

In some embodiments, the compound is a compound of Formula VII:

(VII)

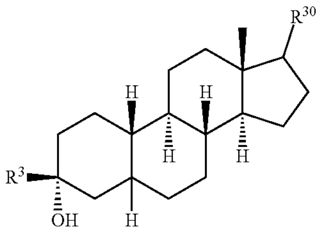

or a pharmaceutically acceptable salt thereof, wherein $R^3$ is $C_{1-6}$ alkyl or $C_{1-6}$ alkoxyalkyl; and $R^{30}$ is

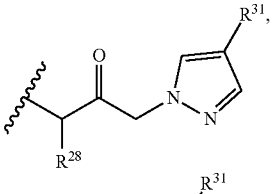

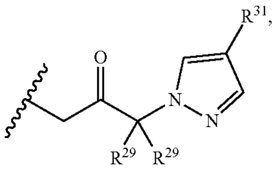

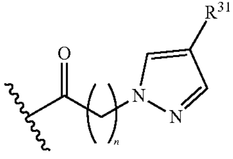

, or

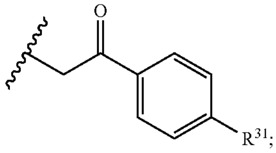

$R^{28}$ is —H or unsubstituted $C_{1-3}$ alkyl;

Each $R^{29}$ is independently —H or unsubstituted $C_{1-3}$ alkyl;

$R^{31}$ is —OH, —CN, or —$CF_3$; and n is 2, 3, or 4.

In some embodiments, $R^{30}$ is

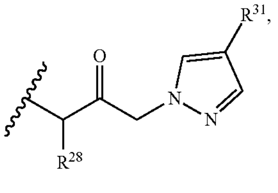

and $R^{28}$ is —H or —$CH_3$. In some of embodiments, $R^{31}$ is —CN.

In some embodiments, $R^{30}$ is

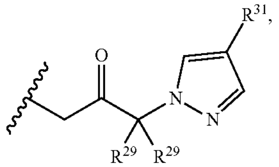

and each $R^{29}$ is independently —H or —$CH_3$. In some of embodiments, each $R^{29}$ is —$CH_3$. In some of embodiments, one instance of $R^{29}$ is —$CH_3$. And, in some embodiments, each $R^{29}$ is —H. In other embodiments, $R^{31}$ is —CN.

In some embodiments, $R^{30}$ is

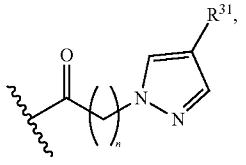

n is 2 or 3, and $R^{31}$ is —CN.

In some embodiments, $R^3$ is unsubstituted $C_{1-3}$ alkyl or unsubstituted $C_{1-3}$ alkyl-O—$C_{1-3}$ alkyl.

In some embodiments, the compound of Formula (I) is a compound is of Formula (I-A), Formula (I-B), Formula (I-C), Formula (I-D), Formula (I-E), Formula (I-F), Formula (I-G), Formula (I-H), or Formula (VII). In some embodiments, the compound of Formula (IV-A) or (IV-A) is a compound is of Formula (IV-C), Formula (IV-D), or Formula (IV-E). In some embodiments, the compound of Formula (VI) is a compound is of Formula (VI-A), Formula (VI-B), Formula (VI-C), Formula (VI-D), Formula (VI-E), Formula (VI-F), Formula (VI-G), Formula (VI-H), Formula (VI-IA).

A. Groups $R^{1a}$ and $R^{1b}$

In some embodiments, $R^{1a}$ and $R^{1b}$ are each independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl.

In some embodiments, $R^{1a}$ and $R^{1b}$ are each independently hydrogen, substituted or unsubstituted carbocyclyl, substituted or unsubstituted heterocyclyl, substituted or unsubstituted aryl, substituted or unsubstituted heteroaryl.

In some embodiments, $R^{1a}$ and $R^{1b}$ are each independently substituted carbocyclyl, substituted heterocyclyl, substituted aryl, or substituted heteroaryl, wherein each is further substituted with substituted carbocyclyl, substituted heterocyclyl, substituted aryl, or substituted heteroaryl.

In some embodiments, $R^{1a}$ and $R^{1b}$ are each independently selected from the group consisting of:

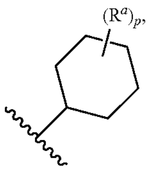

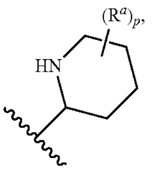

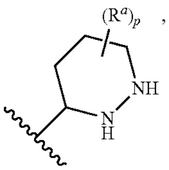

,

-continued

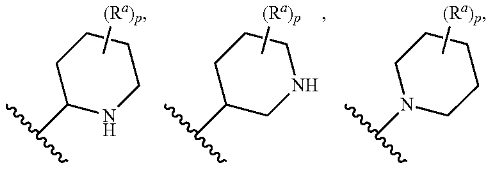

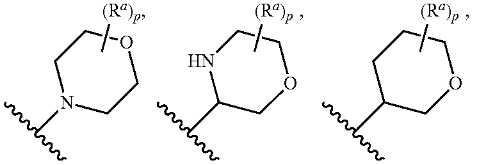

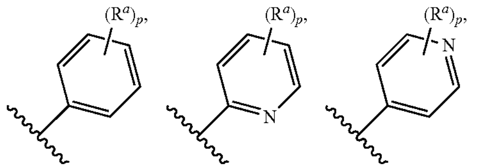

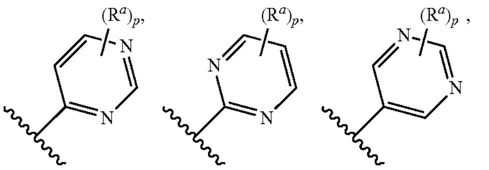

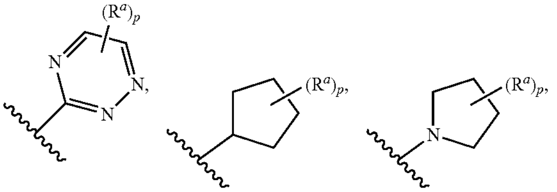

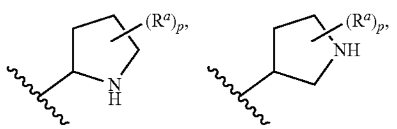

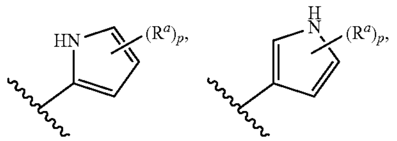

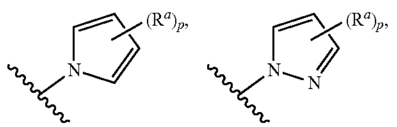

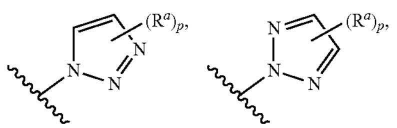

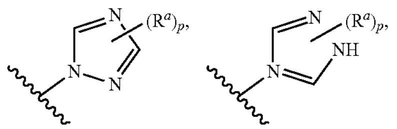

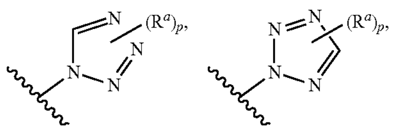

-continued

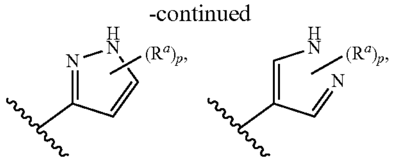

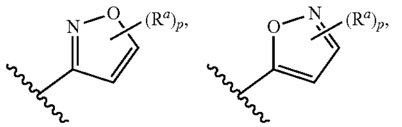

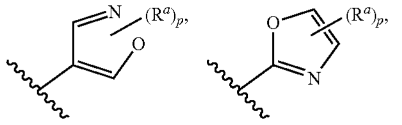

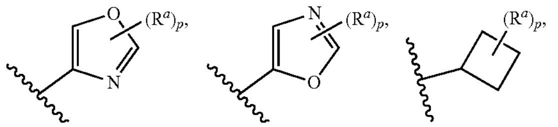

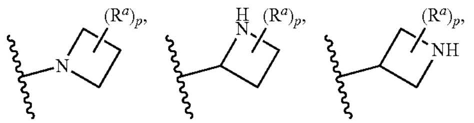

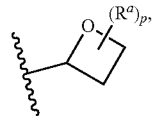

and

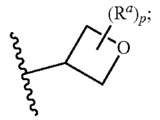

wherein:

each instance of $R^a$ is independently hydrogen, halogen, $—NO_2$, —CN, $—OR^{A1}$, $—OC(=O)R^{A1}$, $—OS(=O)_2OR^{A1}$, $—N(R^{A1})_2$, or $—N(R^{A1})C(=O)R^{A1}$, $—N(R^{A1})S(=O)_2R^{A1}$, $—N(R^{A1})S(=O)_2OR^{A1}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl;

each instance of $R^{A1}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl, an oxygen protecting group when attached to oxygen, a nitrogen protecting group when attached to nitrogen, or two $R^{A1}$ groups are taken with the intervening atoms to form a substituted or unsubstituted heterocyclic ring; and p is an integer selected from 0 to 11.

In some embodiments, $R^{1a}$ and $R^{1b}$ are each independently selected from the group consisting of:

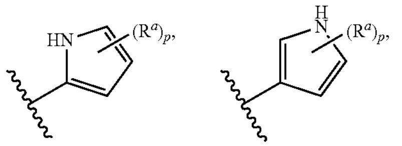

-continued

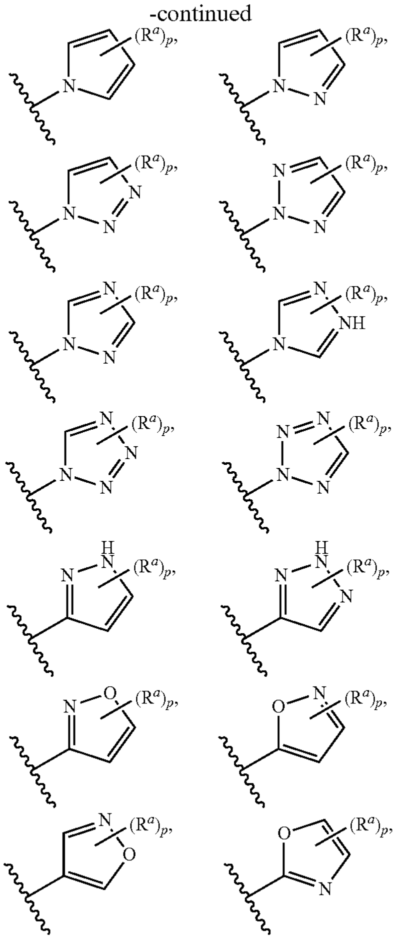

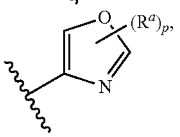

and

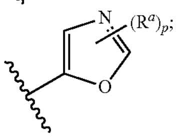

wherein:

each instance of $R^a$ is independently hydrogen, halogen, $—NO_2$, —CN, $—OR^{A1}$, $—OC(=O)R^{A1}$, $—OS(=O)_2OR^{A1}$, $—N(R^{A1})_2$, or $—N(R^{A1})C(=O)R^{A1}$, $—N(R^{A1})S(=O)_2R^{A1}$, $—N(R^{A1})S(=O)_2OR^{A1}$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl;

each instance of $R^{A1}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocyclyl, substituted or unsubstituted 3- to 6-membered heterocyclyl, substituted or unsubstituted $C_{5-10}$ aryl, substituted or unsubstituted 5- to 10-membered heteroaryl, an oxygen protecting group when attached to oxygen, a nitrogen protecting group when attached to nitrogen, or two $R^{A1}$ groups are taken with the intervening atoms to form a substituted or unsubstituted heterocyclic ring; and p is an integer selected from 0 to 11.

In some embodiments, $R^{1a}$ and $R^{1b}$ are both hydrogen.

B. Groups $R^{2a}$ and $R^{2b}$

In some embodiments, $R^{2a}$ and $R^{2b}$ are each independently hydrogen, halogen, —CN, $—NO_2$, substituted or unsubstituted alkyl, substituted or unsubstituted alkenyl, substituted or unsubstituted alkynyl, $—OR^{A1}$, $—OC(=O)R^{A1}$, $—OS(=O)_2OR^{A1}$, $—N(R^{A1})_2$, or $—N(R^{A1})C(=O)R^{A1}$, $—N(R^{A1})S(=O)_2R^{A1}$, $—N(R^{A1})S(=O)_2OR^{A1}$; wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{A1}$ groups are taken with the intervening atoms to form a substituted or unsubstituted heterocyclic ring.

In some embodiments, $R^{2a}$ and $R^{2b}$ are each independently hydrogen, halogen, —CN, $—NO_2$, $—OR^{A1}$, $—OC(=O)R^{A1}$, $—N(R^{A1})_2$, or $—N(R^{A1})C(=O)R^{A1}$; wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{A1}$ groups are taken with the intervening atoms to form a substituted or unsubstituted heterocyclic ring.

In some embodiments, $R^{2a}$ and $R^{2b}$ are independently hydrogen, —OH, or substituted or unsubstituted $C_{1-6}$ alkyl.

In some embodiments, each of $R^{2a}$ and $R^{2b}$ are independently —H, —OH, $C_{1-6}$ alkyl, $C_{1-6}$ haloalkyl, $C_{1-6}$ alkoxy, or $C_{1-6}$ haloalkoxy.

In some embodiments, $R^{2a}$ and $R^{2b}$ are independently $—CH_3$, $—CH_2CH_3$, —OH, $—OCH_3$, or $—CH(CH_3)_2$.

In some embodiments, $R^{2a}$ and $R^{2b}$ are both hydrogen.

In some embodiments, $R^{2a}$ and $R^{2b}$ are joined to form an oxo (=O) group.

C. Group $R^3$

In some embodiments, $R^3$ is substituted or unsubstituted alkyl. In some embodiments, $R^3$ is substituted alkyl. In some embodiments, $R^3$ is unsubstituted alkyl.

In some embodiments, $R^3$ is substituted or unsubstituted $C_{1-6}$ alkyl. In some embodiments, $R^3$ is substituted $C_{1-6}$ alkyl. In some embodiments, $R^3$ is unsubstituted $C_{1-6}$ alkyl.

In some embodiments, $R^3$ is substituted or unsubstituted $C_{2-6}$ alkyl. In some embodiments, $R^3$ is substituted $C_{2-6}$ alkyl. In some embodiments, $R^3$ is unsubstituted $C_{2-6}$ alkyl.

In some embodiments, $R^3$ is methyl, ethyl, n-propyl, iso-propyl, n-butyl, iso-butyl. In some embodiments, $R^3$ is methyl. In some embodiments, $R^3$ is ethyl. In some embodiments, $R^3$ is propyl. In some embodiments, $R^3$ is n-butyl. In some embodiments, $R^3$ is substituted methyl. In some embodiments, $R^3$ is unsubstituted methyl. In some embodiments, $R^3$ is substituted ethyl. In some embodiments, $R^3$ is unsubstituted ethyl.

In some embodiments, $R^3$ is $—CH_2C_3H_5$.

In some embodiments, $R^3$ is $C_{1-6}$ alkoxy.

In some embodiments, $R^3$ is $—CH_2OCH_3$. In some embodiments, $R^3$ is $—CH_2CH_2OCH_3$. In some embodiments, $R^3$ is-$CH_2CH_2CH_2OCH_3$.

In some embodiments, $R^3$ is $—CH_2OCH_2CH_3$, $—CH_2CH_2OCH_2CH_3$, or $—CH_2CH_2CH_2OCH_2CH_3$.

In some embodiments, $R^3$ is $—CH_2OCH_2CH_2CH_3$, $—CH_2CH_2OCH_2CH_2CH_3$, or $—CH_2CH_2CH_2OCH_2CH_2CH_3$.

In some embodiments, $R^3$ is hydrogen.

In some embodiments, $R^3$ is $—CH_3$.

D. Groups $R^{4a}$ and $R^{4b}$

In some embodiments, $R^{4a}$ and $R^{4b}$ is each independently hydrogen, halogen, —CN, $—NO_2$, substituted or unsubstituted alkyl, substituted or unsubstituted alkenyl, substituted or unsubstituted alkynyl, —$OR^{A1}$, —OC(═O)$R^{A1}$, —OS(═O)$_2OR^{A1}$, —$N(R^{A1})_2$, or —$N(R^{A1})$C(═O)$R^{A1}$, —$N(R^{A1})$S(═O)$_2R^{A1}$, —$N(R^{A1})$S(═O)$_2OR^{A1}$; wherein each instance of $R^{E5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{A1}$ groups are taken with the intervening atoms to form a substituted or unsubstituted heterocyclic ring.

In some embodiments, $R^{4a}$ and $R^{4b}$ are each independently —H, halogen, —CN, —$NO_2$, —$OR^{A1}$, —OC(═O)$R^{A1}$, —$N(R^{A1})_2$, or —$N(R^{A1})$C(═O)$R^{A1}$; wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{A1}$ groups are taken with the intervening atoms to form a substituted or unsubstituted heterocyclic ring.

In some embodiments, $R^{4a}$ and $R^{4b}$ are each independently —H, —OH, or substituted or unsubstituted $C_{1-6}$ alkyl.

In some embodiments, each of $R^{4a}$ and $R^{4b}$ is independently —H, —OH, $C_{1-6}$ alkyl, $C_{1-6}$ haloalkyl, $C_{1-6}$ alkoxy, or $C_{1-6}$ haloalkoxy.

In some embodiments, $R^{4a}$ and $R^{4b}$ are each independently —$CH_3$, —$CH_2CH_3$, —OH, —$OCH_3$, or —$CH(CH_3)_2$.

In some embodiments, $R^{4a}$ and $R^{4b}$ are both —H.

In some embodiments, $R^{4a}$ and $R^{4b}$ are joined to form an oxo (═O) group.

E. Group $R^5$

In some embodiments, $R^5$ is —H. In some embodiments, $R^5$ is methyl.

In some embodiments, $R^5$ is hydrogen or methyl in the cis position, relative to $R^{19}$ or in the trans position, relative to $R^{19}$.

In some embodiments, $R^5$ is hydrogen in the cis position, relative to $R^{19}$ or in the trans position, relative to $R^{19}$. In some embodiments, $R^5$ is hydrogen in the cis position, relative to $R^{19}$. In some embodiments, $R^5$ is hydrogen in the trans position, relative to $R^{19}$.

In some embodiments, $R^5$ is methyl in the cis position, relative to $R^{19}$ or in the trans position, relative to $R^{19}$. In some embodiments, $R^5$ is methyl in the cis position, relative to $R^{19}$. In some embodiments, $R^5$ is methyl in the trans position, relative to $R^{19}$.

F. Groups $R^{6a}$ and $R^{6b}$

In some embodiments, $R^{6a}$ and $R^{6b}$ are each independently —H, halogen, substituted or unsubstituted alkyl, substituted or unsubstituted alkenyl, or substituted or unsubstituted alkynyl.

In some embodiments, each of $R^{6a}$ and $R^{6b}$ is independently —H or substituted alkyl.

In some embodiments, each of $R^{6a}$ and $R^{6b}$ is independently —H or unsubstituted alkyl.

In some embodiments, $R^{6a}$ is halogen or alkyl and $R^{6b}$ is —H.

In some embodiments, $R^{6a}$ and $R^{6b}$ are both halogen.

In some embodiments, $R^{6a}$ and $R^{6b}$ are both unsubstituted alkyl.

In some embodiments, $R^{6a}$ is hydrogen and $R^{6b}$ is absent.

In some embodiments, $R^{6a}$ and $R^{6b}$ are both —H.

G. Groups $R^{7a}$ and $R^{7b}$

In some embodiments, each of $R^{7a}$ and $R^{7b}$ is independently —H, halogen, —CN, —$NO_2$, substituted or unsubstituted alkyl, substituted or unsubstituted alkenyl, substituted or unsubstituted alkynyl, —$OR^{A1}$, —OC(═O)$R^{A1}$, —OS(═O)$_2OR^{A1}$, —$N(R^{A1})_2$, or —$N(R^{A1})$C(═O)$R^{A1}$, —$N(R^{A1})$S(═O)$_2R^{A1}$, —$N(R^{A1})$S(═O)$_2OR^{A1}$; wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{A1}$ groups are taken with the intervening atoms to form a substituted or unsubstituted heterocyclic ring.

In some embodiments, each of $R^{7a}$ and $R^{7b}$ is independently —H, halogen, —CN, —$NO_2$, —$OR^{A1}$, —OC(═O)$R^{A1}$, —$N(R^{A1})_2$, or —$N(R^{A1})$C(═O)$R^{A1}$; wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{A1}$ groups are taken with the intervening atoms to form a substituted or unsubstituted heterocyclic ring.

In some embodiments, each of $R^{7a}$ and $R^{7b}$ is independently —H, —OH, or substituted or unsubstituted $C_{1-6}$ alkyl.

In some embodiments, each of $R^{7a}$ and $R^{7b}$ is independently —H, —OH, $C_{1-6}$ alkyl, $C_{1-6}$ haloalkyl, $C_{1-6}$ alkoxy, or $C_{1-6}$ haloalkoxy.

In some embodiments, each of $R^{7a}$ and $R^{7b}$ is independently —$CH_3$, —$CH_2CH_3$, —OH, —$OCH_3$, or —$CH(CH_3)_2$.

In some embodiments, $R^{7a}$ and $R^{7b}$ are both —H.

In some embodiments, $R^{7a}$ and $R^{7b}$ are joined to form an oxo (═O) group.

H. Groups $R^{11a}$ and $R^{11b}$

In some embodiments, each of $R^{11a}$ and $R^{11b}$ is independently —H, halogen, —CN, —$NO_2$, substituted or unsubstituted alkyl, substituted or unsubstituted alkenyl, substituted or unsubstituted alkynyl, —$OR^{A1}$, —OC(═O)$R^{A1}$, —OS(═O)$_2OR^{A1}$, —$N(R^{A1})_2$, or —$N(R^{A1})$C(═O)$R^{A1}$, —$N(R^{A1})$S(═O)$_2R^{A1}$, —$N(R^{A1})$S(═O)$_2OR^{A1}$; wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{A1}$ groups are taken with the intervening atoms to form a substituted or unsubstituted heterocyclic ring.

In some embodiments, each of $R^{11a}$ and $R^{11b}$ is independently —H, halogen, —CN, —$NO_2$, —$OR^{A1}$, —OC(═O)$R^{A1}$, —$N(R^{A1})_2$, or —$N(R^{A1})$C(═O)$R^{A1}$; wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{A1}$ groups are taken with the intervening atoms to form a substituted or unsubstituted heterocyclic ring.

In some embodiments, each of $R^{11a}$ and $R^{11b}$ is independently —H, —OH, or substituted or unsubstituted $C_{1-6}$ alkyl.

In some embodiments, each of $R^{11a}$ and $R^{11b}$ is independently —H, —OH, $C_{1-6}$ alkyl, $C_{1-6}$ haloalkyl, $C_{1-6}$ alkoxy, or $C_{1-6}$ haloalkoxy.

In some embodiments, each of $R^{11a}$ and $R^{11b}$ is independently hydrogen, —OH, or $R^{11a}$ and $R^{11b}$ are joined to form an oxo (═O) group.

In some embodiments, each of $R^{11a}$ and $R^{11b}$ is independently —$CH_3$, —$CH_2CH_3$, —OH, —$OCH_3$, or —$CH(CH_3)_2$.

In some embodiments, $R^{11a}$ and $R^{11b}$ are both hydrogen.

In some embodiments, $R^{11a}$ and $R^{11b}$ are joined to form an oxo (=O) group.

I. Groups $R^{12a}$ and $R^{12b}$

In some embodiments, each of $R^{12a}$ and $R^{12b}$ is independently —H, halogen, —CN, —$NO_2$, substituted or unsubstituted alkyl, substituted or unsubstituted alkenyl, substituted or unsubstituted alkynyl, —$OR^{A1}$, —OC(=O)$R^{A1}$, —OS(=O)$_2$$OR^{A1}$, —N($R^{A1}$)$_2$, or —N($R^{A1}$)C(=O)$R^{A1}$, —N($R^{A1}$)S(=O)$_2$$R^{A1}$, —N($R^{A1}$)S(=O)$_2$$OR^{A1}$; wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{A1}$ groups are taken with the intervening atoms to form a substituted or unsubstituted heterocyclic ring.

In some embodiments, each of $R^{12a}$ and $R^{12b}$ is independently —H, halogen, —CN, —$NO_2$, —$OR^{A1}$, —OC(=O)$R^{A1}$, —N($R^{A1}$)$_2$, or —N($R^{A1}$)C(=O)$R^{A1}$; wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, or two $R^{A1}$ groups are taken with the intervening atoms to form a substituted or unsubstituted heterocyclic ring.

In some embodiments, each of $R^{12a}$ and $R^{12b}$ is independently —H, —OH, or substituted or unsubstituted $C_{1-6}$ alkyl.

In some embodiments, each of $R^{12a}$ and $R^{12b}$ is independently hydrogen, —OH, $C_{1-6}$ alkyl, $C_{1-6}$ haloalkyl, $C_{1-6}$ alkoxy, or $C_{1-6}$ haloalkoxy.

In some embodiments, each of $R^{12a}$ and $R^{12b}$ is independently —$CH_3$, —$CH_2CH_3$, —OH, —$OCH_3$, or —$CH(CH_3)_2$.

In some embodiments, $R^{12a}$ and $R^{12b}$ are both hydrogen.

In some embodiments, $R^{12a}$ and $R^{12b}$ are joined to form an oxo (=O) group.

J. Groups $R^{15a}$ and $R^{15b}$

In some embodiments, each of $R^{15a}$ and $R^{15b}$ is each independently —H, halogen, —CN, —$NO_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —N($R^{A1}$)$_2$, —$SR^{A1}$, —C(=O)$R^{A1}$, —C(=O)$OR^{A1}$, —C(=O)$SR^{A1}$, —C(=O)N($R^{A1}$)$_2$, —OC(=O)$R^{A1}$, —OC(=O)$OR^{A1}$, —OC(=O)N($R^{A1}$)$_2$, —OC(=O)$SR^{A1}$, —OS(=O)$_2$$R^{A1}$, —OS(=O)$_2$$OR^{A1}$, —OS(=O)$_2$N($R^{A1}$)$_2$, —N($R^{A1}$)C(=O)$R^{A1}$, —N($R^{A1}$)C(=N$R^{A1}$)$R^{A1}$, —N($R^{A1}$)C(=O)$OR^{A1}$, —N($R^{A1}$)C(=O)N($R^{A1}$)$_2$, —N($R^{A1}$)C(=N$R^{A1}$)N($R^{A1}$)$_2$, —N($R^{A1}$)S(=O)$_2$$R^{A1}$, —N($R^{A1}$)S(=O)$_2$$OR^{A1}$, —N($R^{A1}$)S(=O)$_2$N($R^{A1}$)$_2$, —SC(=O)$R^{A1}$, —SC(=O)$OR^{A1}$, —SC(=O)$SR^{A1}$, —SC(=O)N($R^{A1}$)$_2$, —S(=O)$_2$$R^{A1}$, —S(=O)$_2$$OR^{A1}$, or —S(=O)$_2$N($R^{A1}$)$_2$, wherein each instance of $R^{A1}$ is independently selected from hydrogen, substituted or unsubstituted alkyl, substituted or unsubstituted alkenyl, substituted or unsubstituted alkynyl, substituted or unsubstituted carbocyclyl, or substituted or unsubstituted heterocyclyl, substituted or unsubstituted aryl, substituted or unsubstituted heteroaryl, an oxygen protecting group when attached to oxygen, a nitrogen protecting group when attached to nitrogen, or a sulfur protecting group when attached to sulfur, or two $R^{A1}$ groups are taken with the intervening atoms to form a substituted or unsubstituted heterocyclic ring; or $R^{15a}$ and $R^{15b}$ are joined to form an oxo (=O) group.

In some embodiments, each of $R^{15a}$ and $R^{15b}$ is independently —H, halogen, —CN, substituted or unsubstituted alkyl, or substituted or unsubstituted carbocyclyl.

In some embodiments, $R^{15a}$ and $R^{15b}$ are both hydrogen. In some embodiments, $R^{15a}$ is hydrogen. In some embodiments, $R^{15b}$ is hydrogen.

In some embodiments, $R^{15a}$ and $R^{15b}$ are both substituted alkyl. In some embodiments, $R^{15a}$ and $R^{15b}$ are both unsubstituted alkyl. In some embodiments, $R^{15a}$ and $R^{15b}$ are both methyl. In some embodiments, $R^{15a}$ and $R^{15b}$ are both unsubstituted methyl. In some embodiments, $R^{15a}$ and $R^{15b}$ are both substituted methyl. In some embodiments, one of $R^{15a}$ and $R^{15b}$ is substituted methyl, and the other is unsubstituted methyl. In some embodiments, $R^{15a}$ and $R^{15b}$ are both ethyl. In some embodiments, $R^{15a}$ is unsubstituted methyl. In some embodiments, $R^{15a}$ is substituted methyl. In some embodiments, one of $R^{15a}$ and $R^{15b}$ is substituted ethyl, and the other is unsubstituted ethyl. In some embodiments, $R^{15b}$ is unsubstituted methyl. In some embodiments, $R^{15b}$ is substituted methyl.

In some embodiments, $R^{15a}$ and $R^{15b}$ are joined to form an oxo (=O) group.

In some embodiments, each of $R^{15a}$ and $R^{15b}$ is independently hydrogen, substituted or unsubstituted alkyl, or substituted or unsubstituted carbocyclyl. In some embodiments, $R^{15a}$ and $R^{15b}$ is each independently hydrogen, unsubstituted alkyl, or unsubstituted carbocyclyl. In some embodiments, $R^{15a}$ and $R^{15b}$ is each independently hydrogen, methyl, or cyclopropyl.

K. Groups $R^{16a}$ and $R^{16b}$

In some embodiments, each of $R^{16a}$ and $R^{16b}$ is each independently hydrogen, halogen, —CN, —$NO_2$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —N($R^{A1}$)$_2$, —$SR^{A1}$, —C(=O)$R^{A1}$, —C(=O)$OR^{A1}$, —C(=O)$SR^{A1}$, —C(=O)N($R^{A1}$)$_2$, —OC(=O)$R^{A1}$, —OC(=O)$OR^{A1}$, —OC(=O)N($R^{A1}$)$_2$, —OC(=O)$SR^{A1}$, —OS(=O)$_2$$R^{A1}$, —OS(=O)$_2$$OR^{A1}$, —OS(=O)$_2$N($R^{A1}$)$_2$, —N($R^{A1}$)C(=O)$R^{A1}$, —N($R^{A1}$)C(=N$R^{A1}$)$R^{A1}$, —N($R^{A1}$)C(=O)$OR^{A1}$, —N($R^{A1}$)C(=O)N($R^{A1}$)$_2$, —N($R^{A1}$)C(=N$R^{A1}$) N($R^{A1}$)$_2$, —N($R^{A1}$)S(=O)$_2$$R^{A1}$, —N($R^{A1}$)S(=O)$_2$$OR^{A1}$, —N($R^{A1}$)S(=O)$_2$N($R^{A1}$)$_2$, —SC(=O)$R^{A1}$, —SC(=O)$OR^{A1}$, —SC(=O)$SR^{A1}$, —SC(=O)N($R^{A1}$)$_2$, —S(=O)$_2$$R^{A1}$, —S(=O)$_2$$OR^{A1}$, or —S(=O)$_2$N($R^{A1}$)$_2$, wherein each instance of $R^{A1}$ is independently selected from hydrogen, substituted or unsubstituted alkyl, substituted or unsubstituted alkenyl, substituted or unsubstituted alkynyl, substituted or unsubstituted carbocyclyl, or substituted or unsubstituted heterocyclyl, substituted or unsubstituted aryl, substituted or unsubstituted heteroaryl, an oxygen protecting group when attached to oxygen, a nitrogen protecting group when attached to nitrogen, or a sulfur protecting group when attached to sulfur, or two $R^{A1}$ groups are taken with the intervening atoms to form a substituted or unsubstituted heterocyclic ring; or $R^{15a}$ and $R^{15b}$ are joined to form an oxo (=O) group.

In some embodiments, each of $R^{16a}$ and $R^{16b}$ is independently hydrogen, halogen, —CN, substituted or unsubstituted alkyl, or substituted or unsubstituted carbocyclyl.

In some embodiments, $R^{16a}$ and $R^{16b}$ are both hydrogen. In some embodiments, $R^{16a}$ is hydrogen. In some embodiments, $R^{16b}$ is hydrogen.

In some embodiments, $R^{16a}$ and $R^{16b}$ are both substituted alkyl. In some embodiments, $R^{16a}$ and $R^{16b}$ are both unsubstituted alkyl. In some embodiments, $R^{16a}$ and $R^{16b}$ are both methyl. In some embodiments, $R^{16a}$ and $R^{16b}$ are both unsubstituted methyl. In some embodiments, $R^{16a}$ and $R^{16b}$ are both substituted methyl. In some embodiments, $R^{16a}$ and $R^{16b}$ are both ethyl. In some embodiments, $R^{16a}$ is unsubstituted methyl. In some embodiments, $R^{16a}$ is substituted methyl. In some embodiments, $R^{16b}$ is unsubstituted methyl. In some embodiments, $R^{15b}$ is substituted methyl.

In some embodiments, $R^{16a}$ and $R^{16b}$ are joined to form an oxo (=O) group.

In some embodiments, each of $R^{16a}$ and $R^{16b}$ is independently hydrogen, substituted or unsubstituted alkyl, or substituted or unsubstituted carbocyclyl. In some embodiments, $R^{16a}$ and $R^{16b}$ is each independently hydrogen, unsubstituted alkyl, or unsubstituted carbocyclyl. In some embodiments, each of $R^{16a}$ and $R^{16b}$ is independently hydrogen, methyl, or cyclopropyl.

L. Group $R^{18}$

In some embodiments, $R^{18}$ is substituted alkyl. In some embodiments, $R^{18}$ is substituted $C_{1-6}$ alkyl (e.g., substituted methyl, substituted ethyl, substituted propyl, or substituted iso-propyl).

In some embodiments, $R^{18}$ is unsubstituted alkyl. In some embodiments, $R^{18}$ is unsubstituted $C_{1-6}$ alkyl (e.g., unsubstituted methyl, unsubstituted ethyl, unsubstituted propyl, or unsubstituted iso-propyl). In some embodiments, $R^{18}$ is methyl. In some embodiments, $R^{18}$ is ethyl.

In some embodiments, $R^{18}$ is unsubstituted alkenyl. In some embodiments, $R^{18}$ is unsubstituted $C_{2-6}$ alkenyl. In some embodiments, $R^{18}$ is substituted alkenyl. In some embodiments, $R^{18}$ is substituted $C_{2-4}$ alkenyl. In some embodiments, $R^{18}$ is unsubstituted alkynyl (e.g., $C_{2-6}$ alkynyl). In some embodiments, $R^{18}$ is substituted alkynyl.

M. Group $R^{19}$

In some embodiments, $R^{19}$ is hydrogen, substituted or unsubstituted alkyl, substituted or unsubstituted alkenyl, or substituted or unsubstituted alkynyl.

In some embodiments, $R^{19}$ is hydrogen or substituted or unsubstituted alkyl.

In some embodiments, $R^{19}$ is substituted alkyl.

In some embodiments, $R^{19}$ is substituted $C_{2-6}$ alkyl. In some embodiments, $R^{19}$ is unsubstituted $C_{2-6}$ alkyl.

In some embodiments, $R^{19}$ is $-CH_2OCH_3$. In some embodiments, $R^{19}$ is $-CH_2OCH_2CH_3$.

In some embodiments, $R^{19}$ is hydrogen or unsubstituted alkyl.

In some embodiments, $R^{19}$ is unsubstituted alkyl.

In some embodiments, $R^{19}$ is substituted $C_{1-6}$ alkyl. In some embodiments, $R^{19}$ is unsubstituted $C_{1-6}$ alkyl.

In some embodiments, $R^{19}$ is methyl. In some embodiments, $R^{19}$ is ethyl.

In some embodiments, $R^{19}$ is hydrogen. In some embodiments, $R^{19}$ is hydrogen or substituted or unsubstituted $C_{1-6}$ alkyl.

In some embodiments, $R^{19}$ is hydrogen, methyl, ethyl, or methoxymethyl.

N. Groups $R^{20a}$ and $R^{20b}$

In some embodiments, each of $R^{20a}$ and $R^{20b}$ is independently hydrogen or substituted alkyl. In some embodiments, $R^{20a}$ and $R^{20b}$ are independently hydrogen or unsubstituted alkyl. In some embodiments, $R^{20a}$ and $R^{20b}$ are independently $-CH_3$, $-CH_2CH_3$, $-OH$, $-OCH_3$, or $-CH(CH_3)_2$.

In some embodiments, $R^{20a}$ is $-CH_3$ and $R^{20b}$ is hydrogen. In some embodiments, $R^{20a}$ and $R^{20b}$ are both $-CH_3$. In some embodiments, $R^{20a}$ and $R^{20b}$ are both unsubstituted alkyl. In some embodiments, $R^{20a}$ and $R^{20b}$ are both substituted alkyl. In some embodiments, $R^{20a}$ and $R^{20b}$ are both unsubstituted $C_{1-6}$ alkyl. In some embodiments, $R^{20a}$ and $R^{20b}$ are both substituted $C_{1-6}$ alkyl.

In some embodiments, $R^{20a}$ and $R^{20b}$ are both hydrogen. In some embodiments, $R^{20a}$ is hydrogen. In some embodiments, $R^{20a}$ is $-CH_3$. In some embodiments, $R^{20a}$ is $-CH_2CH_3$. In some embodiments, $R^{20b}$ is hydrogen. In some embodiments, $R^{20b}$ is $-CH_3$. In some embodiments, $R^{20b}$ is $-CH_2CH_3$ O. Groups $R^{23a}$ and $R^{23b}$ In some embodiments, $R^{23a}$ and $R^{23b}$ are independently hydrogen or substituted alkyl. In some embodiments, $R^{23a}$ and $R^{23b}$ are independently hydrogen or unsubstituted alkyl. In some embodiments, each of $R^{23a}$ and $R^{23b}$ is independently $-CH_3$, $-CH_2CH_3$, $-OH$, $-OCH_3$, or $-CH(CH_3)_2$.

In some embodiments, $R^{23a}$ is $-CH_3$ and $R^{23b}$ is hydrogen. In some embodiments, $R^{23a}$ and $R^{23b}$ are both $-CH_3$. In some embodiments, $R^{23a}$ and $R^{23b}$ are both unsubstituted alkyl. In some embodiments, $R^{23a}$ and $R^{23b}$ are both substituted alkyl. In some embodiments, $R^{23a}$ and $R^{23b}$ are both unsubstituted $C_{1-6}$ alkyl. In some embodiments, $R^{23a}$ and $R^{23b}$ are both substituted $C_{1-6}$ alkyl.

In some embodiments, $R^{23a}$ and $R^{23b}$ are both hydrogen. In some embodiments, $R^{23a}$ is hydrogen. In some embodiments, $R^{23a}$ is $-CH_3$. In some embodiments, $R^{23a}$ is $-CH_2CH_3$. In some embodiments, $R^{23b}$ is hydrogen. In some embodiments, $R^{23b}$ is $-CH_3$. In some embodiments, $R^{23b}$ is $-CH_2CH_3$ P. Integers m and n In some embodiments, n is 0, 1, 2, 3, or 4. In some embodiments, n is 0, 1, 2, or 3. In some embodiments, n is 0, 1 or 2. In some embodiments, n is 0 or 1. In some embodiments, n is 1 or 2. In some embodiments, n is 3 or 4. In some embodiments n is 0. In some embodiments n is 1. In another embodiment n is 2. In another embodiment n is 3. In another embodiment n is 4.

In some embodiments, m is 0, 1, 2, 3, or 4. In some embodiments, m is 0, 1, 2, or 3. In some embodiments, m is 0, 1 or 2. In some embodiments, m is 0 or 1. In some embodiments, m is 1 or 2. In some embodiments, m is 3 or 4. In some embodiments m is 0. In some embodiments m is 1. In another embodiment m is 2. In another embodiment m is 3. In another embodiment m is 4.

In some embodiments, m is 0 and n is 2. In some embodiments, m is 0 and n is 3. In some embodiments, m is 0 and n is 4.

In some embodiments, m is 1 and n is 0. In some embodiments, m is 1 and n is 1. In some embodiments, m is 1 and n is 2. In some embodiments, m is 1 and n is 3. In some embodiments, m is 1 and n is 4.

In some embodiments, m is 2 and n is 0. In some embodiments, m is 2 and n is 1. In some embodiments, m is 2 and n is 2. In some embodiments, m is 2 and n is 3. In some embodiments, m is 2 and n is 4.

In some embodiments, m is 3 and n is 0. In some embodiments, m is 3 and n is 1. In some embodiments, m is 3 and n is 2. In some embodiments, m is 3 and n is 3. In some embodiments, m is 3 and n is 4.

In some embodiments, m is 4 and n is 0. In some embodiments, m is 4 and n is 1. In some embodiments, m is 4 and n is 2. In some embodiments, m is 4 and n is 3. In some embodiments, m is 4 and n is 4.

In some embodiments, when m is 0, either $R^{15a}$ or $R^{15b}$ is not H.

In some embodiments, when m is 0, n is not 0. In some embodiments, when m is 0, n is not 1.

Q. Integers q, r, s, t, and u

In some embodiments, q is 0, 1, 2, or 3. In some embodiments, q is 0, 1 or 2. In some embodiments, q is 0 or 1. In some embodiments, q is 1 or 2. In some embodiments q is 0. In some embodiments q is 1. In another embodiment q is 2. In another embodiment q is 3.

In some embodiments, r is 0, 1, or 2. In some embodiments, r is 0 or 1. In some embodiments, r is 1 or 2. In some embodiments r is 0. In some embodiments r is 1. In another embodiment r is 2.

In some embodiments, s is 0, 1, or 2. In some embodiments, s is 0 or 1. In some embodiments, s is 1 or 2. In some embodiments s is 0. In some embodiments s is 1. In another embodiment s is 2.

In some embodiments, t is 0, 1, 2, or 3. In some embodiments, t is 0, 1 or 2. In some embodiments, t is 0 or 1. In some embodiments, t is 1 or 2. In some embodiments t is 0. In some embodiments t is 1. In another embodiment t is 2. In another embodiment t is 3.

In some embodiments, u is 1 or 2. In some embodiments, u is 1. In some embodiments, u is 2.

In some embodiments, r is 1 and s is 1.

In some embodiments, q is 0, 2, or 3; and t is 0, 2, or 3. In another embodiment q is 2, t is 2, and u is 1.

In some embodiments, q is 0, 2, or 3; and u is 1. In another embodiment q is 0, 2, or 3; t is 0, 2, or 3, and u is 1.

In another embodiment q is 1, t is 0, 2, or 3, and u is 2.

In some embodiments q, u, r, s, and t are not simultaneously 1. In some embodiments, when t is 0, 2, or 3 then q, u, s, and r are not simultaneously 1. In some embodiments, when q is 0 or 2 and u is 1, then t, s, and r are not simultaneously 1. In some embodiments, when u is 2 and q is 1, then t, s, and r are not simultaneously 1. In some embodiments, when r is 0 or 2, then q, u, s, and t are not simultaneously 1. In some embodiments, when s is 0 or 2, then q, u, r, and t are not simultaneously 1.

R. Integers p, $m_1$ and $n_1$

In some embodiments, $n_1$ is 1 or 2. In some embodiments $n_1$ is 0. In some embodiments $n_1$ is 1. In another embodiment $n_1$ is 2. In another embodiment $n_1$ is 3. In another embodiment $n_1$ is 4. In another embodiment $n_1$ is 5.

In some embodiments, $m_1$ is 1 or 2. In some embodiments $m_1$ is 0. In some embodiments $m_1$ is 1. In another embodiment $m_1$ is 2.

In some embodiments, p is 1 or 2. In some embodiments p is 0. In some embodiments p is 1. In another embodiment p is 2. In another embodiment p is 3. In another embodiment p is 4.

S. Group X

In some embodiments, X is —H, substituted or unsubstituted alkyl, substituted or unsubstituted alkenyl, substituted or unsubstituted aryl, substituted or unsubstituted heterocyclyl, or substituted or unsubstituted heteroaryl.

In some embodiments, X is hydrogen, substituted or unsubstituted heteroaryl, or substituted or unsubstituted alkyl.

In another embodiment, X is a substituted or unsubstituted heteroaryl.

In one embodiment, X is a substituted or unsubstituted 5-10 membered heteroaryl.

In one embodiment, X is hydrogen, halogen, substituted or unsubstituted alkyl, substituted or unsubstituted heterocyclyl, substituted or unsubstituted carbocyclyl, substituted or unsubstituted aryl, substituted or unsubstituted heteroaryl, or —$OR^{A1}$; wherein $R^{A1}$ is independently hydrogen, substituted or unsubstituted alkyl, substituted or unsubstituted carbocyclyl, substituted or unsubstituted aryl, or substituted or unsubstituted heteroaryl.

In some embodiments, X is hydrogen, or substituted or unsubstituted heteroaryl.

For example, in some instances X is a substituted or unsubstituted N-linked heteroaryl.

In one embodiment, N-linked heteroaryl is a 5-6 membered N-linked heteroaryl.

In some embodiments, X is

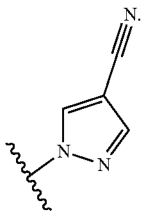 [SMILES: *n1cc(C#N)cn1]

In some embodiments, X is

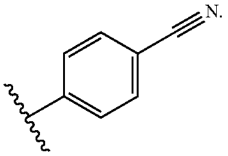 [SMILES: *c1ccc(C#N)cc1]

In some embodiments, X is —$CH_3$.

In some embodiments, X is:

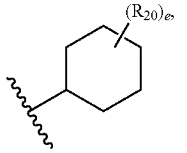
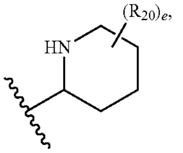
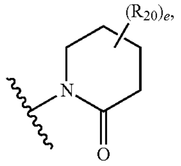
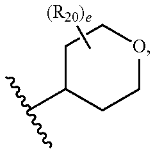
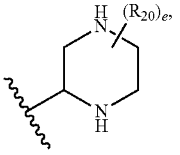
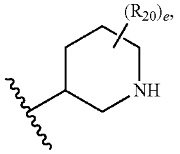
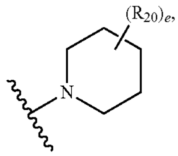
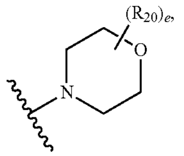
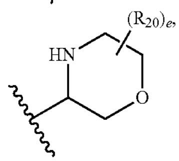
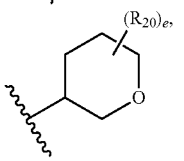

-continued

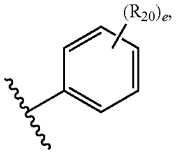 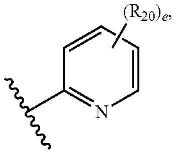

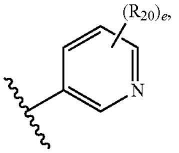 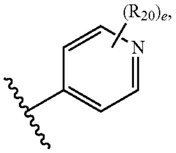

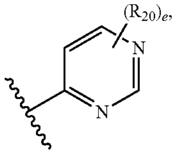 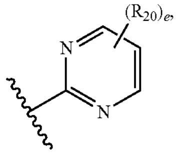

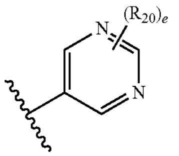 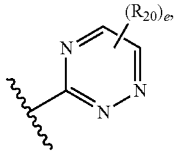

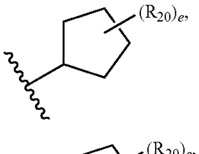 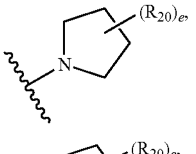

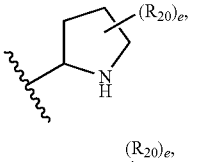 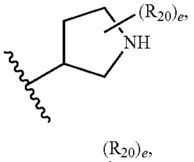

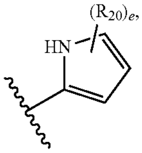 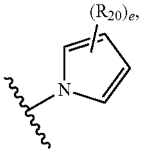

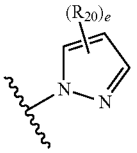, 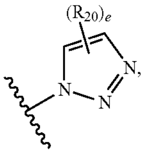

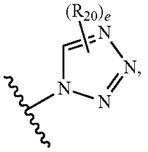 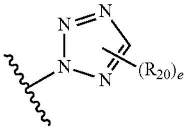

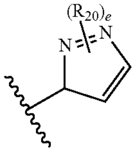, 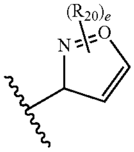,

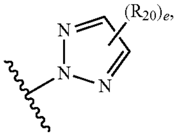

-continued

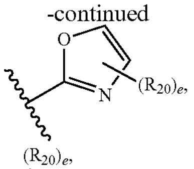

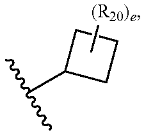 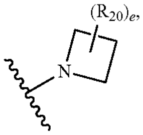

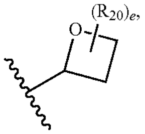 or 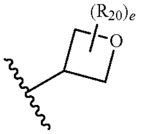

wherein each instance of $R_{20}$ is independently halogen, $-NO_2$, —CN, $-OR^{GA}$, $-N(R^{GA})_2$, $-C(=O)R^{GA}$, $-C(=O)OR^{GA}$, $-OC(=O)R^{GA}$, $-OC(=O)OR^{GA}$, $-C(=O)N(R^{GA})_2$, $-N(R^{GA})C(=O)R^{GA}$, $-OC(=O)N(R^{GA})_2$, $-N(R^{GA})C(=O)OR^{GA}$, $-S(=O)_2R^{GA}$, $-S(=O)_2OR^{GA}$, $-OS(=O)_2R^{GA}$, $-S(=O)_2N(R^{GA})_2$, or $-N(R^{GA})S(=O)_2R^{GA}$; substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-4}$ carbocylyl, or substituted or unsubstituted 3- to 4-membered heterocylyl;

wherein each instance of $R^{GA}$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ carbocylyl, substituted or unsubstituted 3-6 membered heterocylyl, substituted or unsubstituted aryl, substituted or unsubstituted heteroaryl, an oxygen protecting group when attached to oxygen, or a nitrogen protecting group when attached to nitrogen; or two $R^{GA}$ groups are taken with the intervening atoms to form a substituted or unsubstituted carbocyclic or substituted or unsubstituted heterocyclic ring; and e is 0, 1, 2, 3, 4, or 5.

In some embodiments, X is:

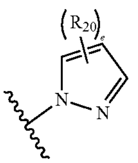, 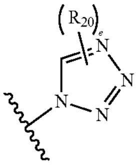, or 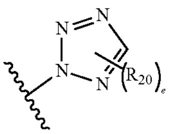

wherein each instance of $R_{20}$ is, independently, halogen, $-NO_2$, —CN, $-OR^{GA}$, $-N(R^{GA})_2$, $-C(=O)R^{GA}$, $-C(=O)OR^{GA}$, $-C(=O)N(R^{GA})_2$, $-N(R^{GA})C(=O)R^{GA}$, $-OC(=O)N(R^{GA})_2$, substituted or unsubstituted $C_{1-6}$ alkyl, substituted or unsubstituted 3-4 membered carbocylyl, substituted or unsubstituted 3-4 membered heterocyclyl;

wherein each instance of $R^{GA}$ is independently hydrogen, substituted or unsubstituted $C_{1-6}$ alkyl, substituted or unsubstituted aryl, substituted or unsubstituted heteroaryl, an oxygen protecting group when attached to oxygen, a nitrogen protecting group when attached to nitrogen, or two $R^{GA}$ groups are taken with the intervening atoms to form a substituted or unsubstituted carbocyclic or heterocyclic ring; and e is 0, 1, 2, or 3.

In some embodiments X is:

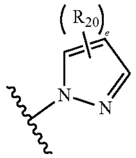
, wherein each instance of $R_{20}$ is, independently, halogen, —$NO_2$, —CN, —$OR^{GA}$, —$N(R^{GA})_2$, —C(=O)$R^{GA}$, —C(=O)$OR^{GA}$, —C(=O)$N(R^{GA})_2$, —$N(R^{GA})$C(=O)$R^{GA}$, —OC(=O)$N(R^{GA})_2$, substituted or unsubstituted $C_{1-6}$ alkyl, substituted or unsubstituted 3-4 membered carbocylyl, substituted or unsubstituted 3-4 membered heterocyclyl;

wherein each instance of $R^{GA}$ is independently hydrogen, substituted or unsubstituted $C_{1-6}$ alkyl, substituted or unsubstituted aryl, substituted or unsubstituted heteroaryl, or two $R^{GA}$ groups are taken with the intervening atoms to form a substituted or unsubstituted carbocyclic or heterocyclic ring; and e is 0, 1, 2, or 3.

T. Group A, Z, W, and Y

In some embodiments, A is $CR^{17}$, wherein $R^{17}$ is selected from the group consisting of a hydrogen atom, a deuterium atom, an alkyl group, a deuterated alkyl group, a hydroxyl group, an amino group, an alkenyl group, an alkynyl group, a cycloalkyl group, a heterocyclyl group, an aryl group, and a heteroaryl group, wherein the alkyl group, the cycloalkyl group, the heterocyclyl group, the aryl group and the heteroaryl group are optionally further substituted by one or more of the substituent groups selected from the group consisting of a deuterium atom, a substituted or unsubstituted alkyl group, a halogen, a hydroxyl group, a substituted or unsubstituted amino group, an oxo group, a nitro group, a cyano group, an alkenyl group, an alkynyl group, an alkoxy group, a hydroxyalkyl group, a substituted or unsubstituted cycloalkyl group, a substituted or unsubstituted heterocyclic group, a substituted or unsubstituted aryl group, and a substituted or unsubstituted heteroaryl group.

In some embodiments, A is N. In some embodiments, A is CH. In some embodiments, A is $C(CH_3)$. In some embodiments, A is $C(CH_2CH_3)$. In some embodiments, A is C when ------ is a double bond;

In some embodiments, Z is —$CH_2$—. In some embodiments, Z is —$C(CH_2CH_3)_2$—. In some embodiments, Z is —$C(CH_3)_2$—. In some embodiments, Z is —NH—. In some embodiments, Z is —O—.

In some embodiments, W is —$S(CH_2)_2$—. In some embodiments, W is

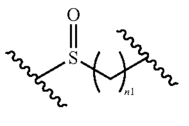
.

In some embodiments, W is

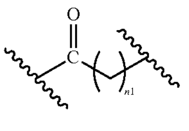
.

In some embodiments, W is

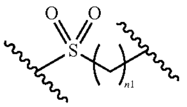
.

In some embodiments, W is

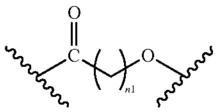
.

In some embodiments, W is

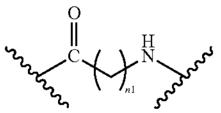
.

In some embodiments, W is

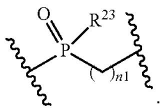
.

In some embodiments, Z is —$CH_2$—. In some embodiments, Z is —$C(CH_2CH_3)_2$—. In some embodiments, Z is —$C(CH_3)_2$—. In some embodiments, Z is —NH—. In some embodiments, Z is —O—.

In some embodiments, Y is oxygen. In some embodiments, Y is —$CH_2$—.

U. Group $R_{20}$

In some embodiments, $R_{20}$ is —CN.

In some embodiments, $R_{20}$ is unsubstituted alkyl.

In another embodiment, $R_{20}$ is unsubstituted $C_{1-6}$ alkyl.

In one embodiment, $R_{20}$ is methyl.

V. Group $R^{55}$

In some embodiments, $R^{55}$ is hydrogen, halogen, cyano, or substituted or unsubstituted alkyl.

In some embodiments $R^{55}$ is cyano. In another embodiment, $R^{55}$ is methyl. In one example $R^{55}$ is hydrogen. In another example $R^{55}$ is halogen.

W. Group $R^D$

In some embodiments, $R^D$ is independently hydrogen, halogen, —CN, —$NO_2$, oxo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{C3}$, —$N(R^{C3})_2$, —$SR^{C3}$, —C(=O)$R^{C3}$, —C(=O)$OR^{C3}$, —C(=O)$SR^{C3}$, —C(=O)$N(R^{C3})_2$, —OC(=O)$R^{C3}$, —OC(=O)$OR^{C3}$, —OC(=O)$N(R^{C3})_2$, —OC(=O)$SR^{C3}$, —$OS(=O)_2R^{C3}$, —$OS(=O)_2OR^{C3}$, —$OS(=O)_2N(R^{C3})_2$, —$N(R^{C3})$C(=O)$R^{C3}$, —$N(R^{C3})C(=NR^{C3})R^{C3}$, —$N(R^{C3})$C(=O)$OR^{C3}$, —$N(R^{C3})$C(=O)$N(R^{C3})_2$, —$N(R^{C3})$C(=$NR^{C3}$) $N(R^{C3})_2$, —$N(R^{C3})S(=O)_2R^{C3}$, —$N(R^{C3})S(=O)_2OR^{C3}$, —$N(R^{C3})S(=O)_2N(R^{C3})_2$, —SC(=O)$R^{C3}$, —SC(=O)$OR^{C3}$, —SC(=O)$SR^{C3}$, —SC(=O)$N(R^{C3})_2$, $-S(=O)_2R^{C3}$, $-S(=O)_2OR^{C3}$, or $-S(=O)_2N(R^{C3})_2$, wherein each instance of $R^{C3}$ is independently selected from hydrogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted carbocyclyl, or substituted or unsubstituted heterocyclyl.

In some embodiments, each $R^D$ is independently hydrogen, halogen, —CN, $-NO_2$, oxo, hydroxy, substituted or unsubstituted alkyl, substituted or unsubstituted alkenyl, substituted or unsubstituted alkynyl, or substituted or unsubstituted carbocyclyl.

In some embodiments, each $R^D$ is independently hydrogen, oxo, substituted or unsubstituted alkyl, hydroxy, or substituted or unsubstituted carbocyclyl.

In some embodiments, each $R^D$ is independently hydrogen, oxo, methyl, ethyl, hydroxy, or cyclopropyl.

In some embodiments, a method of treating a CNS-related disorder in a subject in need thereof, comprises administering to the subject an effective amount of a compound described herein or a pharmaceutically acceptable salt thereof. In some embodiments, the CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In some embodiments, the CNS-related disorder is depression. In some embodiments, the CNS-related disorder is postpartum depression. In some embodiments, the CNS-related disorder is major depressive disorder. In some embodiments, the major depressive disorder is moderate major depressive disorder. In some embodiments, the major depressive disorder is severe major depressive disorder.

In some embodiments, the compound is a compound of Formula VI-A:

(VI-A)

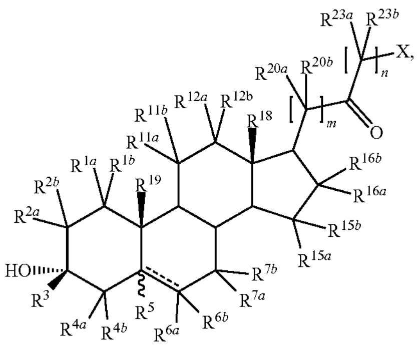

or a pharmaceutically acceptable salt thereof.

In some embodiments, the compound is a compound of Formula VI-B:

(VI-B)

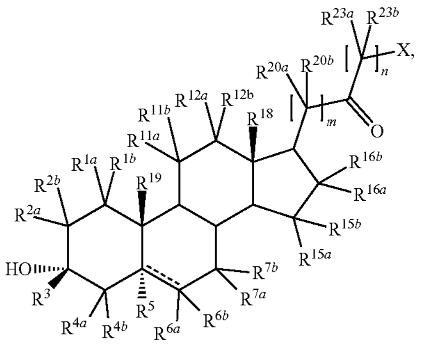

or a pharmaceutically acceptable salt thereof.

In some embodiments, the compound is a compound of Formula VI-C:

(VI-C)

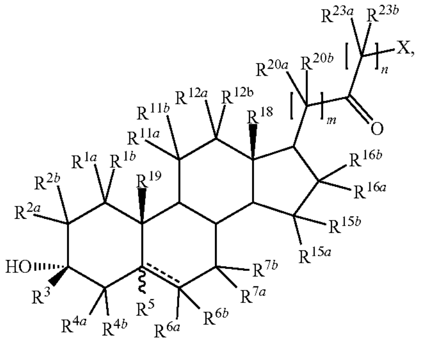

or a pharmaceutically acceptable salt thereof.

In some embodiments, the compound is a compound of Formula VI-D:

(VI-D)

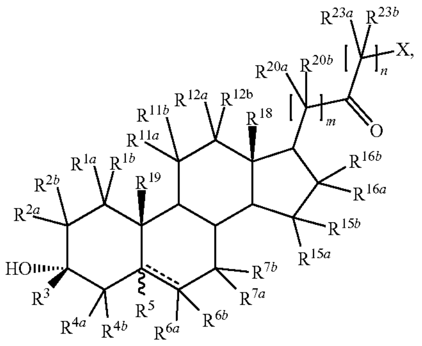

or a pharmaceutically acceptable salt thereof.

In some embodiments, the compound is a compound of Formula VI-E:

(VI-E)

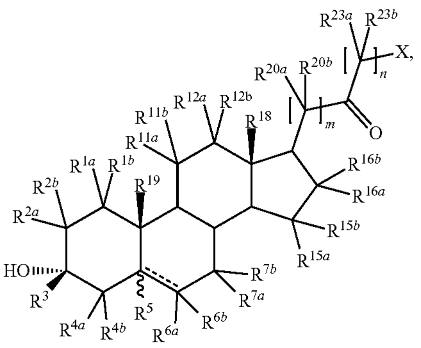

or a pharmaceutically acceptable salt thereof.

In some embodiments, the compound is a compound of Formula VI-F:

(VI-F)

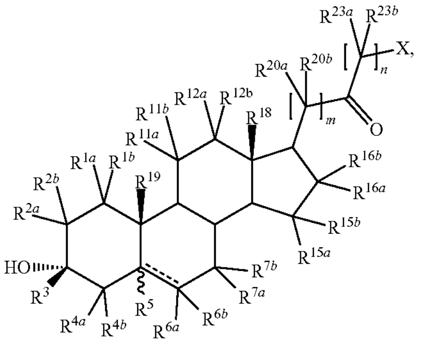

or a pharmaceutically acceptable salt thereof.

In some embodiments, the compound is a compound of Formula VI-G:

(VI-G)

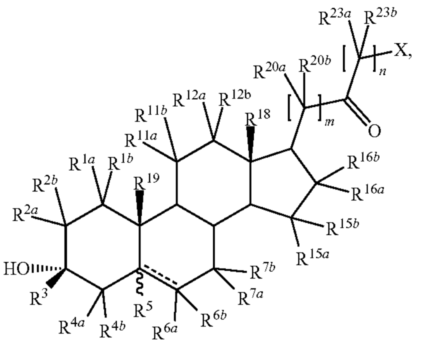

or a pharmaceutically acceptable salt thereof.

In some embodiments, the compound is a compound of Formula VI-H:

(VI-H)

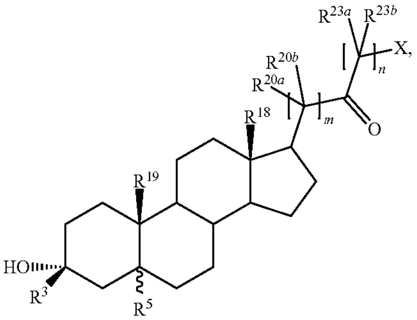

or a pharmaceutically acceptable salt thereof.

In some embodiments, the compound is a compound of Formula VI-IA:

(VI-IA)

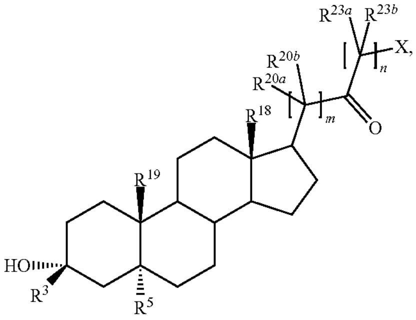

or a pharmaceutically acceptable salt thereof.

In some embodiments, the compound is a compound of Formula VI-IB:

(VI-IB)

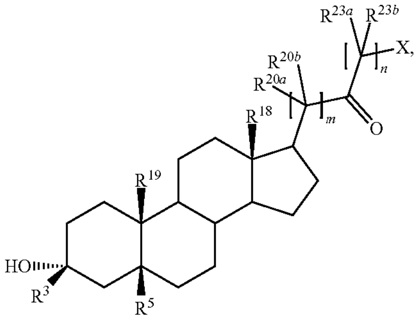

or a pharmaceutically acceptable salt thereof.

In some embodiments, the compound is selected from the group consisting of the compounds identified in Table 1 below.

TABLE 1

Example species of the compounds of the instant invention.

| Example | Structure |
|---|---|
| 1 | 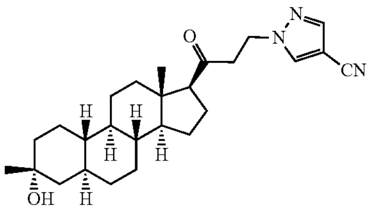 |
| 2 | 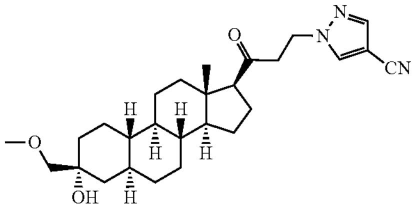 |
| 3 | 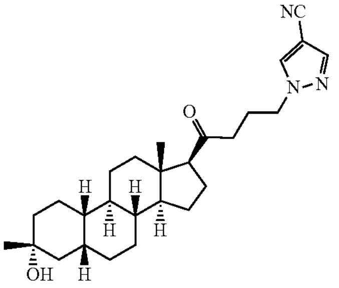 |
| 4 | 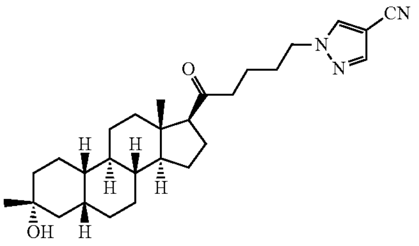 |
| 5 | 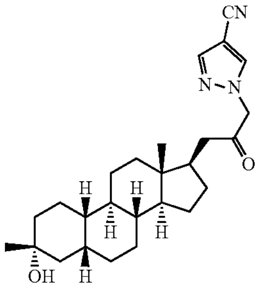 |
| 6 | 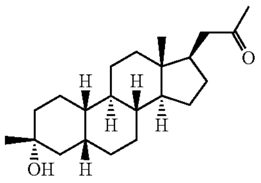 |

TABLE 1-continued

Example species of the compounds of the instant invention.

| Example | Structure |
|---|---|
| 7 | 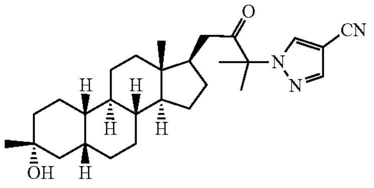 |
| 8 | 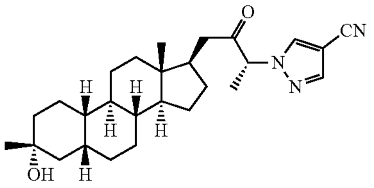 |
| 9 | 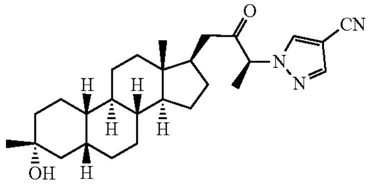 |
| 10 | 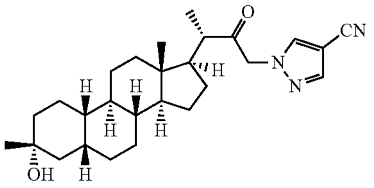 |
| 11 | 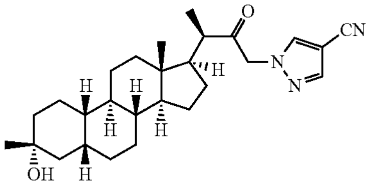 |
| 12 | 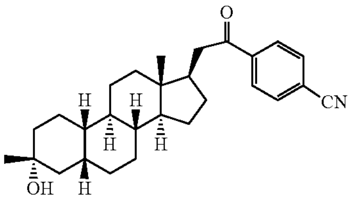 |
| 13 | 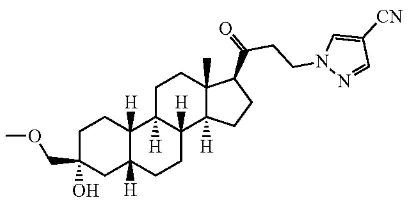 |

or a pharmaceutically acceptable salt thereof.

In one aspect, provided herein is a pharmaceutically acceptable salt of a compound described herein (e.g., a compound of Formula (I) and a compound of Formula (VI)).

In one aspect, provided herein is a pharmaceutical composition comprising a compound described herein (e.g., a compound of Formula (I), and a compound of Formula (VI)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount.

Compounds of the present invention as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS activity.

Thus, in another aspect, provided are methods of treating a CNS-related disorder in a subject in need thereof, comprising administering to the subject an effective amount of a compound of the present invention. In certain embodiments, CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In certain embodiments, the CNS-related disorder is depression. In certain embodiments, the CNS-related disorder is postpartum depression. In certain embodiments, the CNS-related disorder is major depressive disorder. In certain embodiments, the major depressive disorder is moderate major depressive disorder. In certain embodiments, the major depressive disorder is severe major depressive disorder. In certain embodiments, the compound is administered orally, subcutaneously, intravenously, or intramuscularly. In certain embodiments, the compound is administered orally. In certain embodiments, the compound is administered chronically. In certain embodiments, the compound is administered continuously, e.g., by continuous intravenous infusion.

Exemplary compounds of the invention may be synthesized from the following known starting materials using methods known to one skilled in the art or certain references, In one aspect, provided herein is a pharmaceutically acceptable salt of a compound described herein (e.g., a compound of Formula (I), and a compound of Formula (VI)).

III. ALTERNATIVE EMBODIMENTS

In an alternative embodiment, compounds described herein may also comprise one or more isotopic substitutions. For example, hydrogen may be $^2H$ (D or deuterium) or $^3H$ (T or tritium); carbon may be, for example, $^{13}C$ or $^{14}C$; oxygen may be, for example, $^{18}O$; nitrogen may be, for example, $^{15}N$, and the like. In other embodiments, a particular isotope (e.g., $^3H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

IV. PHARMACEUTICAL COMPOSITIONS

In one aspect, provided herein is a pharmaceutical composition comprising a compound described herein (e.g., a compound of Formula (I)) or a pharmaceutically acceptable salt thereof, and a pharmaceutically acceptable excipient. In certain embodiments, the compound of the present invention is provided in an effective amount in the pharmaceutical composition. In certain embodiments, the compound of the present invention is provided in a therapeutically effective amount.

In certain embodiments, the pharmaceutical composition comprises an effective amount of the active ingredient. In certain embodiments, the pharmaceutical composition comprises a therapeutically effective amount of the active ingredient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present invention may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 20 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 5 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

The compounds of the present invention can also be administered in sustained release forms or from sustained release drug delivery systems. A description of representative sustained release materials can be found in Remington's Pharmaceutical Sciences.

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

In another aspect, the invention provides a pharmaceutical composition comprising a compound of the present invention and a pharmaceutically acceptable excipient, e.g., a composition suitable for injection, such as for intravenous (IV) administration.

Pharmaceutically acceptable excipients include any and all diluents or other liquid vehicles, dispersion or suspension aids, surface active agents, isotonic agents, preservatives, lubricants and the like, as suited to the particular dosage form desired, e.g., injection. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* $21^{st}$ Edition (Lippincott Williams & Wilkins, 2005).

For example, injectable preparations, such as sterile injectable aqueous suspensions, can be formulated according to the known art using suitable dispersing or wetting agents and suspending agents. Exemplary excipients that can be employed include, but are not limited to, water, sterile saline or phosphate-buffered saline, or Ringer's solution.

In certain embodiments, the pharmaceutical composition further comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, substituted or unsubstituted methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as CAPTISOL®. See, e.g., U.S. Pat. No. 5,376,645. In certain embodiments, the composition comprises hexapropyl-β-cyclodextrin. In a more particular embodiment, the composition comprises hexapropyl-β-cyclodextrin (10-50% in water).

The injectable composition can be sterilized, for example, by filtration through a bacterial-retaining filter, or by incorporating sterilizing agents in the form of sterile solid compositions which can be dissolved or dispersed in sterile water or other sterile injectable medium prior to use.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, response of the individual patient, the severity of the patient's symptoms, and the like.

The compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampules or syringes of the liquid compositions. In such compositions, the compound is usually a minor component (from about 0.1% to about 50% by weight or preferably from about 1% to about 40% by weight) with the remainder being various vehicles or carriers and processing aids helpful for forming the desired dosing form.

The compounds provided herein can be administered as the sole active agent, or they can be administered in combination with other active agents. In one aspect, the present invention provides a combination of a compound of the present invention and another pharmacologically active agent. Administration in combination can proceed by any technique apparent to those of skill in the art including, for example, separate, sequential, concurrent, and alternating administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

In one aspect, provided is a kit comprising a composition (e.g., a solid composition) comprising a compound of Formula (I). In one aspect, provided is a kit comprising a composition (e.g., a solid composition) comprising a compound of Formula (VI).

V. METHODS OF USE AND TREATMENT

In an aspect, compounds described herein, e.g., compounds of Formula (I) or Formula (VI), are envisioned to be useful as therapeutic agents for treating a CNS-related disorder (e.g., sleep disorder, a mood disorder such as depression, a schizophrenia spectrum disorder, a convulsive disorder, epileptogenesis, a disorder of memory and/or cognition, a movement disorder, a personality disorder, autism spectrum disorder, pain, traumatic brain injury, a vascular disease, a substance abuse disorder and/or withdrawal syndrome, or tinnitus) in a subject in need (e.g., a subject with Rett syndrome, Fragile X syndrome, or Angelman syndrome). Exemplary CNS conditions related to GABA-modulation include, but are not limited to, sleep disorders [e.g., insomnia], mood disorders [e.g., depression depression (e.g., major depressive disorder (MDD)), dysthymic disorder (e.g., mild depression), bipolar disorder (e.g., I and/or II), anxiety disorders (e.g., generalized anxiety disorder (GAD), social anxiety disorder), stress, post-traumatic stress disorder (PTSD), compulsive disorders (e.g., obsessive compulsive disorder (OCD))], schizophrenia spectrum disorders [e.g., schizophrenia, schizoaffective disorder], convulsive disorders [e.g., epilepsy (e.g., status epilepticus (SE)), seizures], disorders of memory and/or cognition [e.g., attention disorders (e.g., attention deficit hyperactivity disorder (ADHD)), dementia (e.g., Alzheimer's type dementia, Lewis body type dementia, vascular type dementia], movement disorders [e.g., Huntington's disease, Parkinson's disease], personality disorders [e.g., anti-social personality disorder, obsessive compulsive personality disorder], autism spectrum disorders (ASD) [e.g., autism, monogenetic causes of autism such as synaptophathy's, e.g., Rett syndrome, Fragile X syndrome, Angelman syndrome], pain [e.g., neuropathic pain, injury related pain syndromes, acute pain, chronic pain], traumatic brain injury (TBI), vascular diseases [e.g., stroke, ischemia, vascular malformations], substance abuse disorders and/or withdrawal syndromes [e.g., addition to opiates, cocaine, and/or alcohol], and tinnitus.

In certain embodiments, CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, tinnitus, or status epilepticus. In certain embodiments, the CNS-related disorder is depression. In certain embodiments, the CNS-related disorder is postpartum depression. In certain embodiments, the CNS-related disorder is major depressive disorder. In certain embodiments, the major depressive disorder is moderate major depressive disorder. In certain embodiments, the major depressive disorder is severe major depressive disorder.

In an aspect, provided is a method of alleviating or preventing seizure activity in a subject, comprising administering to the subject in need of such treatment an effective amount of a compound of the present invention. In some embodiments, the method alleviates or prevents epileptogenesis.

In yet another aspect, provided is a combination of a compound of the present invention and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, provided is a method of treating or preventing brain excitability in a subject susceptible to or afflicted with a condition associated with brain excitability, comprising administering to the subject an effective amount of a compound of the present invention to the subject.

In yet another aspect, provided is a method of treating or preventing stress or anxiety in a subject, comprising administering to the subject in need of such treatment an effective amount of a compound of the present invention, or a composition thereof.

In yet another aspect, provided is a method of alleviating or preventing insomnia in a subject, comprising administering to the subject in need of such treatment an effective amount of a compound of the present invention, or a composition thereof.

In yet another aspect, provided is a method of inducing sleep and maintaining substantially the level of REM sleep that is found in normal sleep, wherein substantial rebound insomnia is not induced, comprising administering an effective amount of a compound of the present invention.

In yet another aspect, provided is a method of alleviating or preventing premenstrual syndrome (PMS) or postnatal depression (PND) in a subject, comprising administering to the subject in need of such treatment an effective amount of a compound of the present invention.

In yet another aspect, provided is a method of treating or preventing mood disorders in a subject, comprising administering to the subject in need of such treatment an effective amount of a compound of the present invention. In certain embodiments the mood disorder is depression.

In yet another aspect, provided is a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, provided is a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally, subcutaneously, intramuscularly, or intravenously.

A. Neuroendocrine Disorders and Dysfunction

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain. In some embodiments, the neuroendocrine disorder or dysfunction is associated with a women's health disorder or condition (e.g., a women's health disorder or condition described herein). In some embodiments, the neuroendocrine disorder or dysfunction is associated with a women's health disorder or condition is polycystic ovary syndrome.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, attention difficulties, loss of lipido, infertility, amenorrhea, loss of muscle mass, increased belly body fat, low blood pressure, reduced heart rate, hair loss, anemia, constipation, cold intolerance, and dry skin.

B. Neurodegenerative Diseases and Disorders

The methods described herein can be used for treating neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

C. Mood Disorders

Also provided herein are methods for treating a mood disorder, for example clinical depression, postnatal depression or postpartum depression, perinatal depression, atypical depression, melancholic depression, psychotic major depression, cataonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or physchological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness.

Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

In some embodiments, the method comprises monitoring a subject with a known depression scale, e.g., the Hamilton Depression (HAM-D) scale, the Clinical Global Impression-Improvement Scale (CGI), and the Montgomery-Åsberg Depression Rating Scale (MADRS). In some embodiments, a therapeutic effect can be determined by reduction in Hamilton Depression (HAM-D) total score exhibited by the subject. Reduction in the HAM-D total score can happen within 4, 3, 2, or 1 days; or 96, 84, 72, 60, 48, 24, 20, 16, 12, 10, 8 hours or less. The therapeutic effect can be assessed across a specified treatment period. For example, the therapeutic effect can be determined by a decrease from baseline in HAM-D total score after administering a compound described herein, e.g., a compound of Formula (I) (e.g., 12, 24, or 48 hours after administration; or 24, 48, 72, or 96 hours or more; or 1 day, 2 days, 14 days, 21 days, or 28 days; or 1 week, 2 weeks, 3 weeks, or 4 weeks; or 1 month, 2 months, 6 months, or 10 months; or 1 year, 2 years, or for life).

In some embodiments, the subject has a mild depressive disorder, e.g., mild major depressive disorder. In some embodiments, the subject has a moderate depressive disorder, e.g., moderate major depressive disorder. In some embodiments, the subject has a severe depressive disorder, e.g., severe major depressive disorder. In some embodiments, the subject has a very severe depressive disorder, e.g., very severe major depressive disorder. In some embodiments, the baseline HAM-D total score of the subject (i.e., prior to treatment with a compound described herein, e.g., a compound of Formula (I)) is at least 24. In some embodiments, the baseline HAM-D total score of the subject is at least 18. In some embodiments, the baseline HAM-D total score of the subject is between and including 14 and 18. In some embodiments, the baseline HAM-D total score of the subject is between and including 19 and 22. In some embodiments, the HAM-D total score of the subject before treatment with a compound described herein, e.g., a compound of Formula (I), is greater than or equal to 23. In some embodiments, the baseline score is at least 10, 15, or 20. In some embodiments, the HAM-D total score of the subject after treatment with a compound described herein, e.g., a compound of Formula (I), is about 0 to 10 (e.g., less than 10; 0 to 10, 0 to 6, 0 to 4, 0 to 3, 0 to 2, or 1.8). In some embodiments, the HAM-D total score after treatment with a compound described herein, e.g., a compound of Formula (I), is less than 10, 7, 5, or 3. In some embodiments, the decrease in HAM-D total score is from a baseline score of about 20 to 30 (e.g., 22 to 28, 23 to 27, 24 to 27, 25 to 27, 26 to 27) to a HAM-D total score at about 0 to 10 (e.g., less than 10; 0 to 10, 0 to 6, 0 to 4, 0 to 3, 0 to 2, or 1.8) after treatment with a compound described herein, e.g., a compound of Formula (I). In some embodiments, the decrease in the baseline HAM-D total score to HAM-D total score after treatment with a compound described herein, e.g., a compound of Formula (I), is at least 1, 2, 3, 4, 5, 7, 10, 25, 40, 50, or 100 fold). In some embodiments, the percentage decrease in the baseline HAM-D total score to HAM-D total score after treatment with a compound described herein, e.g., a compound of Formula (I), is at least 50% (e.g., 60%, 70%, 80%, or 90%). In some embodiments, the therapeutic effect is measured as a decrease in the HAM-D total score after treatment with a compound described herein, e.g., a compound of Formula (I), relative to the baseline HAM-D total score (e.g., 12, 24, 48 hours after administration; or 24, 48, 72, 96 hours or more; or 1 day, 2 days, 14 days, or more) is at least 10, 15, or 20 points.

In some embodiments, the method of treating a depressive disorder, e.g., major depressive disorder provides a therapeutic effect (e.g., as measured by reduction in Hamilton Depression Score (HAM-D)) within 14, 10, 4, 3, 2, or 1 days, or 24, 20, 16, 12, 10, or 8 hours or less. In some embodiments, the method of treating the depressive disorder, e.g., major depressive disorder, provides a therapeutic effect (e.g., as determined by a statistically significant reduction in HAM-D total score) within the first or second day of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 14 days since the beginning of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 21 days since the beginning of the treatment with a compound described herein, e.g., a compound of Formula (I). In some embodiments, the method of treating the depressive disorder, e.g., major depressive disorder, provides a therapeutic effect (e.g., as determined by a statistically significant reduction in HAM-D total score) within less than or equal to 28 days since the beginning of the treatment with a compound described herein, e.g., a compound of Formula (I). In some embodiments, the therapeutic effect is a decrease from baseline in HAM-D total score after treatment with a compound described herein, e.g., a compound of Formula (I) (e.g., treatment with a compound described herein, e.g., a compound of Formula (I), once a day for 14 days). In some embodiments, the HAM-D total score of the subject before treatment with a compound described herein, e.g., a compound of Formula (I), is at least 24. In some embodiments, the HAM-D total score of the subject before treatment with a compound described herein, e.g., a compound of Formula (I), is at least 18. In some embodiments, the HAM-D total score of the subject before treatment with a compound described herein, e.g., a compound of Formula (I), is between and including 14 and 18. In some embodiments, the decrease in HAM-D total score after treating the subject with a compound described herein, e.g., a compound of Formula (I), relative to the baseline HAM-D total score is at least 10. In some embodiments, the decrease in HAM-D total score after treating the subject with a compound described herein, e.g., a compound of Formula (I), relative to the baseline HAM-D total score is at least 15 (e.g., at least 17). In some embodiments, the HAM-D total score associated with treating the subject with a compound described herein, e.g., a compound of Formula (I), is no more than a number ranging from 6 to 8. In some embodiments, the HAM-D total score associated with treating the subject with a compound described herein, e.g., a compound of Formula (I), is no more than 7.

In some embodiments, the method provides therapeutic effect (e.g., as measured by reduction in Clinical Global Impression-Improvement Scale (CGI)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in CGI score at the end of a treatment period (e.g., 14 days after administration).

In some embodiments, the method provides therapeutic effect (e.g., as measured by reduction in Montgomery-Åsberg Depression Rating Scale (MADRS)) within 14, 10, 4, 3, 2, or 1 days, or 24, 20, 16, 12, 10, or 8 hours or less. In some embodiments, the CNS-disorder is a depressive disorder, e.g., major depressive disorder. In some embodiments, the method of treating the depressive disorder, e.g., major depressive disorder provides a therapeutic effect within the second day of the treatment period. In some embodiments, the therapeutic effect is a decrease from baseline in MADRS score at the end of a treatment period (e.g., 14 days after administration).

A therapeutic effect for major depressive disorder can be determined by a reduction in Montgomery-Åsberg Depression Rating Scale (MADRS) score exhibited by the subject. For example, the MADRS score can be reduced within 4, 3, 2, or 1 days; or 96, 84, 72, 60, 48, 24, 20, 16, 12, 10, 8 hours or less. The Montgomery-Åsberg Depression Rating Scale (MADRS) is a ten-item diagnostic questionnaire (regarding apparent sadness, reported sadness, inner tension, reduced sleep, reduced appetite, concentration difficulties, lassitude, inability to feel, pessimistic thoughts, and suicidal thoughts) which psychiatrists use to measure the severity of depressive episodes in patients with mood disorders.

In some embodiments, the method provides therapeutic effect (e.g., as measured by reduction in Edinburgh Postnatal Depression Scale (EPDS)) within 4, 3, 2, 1 days; 24, 20, 16, 12, 10, 8 hours or less. In some embodiments, the therapeutic effect is an improvement measured by the EPDS.

In some embodiments, the method provides therapeutic effect (e.g., as measured by reduction in Generalized Anxiety Disorder 7-Item Scale (GAD-7)) within 4, 3, 2, 1 days; 24, 20, 16, 12, 10, 8 hours or less.

D. Anxiety Disorders

Provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression E. Women's Health Disorders Provided herein are methods for treating conditions or disorders related to women's health. Conditions or disorders related to women's health include, but are not limited to, gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause).

Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but can include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activities, difficulty concentrating, fatigue, change in appetite, feeling out of control or overwhelmed, sleep problems, physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breastfeeding, and birth defects.

Miscarriage refers to a pregnancy that ends on its own, within the first 20 weeks of gestation.

Abortion refers to the deliberate termination of a pregnancy, which can be performed during the first 28 weeks of pregnancy.

Infertility and related disorders include uterine fibroids, polycystic ovary syndrome, endometriosis, and primary ovarian insufficiency.

Polycystic ovary syndrome (PCOS) refers to an endocrine system disorder among women of reproductive age. PCOS is a set of symptoms resulting from an elevated male hormone in women. Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer.

Other disorders and conditions that affect only women include Turner syndrome, Rett syndrome, and ovarian and cervical cancers.

Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes natural menopause and surgical menopause, which is a type of induced menopause due to an event such as surgery (e.g., hysterectomy, oophorectomy; cancer). It is induced when the ovaries are gravely damaged by, e.g., radiation, chemotherapy, or other medications.

F. Epilepsy

The compound of Formula (I), or pharmaceutically acceptable salt, or a pharmaceutically acceptable composition thereof, can be used in a method described herein, for example in the treatment of a disorder described herein such as epilepsy, status epilepticus, or seizure.

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

G. Epileptogenesis

The compounds and methods described herein can be used to treat or prevent epileptogenesis. Epileptogenesis is a gradual process by which a normal brain develops epilepsy (a chronic condition in which seizures occur). Epileptogenesis results from neuronal damage precipitated by the initial insult (e.g., status epilepticus).

H. Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

The compound of Formula (I) or pharmaceutically acceptable salt, or a pharmaceutically acceptable composition thereof, can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

The compound of Formula (VI) or pharmaceutically acceptable salt, or a pharmaceutically acceptable composition thereof, can also be administered as a prophylactic to a subject having a CNS disorder e.g., a traumatic brain injury, status epilepticus, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges; prior to the onset of a seizure.

I. Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

J. Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

K. Tremor

The methods described herein can be used to treat tremor, for example the compound of Formula (I) can be used to treat cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myloclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

L. Anesthesia/Sedation

Anesthesia is a pharmacologically induced and reversible state of amnesia, analgesia, loss of responsiveness, loss of skeletal muscle reflexes, decreased stress response, or all of these simultaneously. These effects can be obtained from a single drug which alone provides the correct combination of effects, or occasionally with a combination of drugs (e.g., hypnotics, sedatives, paralytics, analgesics) to achieve very specific combinations of results. Anesthesia allows patients to undergo surgery and other procedures without the distress and pain they would otherwise experience.

Sedation is the reduction of irritability or agitation by administration of a pharmacological agent, generally to facilitate a medical procedure or diagnostic procedure.

Sedation and analgesia include a continuum of states of consciousness ranging from minimal sedation (anxiolysis) to general anesthesia.

Minimal sedation is also known as anxiolysis. Minimal sedation is a drug-induced state during which the patient responds normally to verbal commands. Cognitive function and coordination may be impaired. Ventilatory and cardiovascular functions are typically unaffected.

Moderate sedation/analgesia (conscious sedation) is a drug-induced depression of consciousness during which the patient responds purposefully to verbal command, either alone or accompanied by light tactile stimulation. No interventions are usually necessary to maintain a patent airway. Spontaneous ventilation is typically adequate. Cardiovascular function is usually maintained.

Deep sedation/analgesia is a drug-induced depression of consciousness during which the patient cannot be easily aroused, but responds purposefully (not a reflex withdrawal from a painful stimulus) following repeated or painful stimulation. Independent ventilatory function may be impaired and the patient may require assistance to maintain a patent airway. Spontaneous ventilation may be inadequate. Cardiovascular function is usually maintained.

General anesthesia is a drug-induced loss of consciousness during which the patient is not arousable, even to painful stimuli. The ability to maintain independent ventilatory function is often impaired and assistance is often required to maintain a patent airway. Positive pressure ventilation may be required due to depressed spontaneous ventilation or drug-induced depression of neuromuscular function. Cardiovascular function may be impaired.

Sedation in the intensive care unit (ICU) allows the depression of patients' awareness of the environment and reduction of their response to external stimulation. It can play a role in the care of the critically ill patient, and encompasses a wide spectrum of symptom control that will vary between patients, and among individuals throughout the course of their illnesses. Heavy sedation in critical care has been used to facilitate endotracheal tube tolerance and ventilator synchronization, often with neuromuscular blocking agents.

In some embodiments, sedation (e.g., long-term sedation, continuous sedation) is induced and maintained in the ICU for a prolonged period of time (e.g., 1 day, 2 days, 3 days, 5 days, 1 week, 2 week, 3 weeks, 1 month, 2 months). Long-term sedation agents may have long duration of action. Sedation agents in the ICU may have short elimination half-life.

Procedural sedation and analgesia, also referred to as conscious sedation, is a technique of administering sedatives or dissociative agents with or without analgesics to induce a state that allows a subject to tolerate unpleasant procedures while maintaining cardiorespiratory function.

VI. EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative oxysterols that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

$^{1}$H-NMR reported herein (e.g., for the region between δ (ppm) of about 0.5 to about 4 ppm) will be understood to be an exemplary interpretation of the NMR spectrum (e.g., exemplary peak integratations) of a compound.

LC-ELSD/MS: (Mobile Phase: 1.5 ML/4 L TFA in water (solvent A) and 0.75 ML/4 L TFA in acetonitrile (solvent B), using the elution gradient 30%-90% (solvent B) over 0.9 minutes and holding at 90% for 0.6 minutes at a flow rate of 1.2 ml/min; Column: Xtimate C18 2.1*30 mm, 3 um; Wavelength: UV 220 nm; Column temperature: 50° C.; MS ionization: ESI; Detector: PDA & ELSD.

Abbreviations

DCM: dichloromethane; DMF: dimethylformamide; DMP: Dess-Martin periodinane; DMSO: dimethyl sulfoxide; EtOAc: ethyl acetate; EtOH: ethanol; HATU: (1-[Bis(dimethylamino)methylene]-1H-1,2,3-triazolo[4,5-b]pyridinium 3-oxide hexafluorophosphate; Mel: methyl iodide; MeOH: methanol; t-BuOK: potassium tert-butoxide; i-PrMrCl: isopropylmagnesium chloride; PCC: pyridinium chlorochromate; PE: petroleum ether; TBAF: tetra-n-butylammonium fluoride; TBSCl: tert-Butyl(chloro)dimethylsilane; TBSOTf: tert-Butyldimethylsilyl Trifluoromethanesulfonate; THF: tetrahydrofuran; 9-BBN dimer: 9-borabicyclo(3.3.1)nonane(dimer); Ts: p-toluenesulfonyl;

Example 1: Synthesis of 1-(3-((3R,5S,8R,9R,10S,13S,14S,17S)-3-hydroxy-3,13-dimethylhexadecahydro-1H-cyclopenta[a]phenanthren-17-yl)-3-oxopropyl)-1H-pyrazole-4-carbonitrile (1)

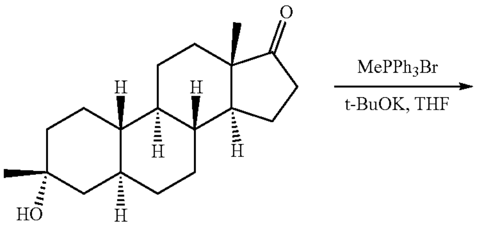

1.0

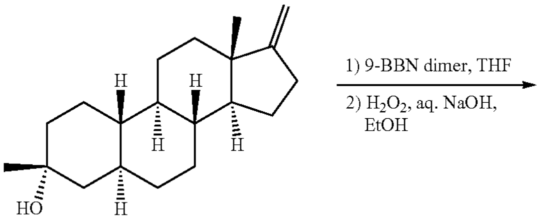

1.1

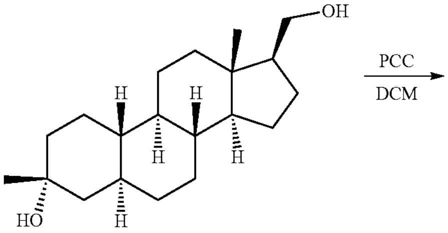

1.2

-continued

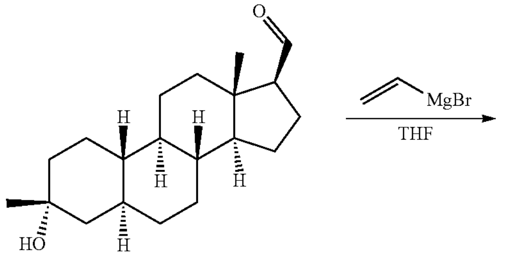

1.3

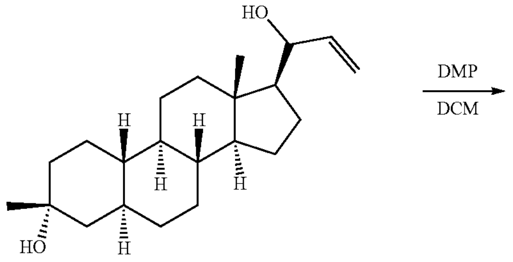

1.4

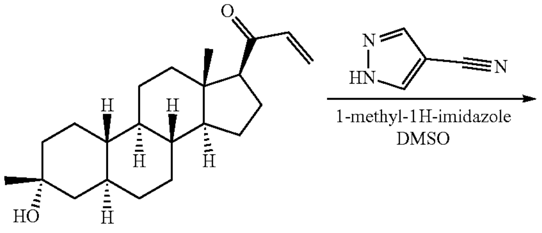

1.5

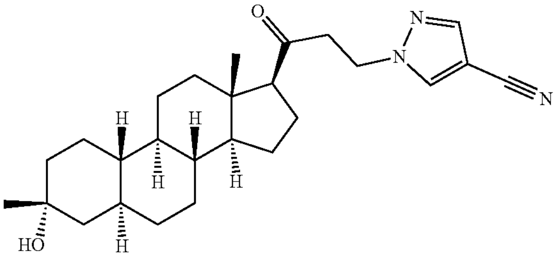

1

Synthesis of 1.1

To a solution of $PPh_3MeBr$ (20.2 g, 56.6 mmol) in THF (200 mL) was added t-BuOK (6.35 g, 56.6 mmol). The reaction mixture was stirred for 0.5 h at 60° C. A solution of 1.0 (5.5 g, 18.9 mmol) in THE (100 mL) was added to the reaction at 60° C. After the reaction mixture was stirred for 12 h at 60° C., the mixture was poured into saturated $NH_4Cl$ (300 mL) and extracted with EtOAc (2×100 mL). The combined organic phase was washed with saturated brine (2×100 mL), dried over anhydrous $Na_2SO_4$, filtered and concentrated under vacuum. The mixture was purified by silica gel chromatography (0-15% EtOAc in PE) to give 1.1 (4.8 g, 88%).

$^1H$ NMR (400 MHz, $CDCl_3$) $\delta_H$ 4.66-4.58 (m, 2H), 2.52-2.41 (m, 1H), 2.29-2.17 (m, 1H), 1.89-1.57 (m, 7H), 1.55-1.51 (m, 1H), 1.39-1.22 (m, 4H), 1.20 (s, 3H), 1.20-0.92 (m, 8H), 0.78 (s, 3H), 0.75-0.65 (m, 2H).

Synthesis of 1.2

To a solution of 1.1 (4.8 g, 16.6 mmol) in THE (100 mL) was added 9-BBN dimer (8.03 g, 33.2 mmol) under $N_2$. The reaction mixture was stirred at 60° C. under $N_2$ for 2 h to give a colorless solution. The mixture was cooled to 0° C. and EtOH (11.4 mL, 199 mmol) and aq. NaOH (39.8 mL, 5M, 199 mmol) was added to the mixture, followed by the dropwise addition of $H_2O_2$ (19.9 mL, 10M, 199 mmol) at 15° C. After the mixture was stirred at 60° C. for 2 h, the mixture was cooled, poured into $Na_2S_2O_3$ (200 mL, sat.) and stirred for 30 mins. The aqueous layer was extracted with EtOAc (2×200 mL). The combined organic layer was washed with saturated brine (2×100 mL), dried over anhydrous $Na_2SO_4$, filtered and concentrated to give 1.2 (5.5 g).

$^1H$ NMR (400 MHz, $CDCl_3$) $\delta_H$ 3.78-3.65 (m, 1H), 3.61-3.48 (m, 1H), 1.88-1.58 (m, 9H), 1.55-1.22 (m, 5H), 1.20 (s, 3H), 1.19-0.91 (m, 10H), 0.81-0.67 (m, 2H), 0.65 (s, 3H).

Synthesis of 1.3

To a solution of 1.2 (1.0 g, 3.26 mmol) in DCM (20 mL) was added PCC (1.4 g, 6.52 mmol) and silica gel (1.4 g). The mixture was stirred at 25° C. for 0.5 h, filtered, washed with EtOAc (2×50 mL) and concentrated. The residue was purified by silica gel chromatography (0-20% EtOAc in PE) to give 1.3 (740 mg, 75%).

$^1H$ NMR (400 MHz, $CDCl_3$) $\delta_H$ 9.77 (d, 1H), 2.57-1.94 (m, 4H), 1.84-1.57 (m, 8H), 1.43-1.26 (m, 5H), 1.20 (s, 3H), 1.14-0.98 (m, 6H), 0.76 (s, 3H), 0.75-0.63 (m, 2H).

Synthesis of 1.4

To a solution of 1.3 (740 mg, 2.43 mmol) in THE (20 mL), bromo (ethenyl) magnesium (17.2 mL, 0.7M, 12.1 mmol) was added at 0° C. After the mixture was stirred at 25° C. for 2 h, the mixture was poured into $NH_4Cl$ (100 mL, sat.). The mixture was extracted with EtOAc (2×100 mL) and the combined organic phase was washed with water (2×100 mL), brine (200 mL), dried over anhydrous $Na_2SO_4$, filtered and concentrated. The residue was purified by silica gel chromatography (0-20% EtOAc in PE) to give 1.4 (330 mg, 41%).

$^1H$ NMR (400 MHz, $CDCl_3$) $\delta_H$ 5.95-5.78 (m, 1H), 5.27-5.00 (m, 2H), 4.05-3.94 (m, 1H), 2.10-2.05 (m, 1H), 1.97-1.61 (m, 7H), 1.52-1.24 (m, 7H), 1.21-1.19 (m, 3H), 1.13-0.94 (m, 9H), 0.81-0.66 (m, 5H).

Synthesis of 1.5

To a solution of 1.4 (330 mg, 0.9923 mmol) in DCM (10 mL) DMP was added (839 mg, 1.98 mmol) at 40° C. After the mixture was stirred at 40° C. for 1 h, the mixture was added to $NaHCO_3$ (50 mL, sat.) and $Na_2S_2O_3$ (50 mL, sat.). The aqueous phase was extracted with DCM (2×50 mL) and the combined organic phase was washed with $NaHCO_3$/$Na_2S_2O_3$ (1:1, 2×100 mL, sat.), brine (100 mL), dried over anhydrous $Na_2SO_4$, filtered and concentrated to give 1.5 (350 mg).

$^1H$ NMR (400 MHz, $CDCl_3$) $\delta_H$ 6.49-6.37 (m, 1H), 6.25-6.16 (m, 1H), 5.70-5.63 (m, 1H), 2.80 (t, 1H), 1.89-1.64 (m, 8H), 1.37-1.24 (m, 5H), 1.45-1.22 (m, 1H), 1.20 (s, 3H), 1.12-0.95 (m, 7H), 0.79-0.62 (m, 3H), 0.59 (s, 3H).

Synthesis of 1

A solution of 1.5 (350 mg, 1.05 mmol), 1-methyl-1H-imidazole (255 mg, 3.15 mmol) and 1H-pyrazole-4-carbonitrile (195 mg, 2.10 mmol) in DMSO (10 mL) was stirred at 70° C. for 16 h. The mixture was added into saturated brine (50 mL) and the aqueous layer was extracted with EtOAc (2×50 mL). The combined organic layer was washed with saturated brine (2×50 mL), dried over anhydrous $Na_2SO_4$, filtered and concentrated. The residue was purified by silica gel chromatography (0-50% EtOAc in PE) and prep-HPLC (Column: Welch Xtimate C18 150*25 mm*5 um; Condition: water (0.225% FA)-MeOH; Begin B: 64; End B: 94; Gradient Time (min): 8.5; 100% B Hold Time (min): 2; Flow Rate (ml/min): 30; Injections: 8) to give 1 (84.5 mg, 19%).

$^1H$ NMR (400 MHz, $CDCl_3$) $\delta_H$ 7.91 (s, 1H), 7.75 (s, 1H), 4.52-4.44 (m, 1H), 4.40-4.33 (m, 1H), 3.11-3.01 (m, 1H), 2.93-2.83 (m, 1H), 2.47 (t, 1H), 2.18-2.07 (m, 1H), 1.95-1.56 (m, 9H), 1.44-1.27 (m, 4H), 1.20 (s, 3H), 1.16-0.94 (m, 8H), 0.74-0.59 (m, 2H), 0.41 (s, 3H). LC-ELSD/MS: purity 99%; MS ESI calcd. $C_{26}H_{38}N_3O_2$ $[M+H]^+$ 424.4, found 424.4.

Example 2: Synthesis of 1-(3-((3R,5S,8R,9R,10S,13S,14S,17S)-3-hydroxy-3-(methoxymethyl)-13-methylhexadecahydro-1H-cyclopenta[a]phenanthren-17-yl)-3-oxopropyl)-1H-pyrazole-4-carbonitrile (2)

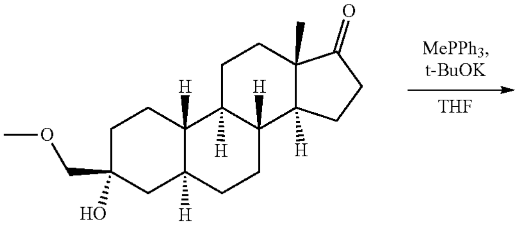

2.0

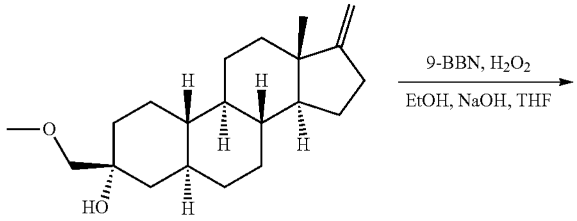

2.1

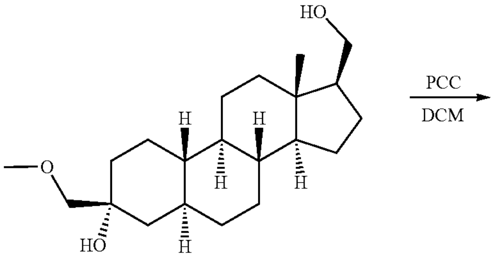

2.2

-continued

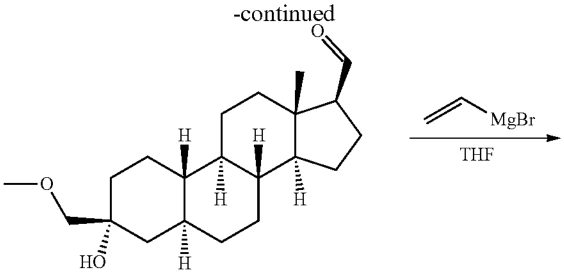

2.3

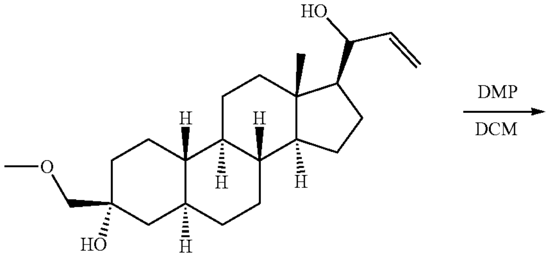

2.4

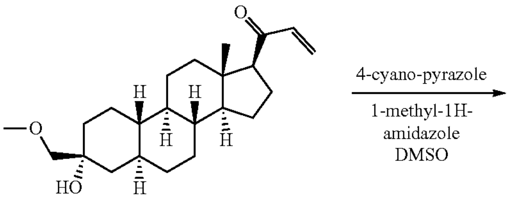

2.5

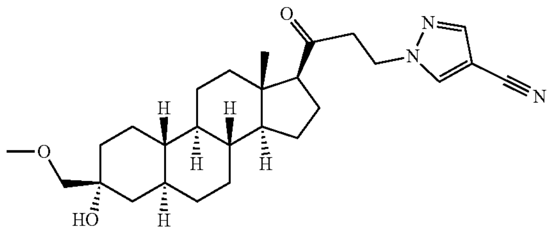

2

Synthesis of 2.1

To a mixture of $MePPh_3Br$ (22.2 g, 62.4 mmol) in THE (150 mL) was added t-BuOK (7.0 g, 48.4 mmol) at 25° C. under $N_2$. The resulting mixture was stirred at 50° C. for 30 min. Compound 2.0 (10.0 g, 31.2 mmol) was added in portions below 50° C. After stirring at 50° C. for 16 h a yellow suspension was observed. The reaction mixture was quenched with 10% $NH_4Cl$ aqueous (150 mL) at 25° C. and the aqueous phase was extracted with EtOAc (2×150 mL). The combined organic phase was separated, dried over $Na_2SO_4$, filtered and concentrated, which was purified by trituration with $MeOH/H_2O$ (1:1, 400 mL) at reflux to give 2.1 (11.1 g).

$^1H$ NMR (400 MHz, $CDCl_3$) $\delta_H$ 4.65-4.59 (m, 2H), 3.42-3.35 (m, 3H), 3.19 (s, 2H), 2.53-2.42 (m, 1H), 2.28-2.16 (m, 1H), 2.00 (s, 1H), 1.89-1.65 (m, 6H), 1.50-1.36 (m, 1H), 1.34-0.83 (m, 12H), 0.78 (s, 3H), 0.75-0.67 (m, 2H).

Synthesis of 2.2

To a solution of 2.1 (11.1 g, 34.8 mmol) in anhydrous THE (150 mL) was added 9-BBN dimer (16.9 g, 69.6 mmol)

at 25° C. under $N_2$. The reaction mixture was stirred at 25° C. for 18 h. To the resulting mixture ethanol was added (24.6 mL, 417 mmol) at 25° C., followed by aqueous NaOH (83.4 mL, 5.0 M, 417 mmol) and $H_2O_2$ (41.7 mL, 10 M, 417 mmol) dropwise at 0° C. After stirring at 80° C. for 3 h the mixture was cooled and subsequently poured into $Na_2S_2O_3$ (300 mL, sat. aq.). The aqueous phase was extracted with EtOAc (2×200 mL). The combined organic phase was washed with saturated brine (200 mL), dried over anhydrous $Na_2SO_4$, filtered and concentrated in vacuum. The residue was purified by flash column (15-25% EtOAc in PE) to give 2.2 (8.6 g, 73.5%).

$^1$H NMR (400 MHz, $CDCl_3$) $\delta_H$ 3.75-3.68 (m, 1H), 3.38 (s, 3H), 3.18 (s, 2H), 2.03-1.93 (m, 1H), 1.86-1.69 (m, 6H), 1.66-1.62 (m, 2H), 1.48-1.33 (m, 2H), 1.29-1.14 (m, 6H), 1.12-1.04 (m, 4H), 1.03-0.96 (m, 3H), 0.77-0.67 (m, 2H), 0.65 (s, 3H).

Synthesis of 2.3

To a mixture of 2.2 (8.6 g, 25.5 mmol) in DCM (100 mL) was added silica gel (8.23 g) and PCC (8.23 g, 38.2 mmol) at 0° C. After stirring at 25° C. for 1 h the mixture was filtered, washed with DCM (2×100 ml) and solvents were evaporated. The residue was purified by column chromatography (15-35% of EtOAc in PE) to give the 2.3 (4.1 g, 48%).

$^1$H NMR (400 MHz, $CDCl_3$) $\delta_H$, 3.38 (s, 3H), 3.18 (s, 2H), 2.44-2.05 (m, 2H), 2.02-1.94 (m, 1H), 1.87-1.58 (m, 9H), 1.52-1.36 (m, 2H), 1.32-0.88 (m, 11H), 0.82-0.65 (m, 5H).

Synthesis of 2.4

To a solution of 2.3 (1.0 g, 2.98 mmol) in THE (5 mL) was added bromo (ethenyl) magnesium (1.95 g, 14.9 mmol) at 0° C. After stirring at 25° C. for 16 h, the mixture was quenched by $NH_4Cl$ (10 mL, sat.) and extracted with EtOAc (2×10 mL). The organic layer was separated, dried over $Na_2SO_4$, filtered, concentrated and purified bf flash column (15~40% EtOAc in PE) to give 2.4 (460 mg, 43%).

$^1$H NMR (400 MHz, $CDCl_3$) $\delta_H$ 5.95-5.75 (m, 1H), 5.27-4.99 (m, 2H), 4.06-3.91 (m, 1H), 3.38 (s, 3H), 3.20-3.15 (m, 2H), 2.21-2.06 (m, 1H), 2.02-1.61 (m, 8H), 1.51-1.33 (m, 3H), 1.29-1.17 (m, 5H), 1.13-0.92 (m, 7H), 0.81-0.64 (m, 5H).

Synthesis of 2.5

To a solution of 2.4 (200 mg, 0.55 mmol) in DCM (2 mL) was added DMP (466 mg, 1.10 mmol) at 25° C. After stirring at 25° C. for 1 h the mixture was added $NaHCO_3$ (10 mL, sat.) and $Na_2S_2O_3$ (10 mL, sat.). The aqueous phase was extracted with DCM (2×10 mL) and the combined organic phase was washed with $NaHCO_3$/$Na_2S_2O_3$ (1:1, 2×10 mL, sat.), brine (10 mL), dried over anhydrous $Na_2SO_4$, filtered, and concentrated to give 2.5 (140 mg, 71%).

$^1$H NMR (400 MHz, $CDCl_3$) $\delta_H$ 6.48-6.36 (m, 1H). 6.23-6.15 (m, 1H), 5.72-5.62 (m, 1H), 3.38 (s, 3H), 3.18 (s, 2H), 2.85-2.73 (m, 1H), 2.31-2.17 (m, 1H), 1.91-1.64 (m, 8H), 1.45-1.35 (m, 2H), 1.30-1.15 (m, 5H), 1.13-0.93 (m, 6H), 0.77-0.65 (m, 2H), 0.59 (s, 3H).

Synthesis of 2

A solution of 2.5 (140 mg, 0.39 mmol), 1-methyl-1H-imidazole (95.2 mg, 1.16 mmol) and 1H-pyrazole-4-carbonitrile (72.2 mg, 0.7766 mmol) in DMSO (5 mL) was stirred at 70° C. for 16 h. The mixture was added into saturated brine (10 mL) and the aqueous layer subsequently extracted with EtOAc (3×10 mL). The combined organic layer was washed with saturated brine (2×10 mL), dried over anhydrous $Na_2SO_4$, filtered and concentrated to give crude 2 (60 mg). The crude 2 (60 mg) was purified by SFC (DAICEL CHIRALCEL OJ-H (250 mm*30 mm, Sum)); Mobile phase: A: $CO_2$ B: 0.1% $NH_3H_2O$ EtOH; gradient: from 25% to 25% of B, FlowRate (ml/min): 60) to give 2 (10.6 mg).

$^1$H NMR (400 MHz, $CDCl_3$) $\delta_H$ 7.91 (s, 1H), 7.75 (s, 1H), 4.52-4.43 (m, 1H), 4.40-4.32 (m, 1H), 3.38 (s, 3H), 3.18 (s, 2H), 3.11-3.01 (m, 1H), 2.92-2.84 (m, 1H), 2.51-2.44 (m, 1H), 2.18-2.05 (m, 1H), 2.03-1.99 (m, 1H), 1.85-1.70 (m, 4H), 1.66-1.59 (m, 3H), 1.44-1.33 (m, 2H), 1.27-1.14 (m, 5H), 1.10-0.91 (m, 6H), 0.75-0.63 (m, 2H), 0.41 (s, 3H). LC-ELSD/MS purity 99%, MS ESI calcd. for $C_{27}H_{39}N_3O_3$ $[M+H]^+$ 454.3, found 454.3.

Example 3: Synthesis of 1-(4-((3R,5R,8R,9R,10S,13S,14S,17S)-3-hydroxy-3,13-dimethylhexadecahydro-1H-cyclopenta[a]phenanthren-17-yl)-4-oxobutyl)-1H-pyrazole-4-carbonitrile (3)

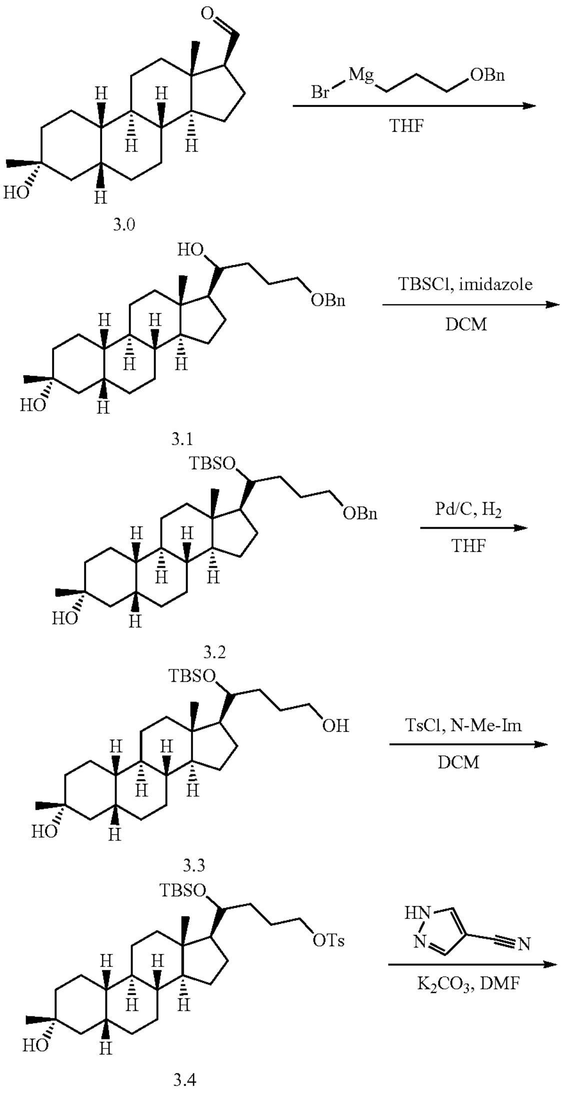

-continued

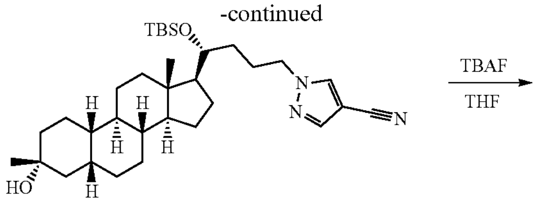

3.5

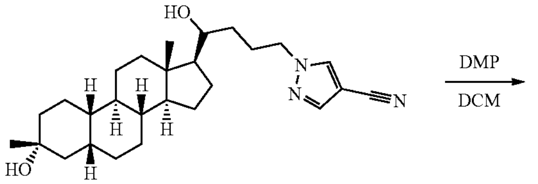

3.6

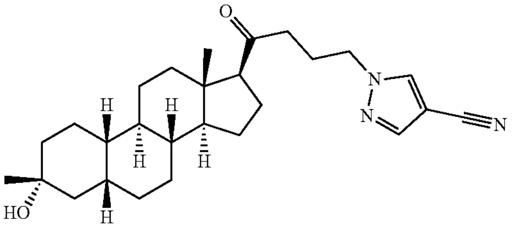

3

Synthesis of 3.1

To a suspension of Mg (2.52 g, 105 mmol) and $I_2$ (20 mg) in THE (10 mL) was added solution of 1-bromo-3-benzyloxypropane (12.0 g, 52.5 mmol) in THE (40 mL) dropwise under $N_2$ at 35-40° C. The mixture was stirred at 35° C. for 1 h. To the fresh prepared Grignard reagent, a solution of 3.0 (1.6 g, 3.28 mmol) in THE (20 mL) was added at 10° C. After stirring at 25° C. for 1 h the mixture was quenched by $NH_4Cl$ (40 mL, sat.) and extracted with EtOAc (100 mL). The organic layer was separated, dried over $Na_2SO_4$, filtered, concentrated and purified by flash column (15~40% EtOAc in PE) to give 3.1 (2.3 g, 97%).

Synthesis of 3.2

To a solution of 3.1 (2.3 g, 5.05 mmol) in DMF (10 mL) was added imidazole (687 mg, 10.1 mmol) and TBSCl (1.14 g, 7.57 mmol). After stirring at 50° C. for 8 h, the mixture was quenched by water (20 mL) and extracted with EtOAc (20 mL). The organic layer was separated, dried over $Na_2SO_4$, filtered, concentrated and purified by flash column (0-10% EtOAc in PE) to give 3.2 (1.3 g, 45%).

Synthesis of 3.3

To a solution of 3.2 (500 mg, 0.8787 mmol) in THE (20 mL) Pd/C (100 mg, wet, 10%) was added under $N_2$. After stirring under $H_2$ (20 psi) at 25° C. for 20 h, the mixture was filtered though a pad of celite and washed with THF (3×50 mL). The combined filtrate was concentrated to give 3.3 (400 mg).

Synthesis of 3.4

To a solution of 3.3 (400 mg, 0.83 mmol) in DCM (5 mL) was added N-methylimidazole (102 mg, 1.25 mmol), TEA (252 mg, 2.50 mmol) and TsCl (318 mg, 1.67 mmol). After stirring at 25° C. for 0.5 h the mixture was poured into water (20 mL). The aqueous phase was extracted with EtOAc (2×30 mL). The combined organic phase was washed with water (2×20 mL), dried over anhydrous $Na_2SO_4$, filtered and concentrated to give 3.4 (600 mg).

Synthesis of 3.5

To a solution of 3.4 (600 mg, 0.9478 mmol) in DMF (10 mL) was added $Cs_2CO_3$ (619 mg, 1.89 mmol) and 4-cyanopyrazole (175 mg, 1.89 mmol). After stirring at 80° C. for 16 h the mixture was diluted with EtOAc (2×30 mL) and washed with water (30 mL), LiCl (5%, 30 mL aq.), dried over $Na_2SO_4$, filtered and purified by flash column (5~30% EtOAc in PE)) to give 3.5 (400 mg, 76%).

Synthesis of 3.6

To a solution of 3.5 (400 mg, 0.7221 mmol) in THE (1 mL) was added TBAF (7.22 mL, 1 M in THF, 7.22 mmol, domestic). After stirring at 25° C. for 48 h the mixture was concentrated under vacuum. The residue was dissolved in EtOAc (50 mL), washed with water (2×30 mL), brine (30 mL), dried over $Na_2SO_4$, filtered, concentrated under vacuum to give crude 3.6 (360 mg).

Synthesis of 3

To a mixture of 3.6 (360 mg, 0.82 mmol) in DCM (5 mL) was added DMP (691 mg, 1.63 mmol) at 25° C. After stirring at 20° C. for 3 h the mixture was added $NaHCO_3$ (10 mL, sat.) and $Na_2S_2O_3$ (10 mL, sat.). The aqueous phase was extracted with DCM (2×30 mL) and the combined organic phase was washed with $NaHCO_3/Na_2S_2O_3$ (1:1, 2×40 mL, sat.), brine (30 mL), dried over anhydrous $Na_2SO_4$, filtered and concentrated. The residue was purified by column chromatography (15-35% of EtOAc in PE) to give the 3 (118.7 mg, 33%).

$^1H$ NMR (400 MHz, $CDCl_3$) $\delta_H$ 7.82-7.75 (m, 2H), 4.20 (t, 2H), 2.52-2.43 (m, 1H), 2.40-2.32 (m, 2H), 2.20-2.08 (m, 3H), 1.89-1.59 (m, 8H), 1.49-1.31 (m, 8H), 1.27 (s, 4H), 1.25-0.97 (m, 6H), 0.58 (s, 3H) LC-ELSD/MS purity>99%, MS ESI calcd. for $C_{27}H_{38}N_3O$ $[M-H_2O+H]^+$ 420.2, found 420.2.

Example 4: Synthesis of 1-(5-((3R,5R,8R,9R,10S,13S,14S,17S)-3-hydroxy-3,13-dimethylhexadecahydro-1H-cyclopenta[a]phenanthren-17-yl)-5-oxopentyl)-1H-pyrazole-4-carbonitrile (4)

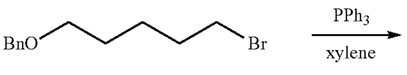

4.0

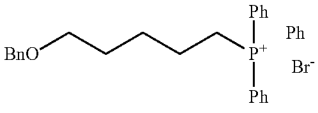

4.1

-continued

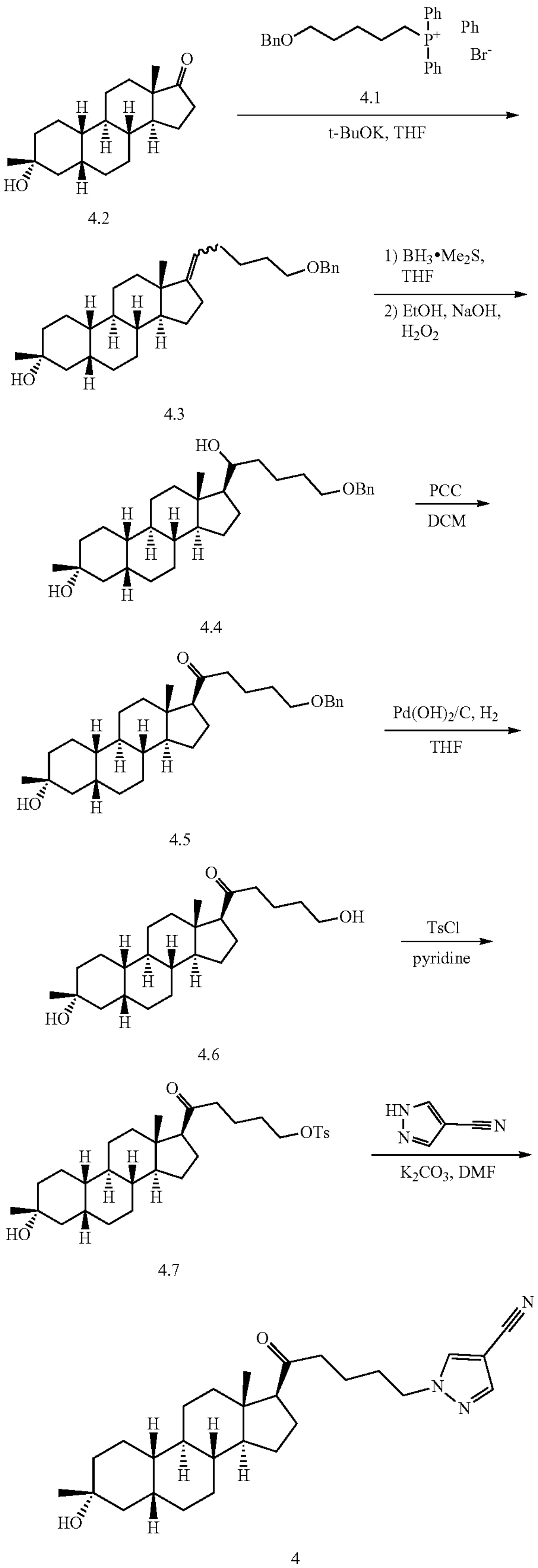

4.2

4.3

4.4

4.5

4.6

4.7

4

Synthesis of 4.1

To a solution of 4.0 (5 g, 19.4 mmol) in xylene (20 mL) was added $PPh_3$ (5.58 g, 21.3 mmol). After stirring at 120° C. for 40 h the clear xylene layer was separated and discarded. The residue was triturated in DCM (20 mL) and filtered. The filtrate was concentrated and purified by flash chromatography (0~4% MeOH in DCM) to give 4.1 (7 g, 70%).

$^1$H NMR (400 MHz, $CDCl_3$) $\delta_H$ 7.90-7.60 (m, 18H), 7.35-7.25 (m, 2H), 4.42 (s, 2H), 3.95-3.80 (m, 2H), 3.45 (t, 2H), 1.80-1.60 (m, 6H).

Synthesis of 4.3

To a solution of 4.1 (7 g, 13.4 mmol) in THE (30 mL) was added t-BuOK (1.49 g, 13.3 mmol) under $N_2$ and the mixture was stirred at 50° C. for 1 h. To this was added 4.2 (3.0 g, 10.3 mmol) and the reaction mixture stirred at 50° C. for a further 16 h. The mixture was quenched with $NH_4Cl$ (20 mL, sat.) and extracted with EtOAc (2×50 mL). The combined organic layer was dried over $Na_2SO_4$, filtered, concentrated in vacuum and purified by flash column (0~10% EtOAc in PE) to give 4.3 (300 mg, 6%).

$^1$H NMR (400 MHz, $CDCl_3$) $\delta_H$ 7.40-4.30 (m, 5H), 5.00 (t, 1H), 4.50 (s, 2H), 3.47 (t, 2H), 2.40-2.30 (m, 1H), 2.20-1.95 (m, 4H), 1.90-1.75 (m, 3H), 1.75-1.60 (m, 5H), 1.50-1.00 (m, 20H), 0.85 (s, 3H).

Synthesis of 4.4

To a solution of 4.3 (300 mg, 0.66 mmol) in THE (5 mL) was added $BH_3 \cdot Me_2S$ (0.66 mL, 10 M, 6.65 mmol) under $N_2$ and the reaction stirred at 25° C. for 16 h. To the mixture was added EtOH (1.52 g, 33.2 mmol), NaOH (6.6 mL, 5M, 33 mmol) and $H_2O_2$ (0.66 mL, 10 M, 6.6 mmol), and the mixture was further stirred at 20° C. for 1 h. The mixture was quenched by $Na_2SO_3$ (10%, 10 mL) and extracted with EtOAc (2×50 mL). The combined organic layer was dried over $Na_2SO_4$, filtered, concentrated in vacuum and purified by flash column (20~40% EtOAc in PE) to give 4.4 (300 mg, 96%).

Synthesis of 4.5

To a solution of 4.4 (300 mg, 0.64 mmol) in DCM (5 mL) was added silica gel (1.2 g) and PCC (275 mg, 1.28 mmol) and the mixture was stirred at 25° C. for 1 h. The mixture was concentrated and purified by flash column (10~20% EtOAc in PE) to give 4.5 (190 mg, 64%).

Synthesis of 4.6

To a solution of 4.5 (190 mg, 0.41 mmol) in THE (10 mL) was added $Pd(OH)_2$/C (dry, 10%, 0.5 g) under $N_2$. The suspension was degassed under vacuum and purged with $H_2$ three times. The mixture was stirred under $H_2$ (30 psi) at 30° C. for 20 h resulting in a black suspension. The reaction mixture was filtered through a pad of Celite and washed with THF (3×10 mL). The filtrate was concentrated and purified by flash column (25~75% EtOAc in PE) to give 4.6 (100 mg, 65%).

Synthesis of 4.7

To a solution of 4.6 (70 mg, 0.1858 mmol) in DCM (3 mL) was added N-methylimidazole (45.7 mg, 0.5574 mmol), TEA (112 mg, 1.11 mmol) and TsCl (141 mg, 0.7432 mmol). After stirring at 25° C. for 3 h the mixture was poured into saturated aq. $NaHCO_3$ solution (20 mL). The aqueous phase was extracted with EtOAc (2×30 mL). The combined organic phase was washed with water (2×20 mL), dried over anhydrous $Na_2SO_4$, filtered and concentrated to give 4.7 (150 mg).

Synthesis of 4

To a solution of 4.7 (150 mg, 0.2826 mmol) in DMF (3 mL) was added $Cs_2CO_3$ (184 mg, 0.5652 mmol), 4-cyano-pyrazole (52.6 mg, 0.5652 mmol), and the mixture stirred at 80° C. for 16 h. The mixture was diluted with EtOAc (2×30 mL) and washed with water (30 mL), LiCl (5%, 30 mL aq.), dried over $Na_2SO_4$, filtered and purified by flash column (5~40% EtOAc in PE) to give crude 4 (50 mg). The 50 mg of crude 4 was purified by SFC (column: DAICEL CHIRALCEL OJ-H (250 mm*30 mm, Sum)); Mobile phase: A: $CO_2$ B: 0.1% $NH_3H_2O$ EtOH; gradient: from 35% to 35% of B, FlowRate (ml/min): 60) to give 4 (32.8 mg, 65.7%).

$^1$H NMR (400 MHz, $CDCl_3$) $\delta_H$ 7.82 (s, 1H), 7.79 (s, 1H), 4.15 (t, 2H), 2.52-2.43 (m, 1H), 2.40 (t, 2H), 2.21-2.10 (m, 1H), 1.95-1.60 (m, 11H), 1.51-1.32 (m, 9H), 1.27 (s, 4H), 1.23-0.99 (m, 6H), 0.58 (s, 3H). LC-ELSD/MS purity>99%, MS ESI calcd. for $C_{29}H_{41}N_3O_2$ $[M+H]^+$ 452.3, found 452.3.

Examples 5 & 6: Synthesis of 1-(3-((3R,5R,8R,9R,10S,13R,14S,17R)-3-hydroxy-3,13-dimethylhexadecahydro-1H-cyclopenta[a]phenanthren-17-yl)-2-oxopropyl)-1H-pyrazole-4-carbonitrile (5) & (3R,5R,8R,9R,10S,13R,14S,17R)-17-(2-hydroxypropyl)-3,13-dimethylhexadecahydro-1H-cyclopenta[a]phenanthren-3-ol (6)

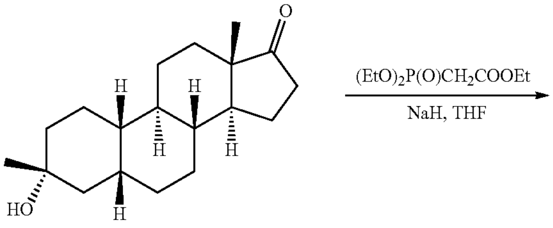

5.0

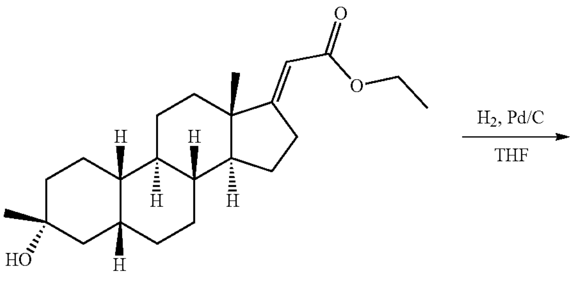

5.1

-continued

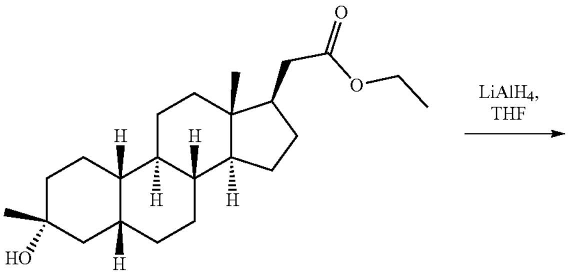

5.2

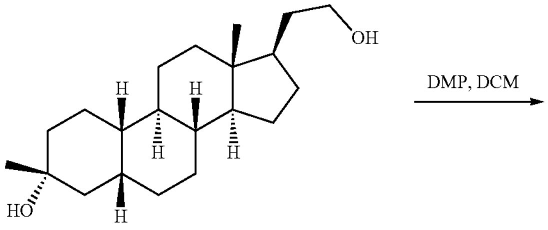

5.3

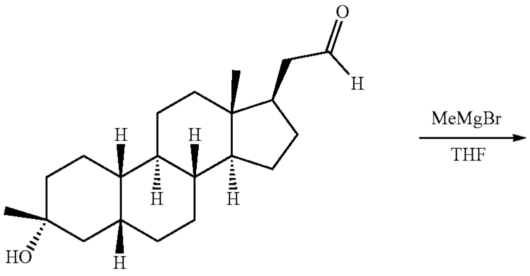

5.4

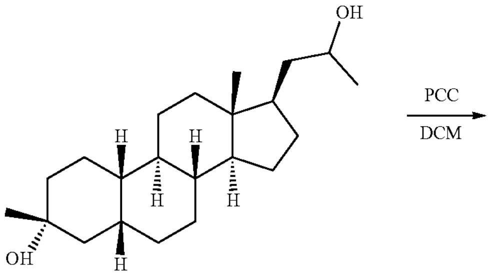

5.5

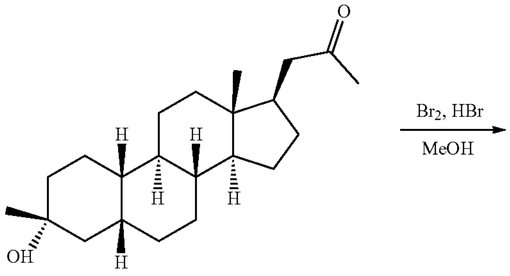

6

-continued

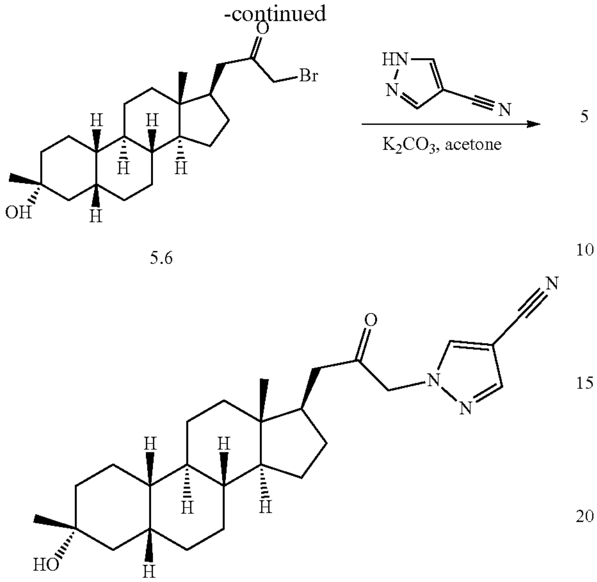

5.6

5

Synthesis of 5.1

To a suspension of NaH (2.75 g, 60% in mineral oil, 68.8 mmol) in THF (60 mL) was added $(EtO)_2P(O)CH_2COOEt$ (15.4 g, 68.8 mmol) dropwise at 0° C. and the mixture was subsequently stirred at 20° C. for 10 min. A solution of 5.0 (10 g, 34.4 mmol) in THF (20 mL) was added dropwise at 20° C. After refluxing at 70° C. for 16 h the mixture was poured into $NH_4Cl$ (200 mL, 10% aq) and extracted with EtOAc (200 mL). The organic layer was separated, dried over $Na_2SO_4$, filtered, concentrated and purified by flash column (0~20% EtOAc in PE) to give 5.1 (12.0 g, 97%).

$^1$H NMR (400 MHz, $CDCl_3$) $\delta_H$ 5.52 (t, 1H), 4.15 (q, 2H), 2.90-2.75 (m, 2H), 1.95-1.60 (m, 5H), 1.50-1.25 (m, 18H), 1.20-1.05 (m, 4H), 0.82 (s, 3H).

Synthesis of 5.2

To a solution of 5.1 (12 g, 33.2 mmol) in THE (150 mL) was added Pd/C (2 g, dry, 10%) under $N_2$. After stirring under $H_2$ (40 psi) at 40° C. for 24 h, the mixture was filtered though a pad of celite and washed with THE (3×50 mL). The combined filtrate was concentrated to give 5.2 (11.7 g, 98%).

$^1$H NMR (400 MHz, $CDCl_3$) $\delta_H$4.11 (q, 2H), 2.35 (dd, 1H), 2.10 (dd, 1H), 2.00-1.75 (m, 6H), 1.70-1.50 (m, 3H), 1.50-1.35 (m, 6H), 1.35-1.25 (m, 10H), 1.20-0.95 (m, 6H), 0.59 (s, 3H).

Synthesis of 5.3

To a suspension of $LiAlH_4$ (6.0 g, 158 mmol) in THF (120 mL) was added a solution of 5.2 (11.1 g, 30.6 mmol) in THF (30 mL) at 0° C. under $N_2$. After stirring at 0° C. for 10 min, water/THF (6 mL/200 mL) was added dropwise followed by NaOH (6 mL, 10% aq.) and water (18 mL). The mixture was filtered, and the precipitate was washed with THE (3×100 mL). The combined filtrate was concentrated and triturated in DCM (50 mL) to give 5.3 (9 g, 92%).

$^1$H NMR (400 MHz, $CDCl_3$) $\delta_H$ 3.75-3.55 (m, 2H), 1.90-1.60 (m, 9H), 1.50-1.15 (m, 16H) 1.15-0.90 (m, 6H), 0.59 (s, 3H).

Synthesis of 5.4

To a solution of 5.3 (3 g, 9.3 mmol) in DCM (80 mL) was added DMP (7.92 g, 18.7 mmol). After stirring at 30° C. for 1 h the mixture was washed twice with a mixed solution of $NaHCO_3$ (160 mL, aq. sat.) and $Na_2S_2O_3$ (80 mL, aq. sat.), dried over $Na_2SO_4$, filtered, concentrated and purified by flash column (10~30% EtOAc in PE) to give 5.4 (2.2 g, 74%).

$^1$H NMR (400 MHz, $CDCl_3$) $\delta_H$ 9.76 (t, 1H), 2.55-2.45 (m, 1H), 2.30-2.20 (m, 1H), 2.00-1.80 (m, 5H), 1.70-1.55 (m, 4H), 1.50-1.20 (m, 13H), 1.30-1.00 (m, 6H), 0.60 (s, 3H).

Synthesis of 5.5

To a solution of 5.4 (4 g, 12.5 mmol) in THE (40 mL) was added MeMgBr (20.8 mL, 7.19 mmol, 3M) at 0° C. After stirring for 1 h at 20° C. a black suspension resulted. The reaction mixture was added into saturated $NH_4Cl$ (100 mL) and the aqueous layer was extracted with EtOAc (3×100 mL). The combined organic layer was washed with saturated brine (100 mL), dried over anhydrous $Na_2SO_4$, filtered and concentrated to give 5.5 (4 g).

$^1$H NMR (400 MHz, $CDCl_3$) δ 3.82-3.72 (m, 1H), 1.94-1.59 (m, 12H), 1.54-1.31 (m, 8H), 1.25-0.97 (m, 14H), 0.64-0.50 (m, 3H).

Synthesis of 6

To a solution of 5.5 (4 g, 11.9 mmol) in DCM (50 mL) was added silica gel (8 g) and PCC (5.11 g, 23.8 mmol) at 20° C. After stirring for 1 h at 20° C. a yellow suspension resulted. The mixture was filtered, and the filter cake was washed with DCM (3×20 mL). The mother liquor was concentrated, and the residue was purified by flash column (0-40% of EtOAc in PE) to give 6 (2.3 g, 58%).

$^1$H NMR (400 MHz, $CDCl_3$) δ 2.53-2.44 (m, 1H), 2.27-2.18 (m, 1H), 2.17-2.10 (m, 3H), 1.82-1.74 (m, 3H), 1.69-1.57 (m, 7H), 1.48-1.38 (m, 5H), 1.34-1.25 (m, 6H), 1.19-0.97 (m, 7H), 0.58 (s, 3H). LC-ELSD/MS purity 99%, MS ESI calcd. for $C_{22}H_{35}O$ $[M-H_2O+H]^+$ 315.2, found 315.2.

Synthesis of 5.6

To a solution of 6 (200 mg, 0.6014 mmol) and HBr (5.99 mg, 0.03007 mmol, 40%) in MeOH (10 mL) was added $Br_2$ (105 mg, 0.6615 mmol) at 0° C. After stirring at 25° C. for 2 h the mixture was added into saturated $NaHCO_3$ (20 mL). The aqueous layer was extracted with EtOAc (3×20 mL) and the combined organic layer was washed with saturated brine (30 mL), dried over anhydrous $Na_2SO_4$, filtered and concentrated to give 5.6 (247 mg).

Synthesis of 5

To a solution of 5.6 (240 mg, 0.5833 mmol) in acetone (5 ml) was added $K_2CO_3$ (160 mg, 1.16 mmol) and 1H-pyrazole-4-carbon (81.4 mg, 0.8749 mmol). After stirring at 25° C. for 2 h the reaction mixture was poured into water and subsequently extracted with EtOAc (2×20 ml). The organic phase was dried over anhydrous $Na_2SO_4$, filtered and concentrated to provide the crude product which was purified by flash column (0-40% of EtOAc in PE) to give product 5 (200 mg). The crude product was purified by prep-HPLC (Column: YMC Triart C18 150*25 mm*5 um; Condition: water (10 mM $NH_4HCO_3$)-ACN; Begin B: 70; End B: 100);

Gradient Time (min): 9.5; 100% B Hold Time (min): 2) to give product 5 (100 mg, 50%).

$^1$H NMR (400 MHz, $CDCl_3$) δ 7.90-7.76 (m, 2H), 5.09-4.91 (m, 2H), 2.61-2.49 (m, 1H), 2.39-2.18 (m, 1H), 2.03-1.75 (m, 5H), 1.68-1.58 (m, 6H), 1.42-1.37 (m, 4H), 1.33-0.93 (m, 13H), 0.59 (s, 3H). LC-ELSD/MS purity>99%, MS ESI calcd. for $C_{26}H_{36}N_3O$ $[M-H_2O+H]^+$ 406.3, found 406.3.

Example 7: Synthesis of 1-(4-((3R,5R,8R,9R,10S,13R,14S,17R)-3-hydroxy-3,13-dimethylhexadecahydro-1H-cyclopenta[a]phenanthren-17-yl)-2-methyl-3-oxobutan-2-yl)-1H-pyrazole-4-carbonitrile (7)

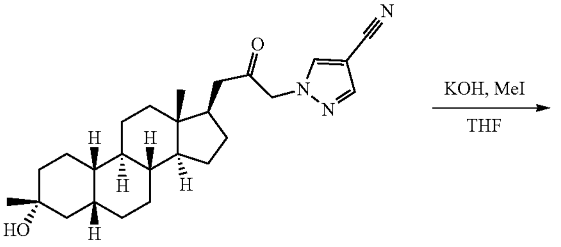

5

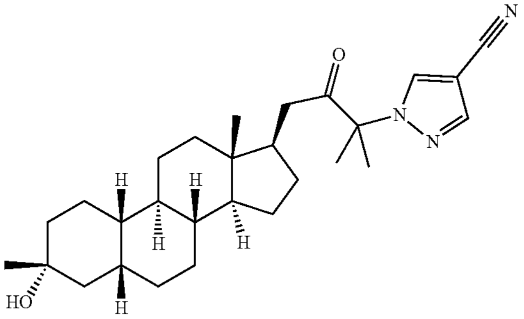

7

Synthesis of 7

To a solution of 5 (200 mg, 0.47 mmol) in THE (2.0 mL) was added KOH (52.8 mg, 0.94 mmol) and MeI (134 mg, 0.94 mmol) at 25° C. After stirring at 25° C. for 2 h the reaction mixture was treated with water (50 mL) and extracted with EtOAc (3×30 mL). The organic phase was washed with brine (100 mL), dried over anhydrous $Na_2SO_4$ and concentrated under vacuum. The residue was purified by flash column (0~40% of EtOAc in PE) to afford 7 (100 mg). 100 mg of impure 7 was purified by HPLC (Column: Phenomenex Gemini-NX 80*40 mm*3 um; Conditions: water (0.05% $NH_3H_2O$+10 mM $NH_4HCO_3$)-ACN; Begin B: 60; End B: 90) to afford 7 (18.5 mg, 19%).

$^1$H NMR (400 MHz, $CDCl_3$) $\delta_H$ 7.98 (s, 1H) 7.88 (s, 1H) 2.13-2.21 (m, 1H) 1.77-1.93 (m, 5H) 1.75 (d, 6H) 1.59-1.65 (m, 3H) 1.27-1.50 (m, 10H) 1.25 (s, 3H) 0.91-1.17 (m, 8H) 0.43 (s, 3H). LC-ELSD/MS: purity 99%, analytic SFC: 100% de; MS ESI calcd. for $C_{28}H_{41}N_3O_2$ $[M-H_2O+H]^+$ 434.3, found 434.3.

Examples 8 & 9: Synthesis of 1-((R)-4-((3R,5R,8R,9R,10S,13R,14S,17R)-3-hydroxy-3,13-dimethylhexadecahydro-1H-cyclopenta[a]phenanthren-17-yl)-3-oxobutan-2-yl)-1H-pyrazole-4-carbonitrile (8) & 1-((S)-4-((3R,5R,8R,9R,10S,13R,14S,17R)-3-hydroxy-3,13-dimethylhexadecahydro-1H-cyclopenta[a]phenanthren-17-yl)-3-oxobutan-2-yl)-1H-pyrazole-4-carbonitrile (9)

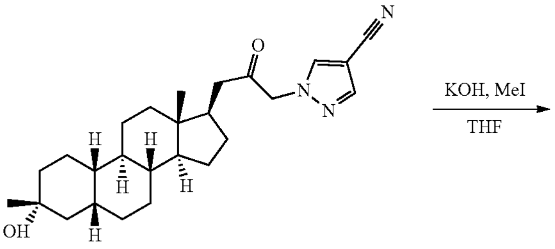

5

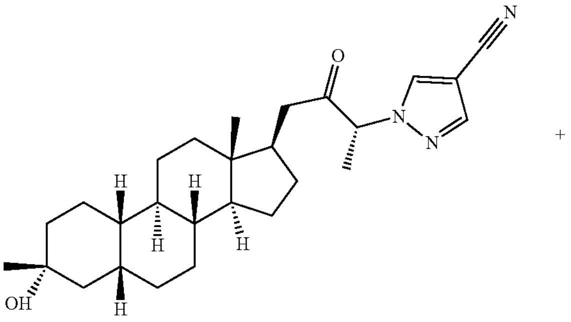

8

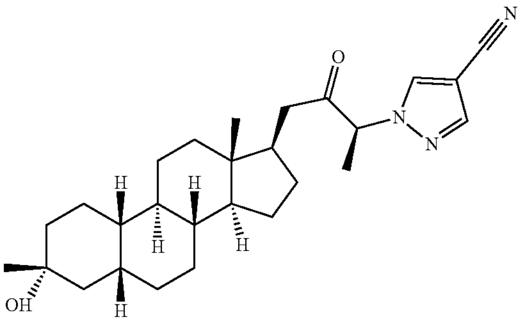

9

Synthesis of 8 & 9

To a solution of 5 (400 mg, 0.94 mmol) in THE (10 mL) was added KOH (63.2 mg, 1.13 mmol) and MeI (200 mg, 1.41 mmol) at 25° C. After stirring at 25° C. for 2 h the reaction mixture was treated with water (20 mL) and extracted with EtOAc (3×10 mL). The organic phase was washed with brine (50 mL), dried over anhydrous $Na_2SO_4$ and concentrated under vacuum. The residue was purified by flash column (0~60% of EtOAc in PE) to afford mixture 8 and 9 (120 mg). The mixture product (120 mg) was purified by SFC (Column: DAICEL CHIRALPAK AD (250 mm*30 mm, 10 um; Condition: 0.1% $NH_3H_2O$ IPA); Begin B: 45; End B: 45) to give 8 (50 mg, 12%) and 9 (40 mg, 9.6%).

$^1$H NMR (400 MHz, $CDCl_3$) δ 7.99-7.79 (m, 2H), 5.19-5.02 (m, 1H), 2.52-2.43 (m, 1H), 2.24-2.15 (m, 1H), 1.94-

1.68 (m, 8H), 1.65-1.57 (m, 6H), 1.54-1.26 (m, 10H), 1.14-0.94 (m, 7H), 0.53 (s, 3H) LC-ELSD/MS: purity>99%, MS ESI calcd. for $C_{27}H_{38}N_3O$ $[M-H_2O+H]^-$ 454.3 found 454.3.

$^1$H NMR (400 MHz, $CDCl_3$) δ 7.99-7.77 (m, 2H), 5.18-5.03 (m, 1H), 2.50-2.37 (m, 1H), 2.24-2.13 (m, 1H), 1.93-1.58 (m, 12H), 1.50-1.23 (m, 12H), 1.15-0.94 (m, 7H), 0.52 (s, 3H).

Examples 10 & 11: Synthesis of 1-((S)-3-((3R,5R,8R,9R,10S,13S,14S,17R)-3-hydroxy-3,13-dimethylhexadecahydro-1H-cyclopenta[a]phenanthren-17-yl)-2-oxobutyl)-1H-pyrazole-4-carbonitrile (10) & 1-((R)-3-((3R,5R,8R,9R,10S,13S,14S,17R)-3-hydroxy-3,13-dimethylhexadecahydro-1H-cyclopenta[a]phenanthren-17-yl)-2-oxobutyl)-1H-pyrazole-4-carbonitrile (11)

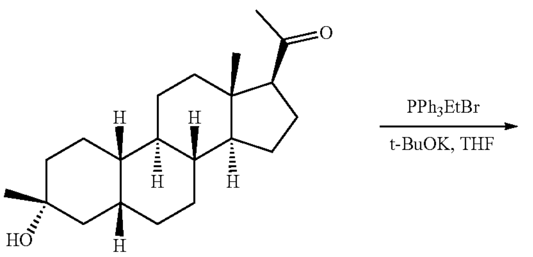

10.0

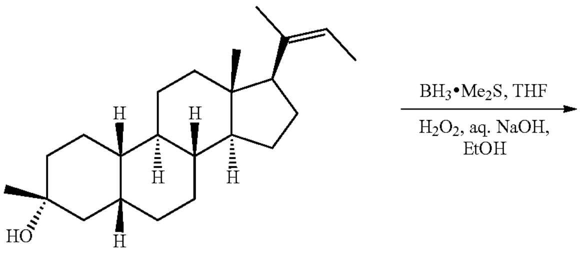

10.1

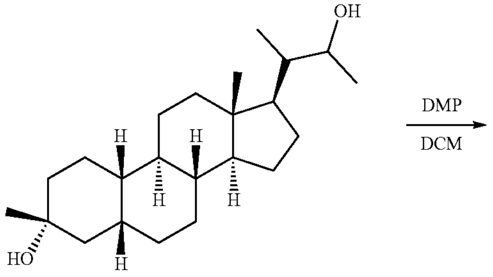

10.2

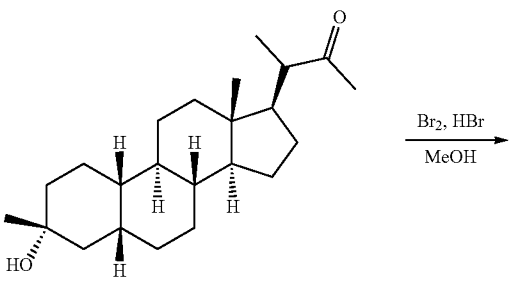

10.3

-continued

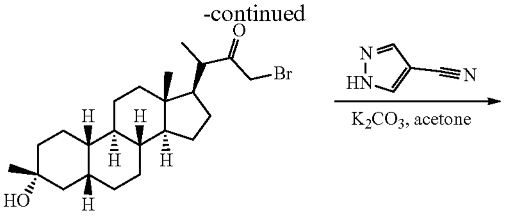

10.4

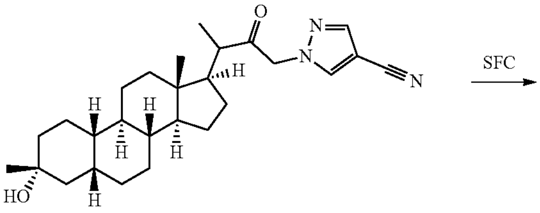

10.5

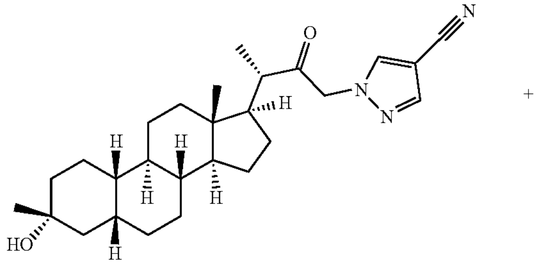

10

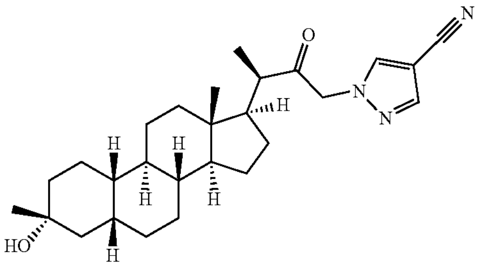

11

Synthesis of 10.1

To a mixture of $PPh_3EtBr$ (15.6 g, 42.3 mmol) in THF (65 mL) was added t-BuOK (4.74 g, 42.3 mmol) at 25° C. under $N_2$. The resulting mixture was stirred at 40° C. for 1 h. 10.0 (4.5 g, 14.1 mmol) in THE (5 mL) was added in portions below 50° C. After stirring at 40° C. for 12 h, the reaction mixture was poured into water (100 mL) at 25° C. The aqueous phase was extracted with EtOAc (2×100 mL), the organic layer was washed with water (100 mL), brine (100 mL), dried over $Na_2SO_4$, filtered and concentrated under vacuum and the residue was purified by silica gel chromatography (0-10% EtOAc in PE) to give 10.1 (4.0 g, 86%). $^1$H NMR (400 MHz, $CDCl_3$) $\delta_H$ 5.47-5.21 (m, 1H), 2.04-1.97 (m, 1H), 1.90-1.72 (m, 5H), 1.71-1.61 (m, 4H), 1.61-1.53 (m, 6H), 1.49-1.34 (m, 6H), 1.33-1.27 (m, 2H), 1.26 (s, 4H), 1.22-0.98 (m, 6H), 0.71-0.50 (m, 3H).

Synthesis of 10.2

To a solution of 10.1 (4.0 g, 12.1 mmol) in THE (80 mL) was added $BH_3$ $Me_2S$ (3.63 mL, 36.3 mmol, 10 M) and the reaction mixture stirred at 15° C. for 20 h. To the resulting mixture ethanol (6.27 mL, 108 mmol) was added at 15° C., followed by aqueous NaOH (21.6 mL, 5.0 M, 108 mmol) at 0° C. Hydrogen peroxide (10.8 mL, 10 M, 108 mmol) was added dropwise at 0° C. and the reaction mixture was stirred at 70° C. for 1 h. The mixture was cooled to 15° C. and $Na_2S_2O_3$ (100 mL, sat. aq.) was added. The aqueous phase was extracted with EtOAc (2×100 mL) and the combined organic phase washed with saturated brine (2×100 mL), dried over anhydrous $Na_2SO_4$, filtered to give 10.2 (2.8 g).

$^1$H NMR (400 MHz, $CDCl_3$) $\delta_H$ 4.13-4.05 (m, 1H), 3.95-3.86 (m, 1H), 2.00-1.90 (m, 1H), 1.72-1.54 (m, 7H), 1.48-1.34 (m, 9H), 1.25 (s, 6H), 1.06-1.00 (m, 8H), 0.91-0.89 (m, 2H), 0.85-0.81 (m, 2H), 0.69-0.67 (m, 3H).

Synthesis of 10.3

To a solution of 10.2 (4.6 g, 13.1 mmol) in DCM (50 mL), Dess-martin (11.1 g, 26.2 mmol) was added at 25° C. After stirring at 25° C. for 5 mins the mixture was quenched with saturated $NaHCO_3$ aqueous (50 mL), the DCM phase was separated and washed with saturated $NaHCO_3/Na_2S_2O_3$ aqueous (1:1, 2×50 mL), brine (50 mL), dried over anhydrous $Na_2SO_4$, filtered and concentrated. The residue was purified by flash column (0-30% of EtOAc in PE) to give 10.3 (2.7 g, 60%).

Synthesis of 10.4

To a solution of 10.3 (2.7 g, 7.79 mmol) in MeOH (30 mL), HBr (310 mg, 1.55 mmol, 40%) and $Br_2$ (1.36 g, 8.56 mmol) were added drop wise at 25° C. and the reaction mixture stirred for 4 h. To the mixture $NaHCO_3$ (50 ml, sat. aq.) was added at 25° C. and the aqueous phase was extracted with EtOAc (2×50 mL). The combined organic phase was washed with saturated brine (2×50 mL), dried over anhydrous $Na_2SO_4$, filtered, concentrated to give 10.4 (3.2 g).

$^1$H NMR (400 MHz, $CDCl_3$) $\delta_H$ 4.07 (d, 1H), 3.96 (s, 1H), 2.90-2.70 (m, 1H), 1.90-1.76 (m, 4H), 1.74-1.54 (m, 6H), 1.49-1.30 (m, 8H), 1.26-1.24 (m, 4H), 1.17 (d, 2H), 1.13-1.08 (m, 3H), 1.08-0.84 (m, 4H), 0.72-0.64 (m, 3H).

Synthesis of 10.5

To a solution of 10.4 (3.2 g, 7.52 mmol) in acetone (50 mL) was added 1H-pyrazole-4-carbonitrile (769 mg, 8.27 mmol) and $K_2CO_3$ (3.10 mg, 22.5 mmol). After stirring at 25° C. for 4 h a light-yellow solution was observed. The mixture was diluted with water (50 mL), extracted with EtOAc (2×20 mL) and the combined organic phase was washed with brine (50 mL), dried over anhydrous $Na_2SO_4$, filtered and concentrated. The residue was purified by flash column (0~30% of EtOAc in PE) to give 10.5 (2.4 g, 72.9%).

$^1$H NMR (400 MHz, $CDCl_3$) $\delta_H$ 7.87-7.85 (m, 1H), 7.81 (s, 1H), 5.15-4.92 (m, 2H), 2.66-2.53 (m, 1H), 1.95-1.76 (m, 5H), 1.72-1.57 (m, 6H), 1.51-1.31 (m, 8H), 1.26-1.25 (m, 3H), 1.23-1.19 (m, 2H), 1.16-1.13 (m, 2H), 1.11-0.90 (m, 5H), 0.71-0.65 (m, 3H).

Synthesis of 10 & 11

The 10.5 (2.4 g, 5.48 mmol) was purified by SFC (column: DAICEL CHIRALCEL OD-H (250 mm*30 mm, Sum)); Mobile phase: A: $CO_2$ B: 0.1% $NH_3H_2O$ EtOH; gradient: from 30% to 30% of B, FlowRate (ml/min): 50) to give 10 (1.05 g, 43.9%) and 11 (1.08 g, 45.1%).

$^1$H NMR (400 MHz, $CDCl_3$) $\delta_H$ 7.85 (s, 1H), 7.82 (s, 1H), 5.10-5.05 (m, 1H), 4.97-4.92 (m, 1H), 2.66-2.56 (m, 1H), 1.93-1.88 (m, 1H), 1.87-1.61 (m, 9H), 1.56-1.35 (m, 9H), 1.26 (s, 3H), 1.21 (d, 3H), 1.16-1.03 (m, 6H), 0.70 (s, 3H). LC-ELSD/MS: purity>99%; MS ESI calcd. fr $C_{27}H_{39}N_3O_2$ $[M-H_2O+H]^+$ 420.3, found 420.3.

$^1$H NMR (400 MHz, $CDCl_3$) $\delta_H$ 7.86 (s, 1H), 7.82 (s, 1H), 5.17-5.02 (m, 2H), 2.65-2.55 (m, 1H), 1.94-1.76 (m, 5H), 1.71-1.44 (m, 11H), 1.41-1.29 (m, 7H), 1.15 (d, 3H), 1.10-0.94 (m, 5H), 0.68 (s, 3H). LC-ELSD/MS: purity>99%; MS ESI calcd. for $C_{27}H_{39}N_3O_2$ $[M-H_2O+H]^+$ 420.3, found 420.3.

Example 12: Synthesis of 4-(2-((3R,5R,8R,9R,10S,13R,14S,17R)-3-hydroxy-3,13-dimethylhexadecahydro-1H-cyclopenta[a]phenanthren-17-yl)acetyl)benzonitrile (12)

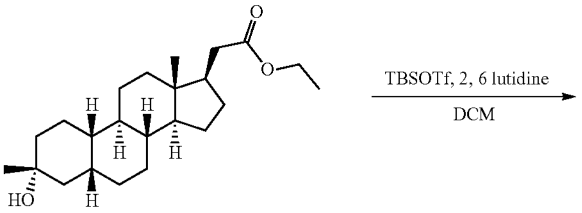

5.2

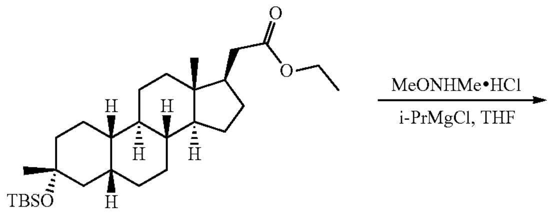

12.1

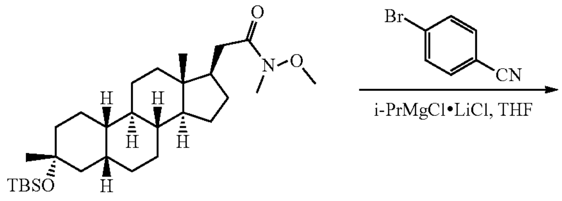

12.2

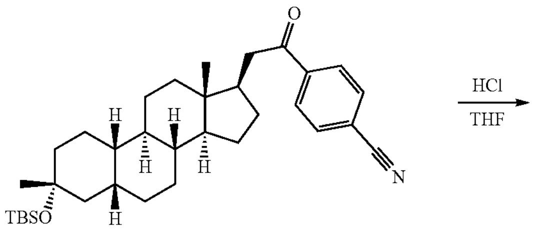

12.3

-continued

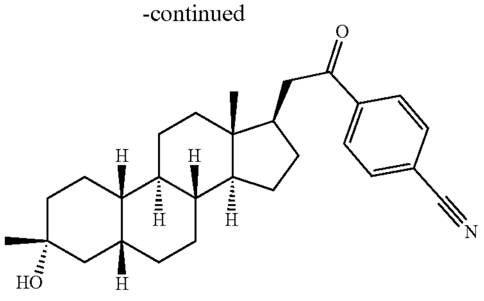

12

Synthesis of 12.1

To a solution of 5.2 (10 g, 27.5 mmol) and 2,6-lutidine (7.35 g, 68.7 mmol) in DCM (100 ml), TBSOTf (14.5 g, 55.0 mmol) was added at 0° C. After stirring at 40° C. for 16 h the mixture was diluted with DCM (50 ml) and washed with water (100 ml). The organic phase was separated, dried over $Na_2SO_4$, filtered and concentrated. The crude product was purified by flash column (0-20% of EtOAc in PE) to give product 12.1 (8 g, 61%).

$^1H$ NMR (400 MHz, $CDCl_3$) δ 4.15-4.10 (m, 2H), 2.43-2.32 (m, 1H), 2.22-2.00 (m, 1H), 1.98-1.53 (m, 9H), 1.48-1.25 (m, 3H), 1.24-1.19 (m, 12H), 1.16-0.98 (m, 6H), 0.86 (s, 9H), 0.59 (s, 3H), 0.07 (m, 6H).

Synthesis of 12.2

To a suspension of 12.1 (7.0 g, 14.6 mmol) and MeNHOMe·HCl (2.13 g, 21.9 mmol) in THF (70 mL) was added i-PrMgCl (2 M in THF, 29.2 mL, 58.4 mmol) at 0° C. under $N_2$. After stirring at 20° C. for 10 mins, $NH_4Cl$ (10% aq., 70 mL) was added. The aqueous layer was extracted with DCM (2×50 mL) and the combined organic layer was washed with saturated brine (50 mL), dried over $Na_2SO_4$, filtered and concentrated under vacuum to give 12.2 (7.7 g).

$^1H$ NMR (400 MHz, $CDCl_3$) δ 3.68 (s, 3H), 3.17 (s, 3H), 2.44-2.54 (m, 1H), 2.16-2.27 (m, 1H), 1.56-1.98 (m, 11H), 1.29-1.44 (m, 6H), 1.22 (s, 3H), 0.95-1.18 (m, 7H), 0.86 (s, 9H) 0.62 (s, 3H), 0.07 (s, 6H).

Synthesis of 12.3

To i-PrMgCl·LiCl (3.03 ml, 3.94 mmol, 1.3 M), 4-bromobenzonitrile (919 mg, 5.05 mmol) was added in THF (5 mL) slowly at 0° C. under $N_2$. After stirring at 20° C. for 2 h a yellow solution was observed. A solution of 12.2 (500 mg, 1.01 mmol) in THF (5 mL) was added dropwise. The mixture was stirred at −75° C. for 1 h and subsequently 20° C. for 1 h. The mixture was added into saturated $NH_4Cl$ (30 mL) and the aqueous layer was extracted with EtOAc (3×20 mL). The combined organic layer was washed with saturated brine (50 mL), dried over anhydrous $Na_2SO_4$, filtered and concentrated. The residue was purified by flash column (0-15% of EtOAc in PE) and then triturated from MeOH/$H_2O$ (8 ml/2 ml) at 20° C. to give 12.3 (400 mg, 74%).

$^1H$ NMR (400 MHz, $CDCl_3$) δ 8.02 (d, 2H) 7.76 (d, 2H) 3.08 (dd, 3.20 Hz, 1H) 2.74 (dd, 9.20 Hz, 1H) 1.58-1.99 (m, 9H) 1.23-1.47 (m, 9H) 1.22 (s, 3H) 0.99-1.17 (m, 6H) 0.85 (s, 9H) 0.68 (s, 3H) 0.07 (s, 6H)

Synthesis of 12

To a mixture of 12.3 (50 mg, 0.09 mmol) in THF (2 mL), HCl (0.5 ml, 3 M, 1.50 mmol) was added at 25° C. and the reaction mixture stirred at 50° C. for 16 h. The mixture was cooled to 25° C., treated with water (30 mL) and subsequently extracted with EtOAc (3×20 mL). The combined organic phase was washed with saturated brine (2×50 mL), dried over anhydrous $Na_2SO_4$, filtered, concentrated and purified by flash column (0~40% of EtOAc in PE) to give 12 (17.9 mg, 46%).

$^1H$ NMR (400 MHz, $CDCl_3$) δ 7.95-8.14 (m, 2H) 7.69-7.85 (m, 2H) 3.06 (dd, 3.60 Hz, 1H) 2.75 (dd, 9.60 Hz, 1H) 1.60-2.01 (m, 9H) 1.27-1.51 (m, 9H) 1.26 (s, 3H) 0.98-1.24 (m, 7H) 0.68 (s, 3H). LC-ELSD/MS 30-90AB_2 min_E, purity 99%, MS ESI calcd. for $C_{28}H_{37}NO_2$ $[M-H_2O+H]^+$ 402.3 found 402.3.

Example 13: Synthesis of 1-(3-((3R,5R,8R,9S,10S,13S,14S,17S)-3-hydroxy-3-(methoxymethyl)-10,13-dimethylhexadecahydro-1H-cyclopenta[a]phenanthren-17-yl)-3-oxopropyl)-1H-pyrazole-4-carbonitrile (13)

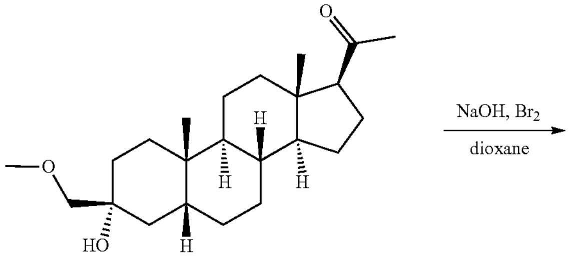

13.0

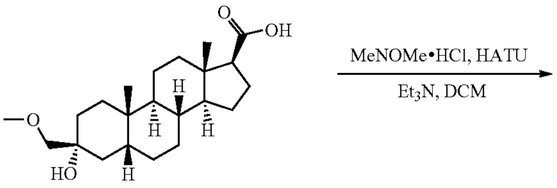

13.1

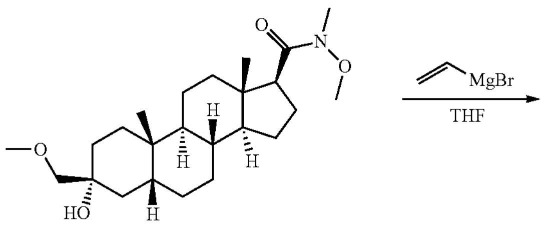

13.2

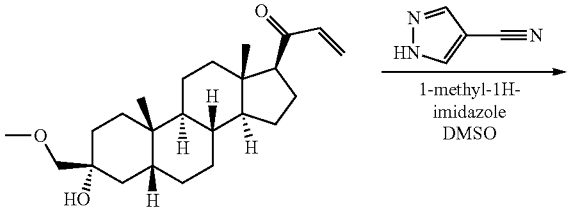

13.3

-continued

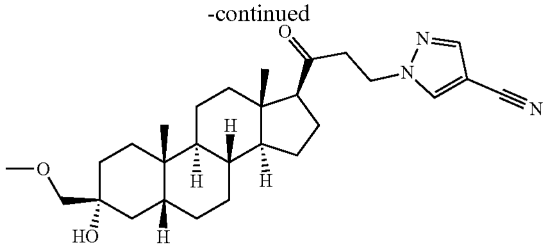

13

Synthesis of 13.1

To a solution of NaOH (28.6 mL, 71.6 mmol, 2.5 M), liquid bromine (2.89 g, 18.1 mmol) was added slowly at 0° C. After stirring at 25° C. for 30 mins a yellow solution was observed. The mixture was slowly added to a stirred solution of 13.0 (2.0 g, 5.51 mmol) in dioxane (20 mL), and further stirred at 25° C. for 16 h. After this time, the remaining oxidizing reagent was quenched by $Na_2SO_3$ aqueous (15 mL). The solution was added aq. HCl and the pH of solution was adjusted to 6 to give a precipitate. The precipitate was filtered, washed with water (3×20 mL) and dried under vacuum to afford 13.1 (1.6 g).

$^1$H NMR (400 MHz, DMSO) $\delta_H$ 11.80 (s, 1H), 4.21 (s, 1H), 3.27-3.17 (m, 5H), 2.27 (t, 1H), 1.96-1.93 (m, 2H), 1.81-1.43 (m, 7H), 1.41-1.20 (m, 6H), 1.17-0.93 (m, 7H), 0.89-0.76 (m, 3H), 0.60 (s, 3H).

Synthesis of 13.2

To a solution of 13.1 (500 mg, 1.37 mmol) in DCM (10 mL) was added HATU (1.04 g, 2.74 mmol) and $Et_3N$ (693 mg, 6.85 mmol) at 25° C. After stirring at 25° C. for 0.5 h, methoxy(methyl)-amine·HCl (398 mg, 4.11 mmol) was added, and the reaction was stirred for a further 5 h at 25° C. The mixture was diluted with water (50 mL) and extracted with DCM (3×100 mL). The combined organic layer was concentrated, and the resultant residue was purified by flash column (0~30% of EtOAc in PE) to give 13.2 (400 mg).

$^1$H NMR (400 MHz, $CDCl_3$) $\delta_H$ 3.64 (s, 3H), 3.42-3.34 (m, 5H), 3.18 (s, 3H), 2.62-2.58 (m, 1H), 2.20-2.12 (m, 1H), 1.95-1.47 (m, 7H), 1.43-1.05 (m, 12H), 1.00-0.80 (m, 6H), 0.71 (s, 3H).

Synthesis of 13.3

To a solution of 13.2 (400 mg, 0.981 mmol) in THE (10 mL) was added bromo(ethenyl)magnesium (9.80 mL, 9.80 mmol, 1M). After stirring at 25° C. for 2 h a yellow suspension resulted. An aqueous solution of $NH_4Cl$ (5 mL) was added dropwise into the reaction mixture and extracted with EtOAc (2×10 mL). The combined organic layer was washed with brine (5 mL), dried over $Na_2SO_4$, filtered and concentrated. The residue was purified by flash column (0~20% of EtOAc in PE) to give 13.3 (300 mg).

$^1$H NMR (400 MHz, $CDCl_3$) $\delta_H$ 6.45-6.38 (m, 1H), 6.21-6.16 (m, 1H), 5.68-5.65 (m, 1H), 3.42-3.35 (m, 5H), 2.79 (t, 1H), 2.61 (s, 1H), 2.29-2.22 (m, 1H), 1.96-1.59 (m, 7H), 1.53-1.14 (m, 13H), 1.02-0.93 (m, 4H), 0.56 (s, 3H).

Synthesis of 13

A solution of 13.3 (300 mg, 0.8 mmol), 1-methyl-1H-imidazole (196 mg, 2.40 mmol) and 1H-pyrazole-4-carbonitrile (147 mg, 1.59 mmol) in DMSO (20 mL) was stirred at 70° C. for 16 h resulting in a yellow suspension. The mixture was added into saturated water (50 mL) and the aqueous layer was extracted with EtOAc (2×100 mL). The combined organic layer was washed with saturated brine (2×100 mL), dried over anhydrous $Na_2SO_4$, filtered and concentrated. The residue was purified by silica gel chromatography (0-50% EtOAc in PE) to give 13 (140.5 mg, 70%).

$^1$H NMR (400 MHz, $CDCl_3$) $\delta_H$ 7.91 (s, 1H), 7.75 (s, 1H), 4.52-4.45 (m, 1H), 4.38-4.32 (m, 1H), 3.41-3.34 (m, 5H), 3.10-3.02 (m, 1H), 2.91-2.84 (m, 1H), 2.62 (s, 1H), 2.46 (t, 1H), 2.15-2.07 (m, 1H), 1.93-1.61 (m, 7H), 1.52-1.11 (m, 13H), 1.01-0.91 (m, 4H), 0.37 (s, 3H). LC-ELSD/MS purity 99%, MS ESI calcd. for $C_{28}H_{42}N_3O_3$ $[M+H]^+$ 468.3 found 468.3.

Example 14: Steroid Inhibition of TBPS Binding

[35S]-t-Butylbicyclophosphorothionate (TBPS) binding assays using rat brain cortical membranes in the presence of 5 mM GABA has been described (Gee et al, J. Pharmacol. Exp. Ther. 1987, 241, 346-353; Hawkinson et al, *Mol. Pharmacol.* 1994, 46, 977-985; Lewin, A. H et al., *Mol. Pharmacol.* 1989, 35, 189-194).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This washing procedure is repeated twice and the pellets are resuspended in 10 volumes of buffer. Aliquots (100 mL) of the membrane suspensions are incubated with 3 nM [35S]-TBPS and 5 mL aliquots of test drug dissolved in dimethyl sulfoxide (DMSO) (final 0.5%) in the presence of 5 mM GABA. The incubation is brought to a final volume of 1.0 mL with buffer. Nonspecific binding is determined in the presence of 2 mM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition ($IC_{50}$) of specific binding and the maximal extent of inhibition ($I_{max}$) are determined for the individual experiments with the same model used for the overall data and then the means±SEM.s of the individual experiments are calculated. Picrotoxin serves as the positive control for these studies as it has been demonstrated to robustly inhibit TBPS binding.

Various compounds are or can be screened to determine their potential as modulators of [35S]-TBPS binding in vitro. These assays are or can be performed in accordance with the above In Table 2 below, A indicates a TBPS $IC_{50}$<0.1 μM, B indicates a TBPS $IC_{50}$ (μM) of 0.1 μM to <1.0 μM, C indicates a TBPS $IC_{50}$ (μM) of >1.0 μM.

TABLE 2

| Example | $IC_{50}$ |
|---|---|
| 1 | A |
| 2 | A |
| 3 | A |
| 4 | A |
| 5 | B |
| 6 | B |
| 7 | B |
| 8 | B |
| 9 | B |
| 10 | A |
| 11 | B |
| 12 | A |
| 13 | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (VI-H):

(VI-H)

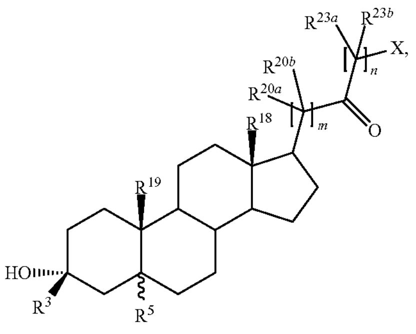

or a pharmaceutically acceptable salt thereof;

wherein:

m is 1, 2, 3, or 4;

n is 0, 1, 2, 3, or 4;

X is

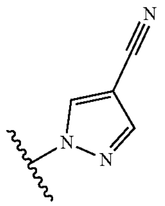 [SMILES: *n1cc(C#N)cn1]

$R^3$ is hydrogen or substituted or unsubstituted alkyl;

$R^5$ is hydrogen or methyl;

$R^{18}$ is substituted or unsubstituted alkyl, substituted or unsubstituted alkenyl, or substituted or unsubstituted alkynyl;

$R^{19}$ is hydrogen or substituted or unsubstituted alkyl; and each of $R^{20a}$, $R^{20b}$, $R^{23a}$, and $R^{23b}$ is independently selected from the group consisting of hydrogen, an unsubstituted alkyl group, a halogenated alkyl group, an unsubstituted alkoxy group, and a halogenated alkoxy group.

2. The compound or pharmaceutically acceptable salt of claim 1, wherein $R^3$ is substituted or unsubstituted alkyl.

3. The compound or pharmaceutically acceptable salt of claim 2, wherein $R^3$ is methyl.

4. The compound or pharmaceutically acceptable salt of claim 1, wherein $R^5$ is hydrogen.

5. The compound or pharmaceutically acceptable salt of claim 1, wherein $R^{18}$ is substituted or unsubstituted $C_{1-6}$ alkyl.

6. The compound or pharmaceutically acceptable salt of claim 5, wherein $R^{18}$ is unsubstituted $C_{1-6}$ alkyl.

7. The compound or pharmaceutically acceptable salt of claim 6, wherein $R^{18}$ is methyl or ethyl.

8. The compound or pharmaceutically acceptable salt of claim 1, wherein $R^{19}$ is unsubstituted $C_{1-6}$ alkyl.

9. The compound or pharmaceutically acceptable salt of claim 8, wherein $R^{19}$ is unsubstituted $C_{1-3}$ alkyl.

10. The compound or pharmaceutically acceptable salt of claim 9, wherein $R^{19}$ is methyl.

11. The compound or pharmaceutically acceptable salt of claim 1, wherein $R^{19}$ is hydrogen.

12. The compound or pharmaceutically acceptable salt of claim 1, wherein each of $R^{20a}$ and $R^{20b}$ is independently hydrogen or an unsubstituted $C_{1-6}$ alkyl group.

13. The compound or pharmaceutically acceptable salt of claim 12, wherein one of $R^{20a}$ and $R^{20b}$ is methyl and the other is hydrogen.

14. The compound or pharmaceutically acceptable salt of claim 12, wherein $R^{20a}$ and $R^{20b}$ are both hydrogen.

15. The compound or pharmaceutically acceptable salt of claim 1, wherein each of $R^{23a}$ and $R^{23b}$ is independently hydrogen or unsubstituted $C_{1-3}$ alkyl.

16. The compound or pharmaceutically acceptable salt of claim 15, wherein one of $R^{23a}$ and $R^{23b}$ is hydrogen and the other is unsubstituted $C_{1-3}$ alkyl.

17. The compound or pharmaceutically acceptable salt of claim 16, wherein one of $R^{23a}$ and $R^{23b}$ is hydrogen and the other is methyl or ethyl.

18. The compound or pharmaceutically acceptable salt of claim 15, wherein both of $R^{23a}$ and $R^{23b}$ are hydrogen.

19. The compound or pharmaceutically acceptable salt of claim 15, wherein both of $R^{23a}$ and $R^{23b}$ are unsubstituted $C_{1-3}$ alkyl.

20. The compound or pharmaceutically acceptable salt of claim 19, wherein each of $R^{23a}$ and $R^{23b}$ is independently selected from methyl or ethyl.

21. The compound or pharmaceutically acceptable salt of claim 20, wherein both of $R^{23a}$ and $R^{23b}$ are methyl.

22. The compound or pharmaceutically acceptable salt of claim 1, wherein the compound of Formula (VI-H) is a compound of Formula (VI-IA):

(VI-IA)

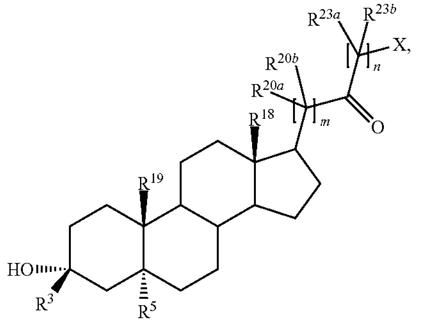

or a pharmaceutically acceptable salt thereof.

23. The compound or pharmaceutically acceptable salt of claim 1, wherein the compound of Formula (VI-H) is a compound of Formula (VI-IB):

(VI-IB)

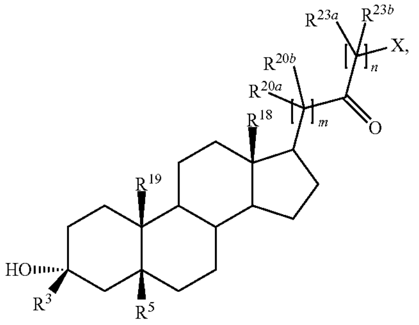

or a pharmaceutically acceptable salt thereof.

24. The compound or pharmaceutically acceptable salt of claim 23, wherein $R^3$ is substituted or unsubstituted alkyl.

25. The compound or pharmaceutically acceptable salt of claim 24, wherein $R^3$ is methyl.

26. The compound or pharmaceutically acceptable salt of claim 23, wherein $R^5$ is hydrogen.

27. The compound or pharmaceutically acceptable salt of claim 23, wherein $R^{18}$ is substituted or unsubstituted $C_{1-6}$ alkyl.

28. The compound or pharmaceutically acceptable salt of claim 27, wherein $R^{18}$ is unsubstituted $C_{1-6}$ alkyl.

29. The compound or pharmaceutically acceptable salt of claim 28, wherein $R^{18}$ is methyl or ethyl.

30. The compound or pharmaceutically acceptable salt of claim 23, wherein $R^{19}$ is unsubstituted $C_{1-6}$ alkyl.

31. The compound or pharmaceutically acceptable salt of claim 30, wherein $R^{19}$ is unsubstituted $C_{1-3}$ alkyl.

32. The compound or pharmaceutically acceptable salt of claim 31, wherein $R^{19}$ is methyl.

33. The compound or pharmaceutically acceptable salt of claim 23, wherein $R^{19}$ is hydrogen.

34. The compound or pharmaceutically acceptable salt of claim 23, wherein each of $R^{20a}$ and $R^{20b}$ is independently hydrogen or an unsubstituted $C_{1-6}$ alkyl group.

35. The compound or pharmaceutically acceptable salt of claim 34, wherein one of $R^{20a}$ and $R^{20b}$ is methyl and the other is hydrogen.

36. The compound or pharmaceutically acceptable salt of claim 34, wherein $R^{20a}$ and $R^{20b}$ are both hydrogen.

37. The compound or pharmaceutically acceptable salt of claim 23, wherein each of $R^{23a}$ and $R^{23b}$ is independently hydrogen or unsubstituted $C_{1-3}$ alkyl.

38. The compound or pharmaceutically acceptable salt of claim 37, wherein one of $R^{23a}$ and $R^{23b}$ is hydrogen and the other is unsubstituted $C_{1-3}$ alkyl.

39. The compound or pharmaceutically acceptable salt of claim 38, wherein one of $R^{23a}$ and $R^{23b}$ is hydrogen and the other is methyl or ethyl.

40. The compound or pharmaceutically acceptable salt of claim 37, wherein both of $R^{23a}$ and $R^{23b}$ are hydrogen.

41. The compound or pharmaceutically acceptable salt of claim 37, wherein both of $R^{23a}$ and $R^{23b}$ are unsubstituted $C_{1-3}$ alkyl.

42. The compound or pharmaceutically acceptable salt of claim 37, wherein each of $R^{23a}$ and $R^{23b}$ is independently selected from methyl or ethyl.

43. The compound or pharmaceutically acceptable salt of claim 41, wherein both of $R^{23a}$ and $R^{23b}$ are methyl.

44. The compound or pharmaceutically acceptable salt of claim 1, wherein the compound of Formula (VI-H) is selected from

5

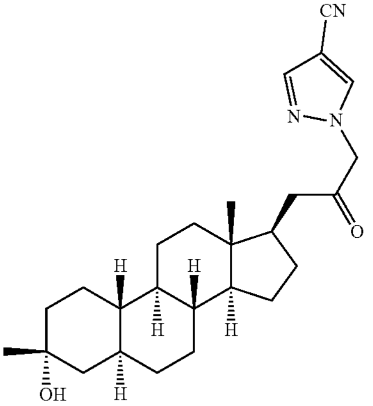

7

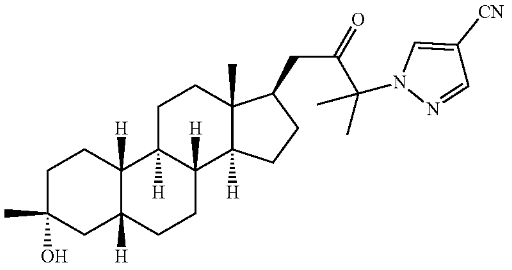

8

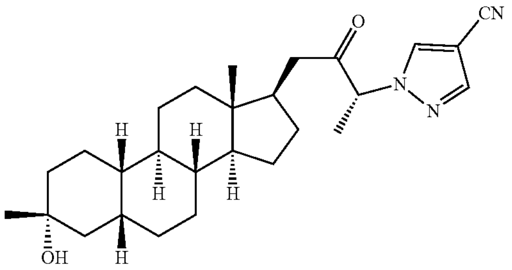

9

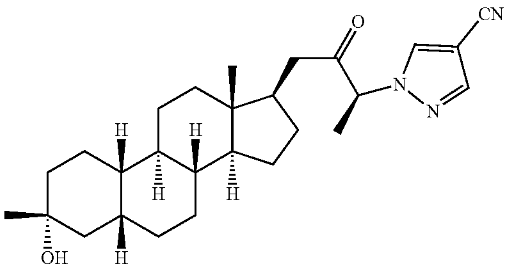

10

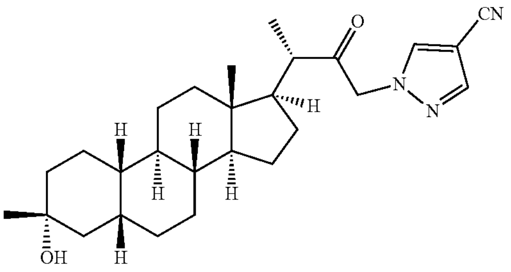

-continued

11

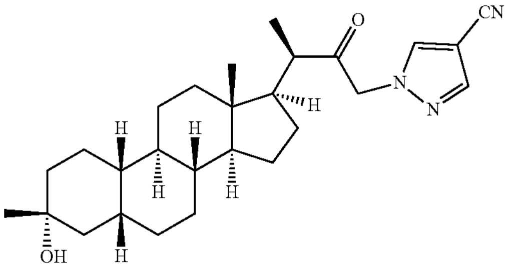

8

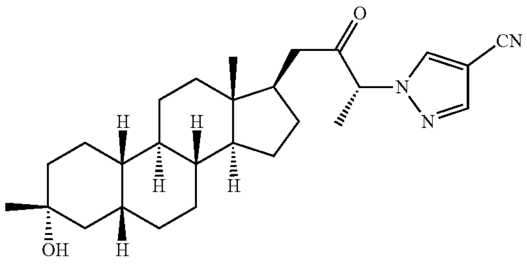

9

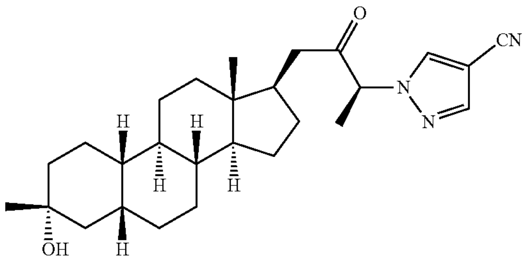

10

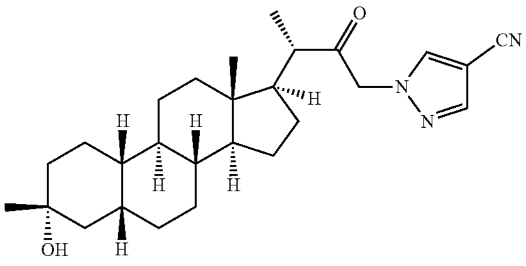

11

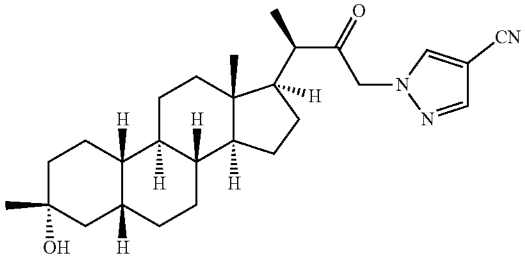

or a pharmaceutically acceptable salt thereof.

45. A pharmaceutical composition comprising a compound or pharmaceutically acceptable salt of claim 1, and a pharmaceutically acceptable excipient.

46. A method of treating a CNS-related disorder related to GABA function in a subject in need thereof, comprising administering to the subject an effective amount of a compound or pharmaceutically acceptable salt of claim 1, wherein the CNS-related disorder is depression.

47. The method of claim 46, wherein the depression is postpartum depression or a major depressive disorder.

48. The method of claim 47, wherein the major depressive disorder is a moderate major depressive disorder or a severe major depressive disorder.

49. The compound or pharmaceutically acceptable salt of claim 44, wherein the compound of Formula (VI-H) is

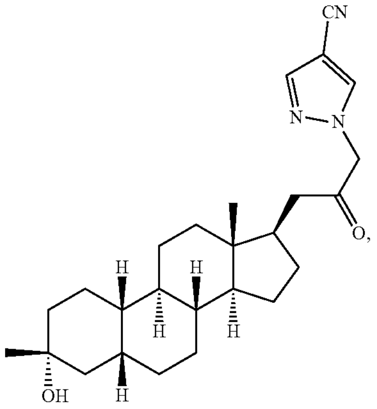

or a pharmaceutically acceptable salt thereof.

50. The compound or pharmaceutically acceptable salt of claim 44, wherein the compound of Formula (VI-H) is

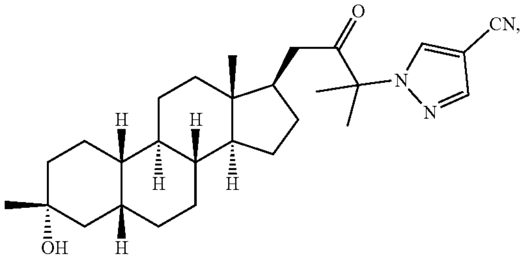

or a pharmaceutically acceptable salt thereof.

51. The compound or pharmaceutically acceptable salt of claim 44, wherein the compound of Formula (VI-H) is

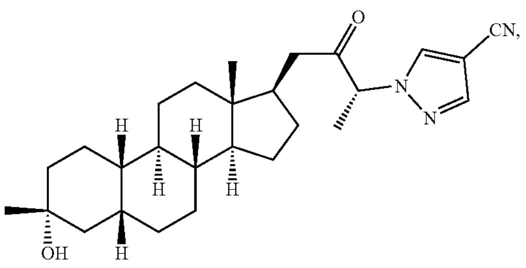

or a pharmaceutically acceptable salt thereof.

52. The compound or pharmaceutically acceptable salt of claim 44, wherein the compound of Formula (VI-H) is

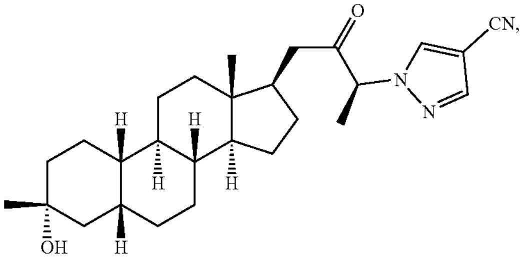

or a pharmaceutically acceptable salt thereof.

53. The compound or pharmaceutically acceptable salt of claim 44, wherein the compound of Formula (VI-H) is

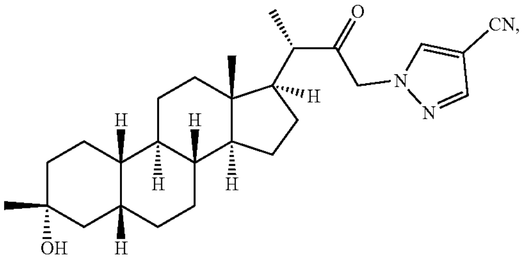

or a pharmaceutically acceptable salt thereof.

54. The compound or pharmaceutically acceptable salt of claim 44, wherein the compound of Formula (VI-H) is

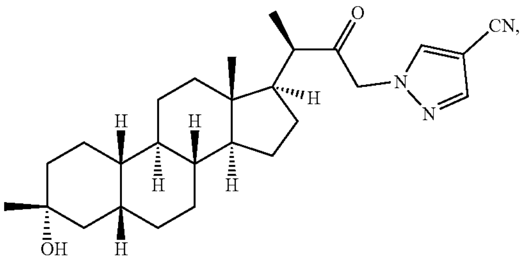

or a pharmaceutically acceptable salt thereof.

55. A pharmaceutical composition comprising a compound or pharmaceutically acceptable salt of claim 44, and a pharmaceutically acceptable excipient.

56. A method of treating a CNS-related disorder related to GABA function in a subject in need thereof, comprising administering to the subject an effective amount of a compound or pharmaceutically acceptable salt of claim 44, wherein the CNS-related disorder is depression.

57. The method of claim 56, wherein the depression is postpartum depression or a major depressive disorder.

58. The method of claim 57, wherein the major depressive disorder is a moderate major depressive disorder or a severe major depressive disorder.

* * * * *